(12) United States Patent
Kalayoglu

(10) Patent No.: US 9,089,579 B2
(45) Date of Patent: Jul. 28, 2015

(54) METHODS AND COMPOSITIONS FOR TREATING METABOLIC SYNDROME

(75) Inventor: Murat V. Kalayoglu, Silver Spring, MD (US)

(73) Assignee: Topokine Therapeutics, Inc., Newton, MA (US)

( * ) Notice: Subject to any disclaimer, the term of this patent is extended or adjusted under 35 U.S.C. 154(b) by 27 days.

(21) Appl. No.: 13/980,179

(22) PCT Filed: Jan. 18, 2012

(86) PCT No.: PCT/US2012/021692
§ 371 (c)(1),
(2), (4) Date: Sep. 19, 2013

(87) PCT Pub. No.: WO2012/099942
PCT Pub. Date: Jul. 26, 2012

(65) Prior Publication Data
US 2014/0045933 A1    Feb. 13, 2014

Related U.S. Application Data

(60) Provisional application No. 61/434,337, filed on Jan. 19, 2011.

(51) Int. Cl.
| A61K 31/5575 | (2006.01) |
| C07C 405/00 | (2006.01) |
| A61P 3/10 | (2006.01) |
| A61K 31/5585 | (2006.01) |
| C07C 69/732 | (2006.01) |
| C07C 235/30 | (2006.01) |
| C07D 307/20 | (2006.01) |

(52) U.S. Cl.
CPC .......... *A61K 31/5575* (2013.01); *A61K 31/5585* (2013.01); *C07C 69/732* (2013.01); *C07C 235/30* (2013.01); *C07D 307/20* (2013.01)

(58) Field of Classification Search
CPC ..................... C07C 405/00; A61K 31/5575
USPC ................ 514/573, 530; 560/121; 562/503
See application file for complete search history.

(56) References Cited

U.S. PATENT DOCUMENTS

| 4,270,537 A | 6/1981 | Romaine |
| 4,596,556 A | 6/1986 | Morrow et al. |
| 4,599,353 A | 7/1986 | Bito |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,011,062 A | 4/1991 | Nakanishi et al. |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,296,504 A | 3/1994 | Stjernschantz et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,422,368 A | 6/1995 | Stjernschantz et al. |

(Continued)

FOREIGN PATENT DOCUMENTS

| EA | 006556 B1 | 2/2006 |
| EP | 2228058 A1 | 9/2010 |

(Continued)

OTHER PUBLICATIONS

Definition of prevent, Princeton University "About WordNet." WordNet. Princeton University. 2010. <http://wordnet.princeton.edu>, accessed Sep. 18, 2012.*

(Continued)

*Primary Examiner* — Sreeni Padmanabhan
*Assistant Examiner* — Irina Neagu
(74) *Attorney, Agent, or Firm* — Wolf, Greenfield & Sacks, P.C.; C. Hunter Baker; Robin A. Weatherhead

(57) ABSTRACT

Provided are methods, compositions, systems, and kits for treating metabolic syndrome or a disorder associated with metabolic syndrome, e.g., obesity, dyslipidemia, and/or a diabetic condition, comprising administering systemically to a subject one or more compounds of the Formula (I) and/or (II): or a pharmaceutically acceptable salt, hydrate, solvate, stereoisomer, polymorph, tautomer, isotopically enriched derivative, or prodrug thereof, wherein, L, $R_1$; $R_2$, Z, X, A and B are defined herein.

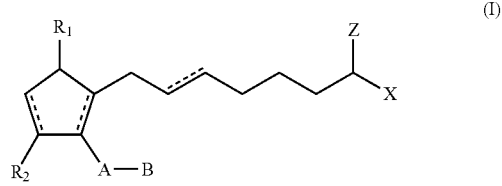

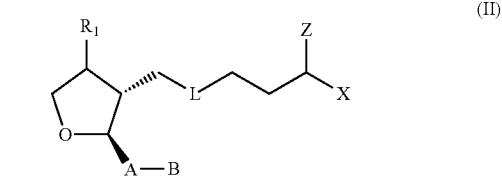

10 Claims, 10 Drawing Sheets

(56) References Cited

U.S. PATENT DOCUMENTS

| | | | |
|---|---|---|---|
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,599,302 A | 2/1997 | Lilley et al. | |
| 5,631,287 A | 5/1997 | Schneider | |
| 5,649,912 A | 7/1997 | Peterson | |
| 5,688,819 A | 11/1997 | Woodward et al. | |
| 5,704,911 A | 1/1998 | Parsons | |
| 5,849,792 A | 12/1998 | Schneider | |
| 5,886,035 A | 3/1999 | Shirasawa et al. | |
| 5,889,052 A | 3/1999 | Klimko et al. | |
| 5,893,397 A | 4/1999 | Peterson et al. | |
| 5,990,139 A | 11/1999 | Yano et al. | |
| 5,993,412 A | 11/1999 | Deily et al. | |
| 6,232,344 B1 | 5/2001 | Feng et al. | |
| 6,235,781 B1 | 5/2001 | Weiner et al. | |
| 6,262,105 B1 | 7/2001 | Johnstone | |
| 6,403,649 B1 | 6/2002 | Woodward et al. | |
| 6,646,001 B2 | 11/2003 | Hellberg et al. | |
| 6,730,707 B2 | 5/2004 | Pintor et al. | |
| 6,864,282 B2 | 3/2005 | Ling et al. | |
| 6,911,474 B2 | 6/2005 | Piomelli et al. | |
| 6,933,289 B2 | 8/2005 | Lyons et al. | |
| 7,070,768 B2 | 7/2006 | Krauss | |
| 7,125,542 B2 | 10/2006 | Miller et al. | |
| 7,351,404 B2 | 4/2008 | Woodward et al. | |
| 7,666,912 B2 | 2/2010 | Grosskreutz et al. | |
| 8,273,362 B2 | 9/2012 | Philips et al. | |
| 8,426,471 B1 | 4/2013 | Kalayoglu et al. | |
| 8,569,376 B2 | 10/2013 | Kalayoglu et al. | |
| 8,778,981 B2 | 7/2014 | Kalayoglu et al. | |
| 8,829,050 B2 * | 9/2014 | Grosskreutz et al. | 514/573 |
| 8,877,807 B2 | 11/2014 | Grosskreutz et al. | |
| 2003/0181354 A1 | 9/2003 | Abdulrazik | |
| 2004/0082660 A1 | 4/2004 | Ueno | |
| 2004/0115234 A1 | 6/2004 | Gewirtz | |
| 2005/0058614 A1 | 3/2005 | Krauss | |
| 2005/0261373 A1 | 11/2005 | Ueno | |
| 2005/0261641 A1 | 11/2005 | Warchol et al. | |
| 2008/0015257 A1 | 1/2008 | Grosskreutz et al. | |
| 2008/0107738 A1 | 5/2008 | Philips et al. | |
| 2009/0042909 A1 | 2/2009 | Karnik | |
| 2010/0104654 A1 | 4/2010 | Robinson et al. | |
| 2010/0234466 A1 | 9/2010 | Grosskreutz et al. | |
| 2012/0295972 A1 | 11/2012 | Woodward et al. | |
| 2013/0178525 A1 | 7/2013 | Kalayoglu et al. | |
| 2014/0163098 A1 | 6/2014 | Grosskreutz et al. | |
| 2014/0350104 A1 | 11/2014 | Kalayoglu et al. | |

FOREIGN PATENT DOCUMENTS

| | | |
|---|---|---|
| RU | 2157689 C2 | 10/2000 |
| WO | WO 97/13537 A1 | 4/1997 |
| WO | WO 97/37705 A1 | 10/1997 |
| WO | WO 99/34850 A1 | 7/1999 |
| WO | WO 03/066008 A1 | 8/2003 |
| WO | WO 2005/034889 A2 | 4/2005 |
| WO | WO 2005/034890 A2 | 4/2005 |
| WO | WO 2006/048750 A2 | 5/2006 |
| WO | WO 2007/111806 A2 | 10/2007 |
| WO | WO 2011/057129 A2 | 5/2011 |

OTHER PUBLICATIONS

Gregersen, P.K. et al. Nature Reviews Genetics 2006, 7, 917-928.*
The American Diabetes Association Diabetes Care 2004, 27 (Supplement 1), S5-S10.*
The American Diabetes Association Standards of Medical Care in Diabetes—2008. Diabetes Care 2008, 31 (Supplement 1), S12-S54.*
Invitation to Pay Additional Fees for PCT/US2007/005424, mailed, Aug. 10, 2007.

International Search Report and Written Opinion for Application No. PCT/US2007/005424, mailed Nov. 26, 2007.
International Preliminary Report on Patentability for Application No. PCT/US2007/005424, mailed Sep. 23, 2008.
International Search Report and Written Opinion for Application No. PCT/US2012/070581, mailed May 30, 2013.
International Preliminary Report on Patentability for Application for PCT/US2012/070581, mailed Jul. 3, 2014.
Extended European Search Report for Application No. EP 12736090.7, mailed Jul. 8, 2014.
Invitation to Pay Additional Fees for PCT/US2012/021692, mailed Feb. 21, 2013.
International Search Report and Written Opinion for Application for PCT/US2012/021692, mailed May 3, 2013.
International Preliminary Report on Patentability for Application for PCT/US2012/021692, mailed Aug. 1, 2013.
[No Author Listed] Allergan Announces FDA Approval of Lumigan as First-Line Treatment for Elevated Eye Pressure in Open-Angle Glaucoma; Indication Expands Approved Uses of Lumigan in the Management of Glaucoma. Business Wire. Jun. 23, 2006. Available at http://findarticles.com/p/articles/mi_m0EIN/is_2006June_23/ai_n26905641. Last visited Aug. 7, 2008. 2 pages.
[No Author Listed] Allergan Announces FDA Approval of Lumigan® as First-Line Treatment for Elevated Eye Pressure in Open-Angle Glaucoma; Indication Expands Approved Uses of Lumigan(R) in the Management of Glaucoma. Allergan Press Release. Jun. 23, 2006. Avaiable at http://agn360.client.shareholder.com/releasedetail.cfm?ReleaseID=201809. Last visited Sep. 9, 2008. 3 pages.
[No Author Listed] Excerpts from BodybuildingForYou—Bodybuilding Forums: Anabolic Steroids/Prohormones, and Testosterone Enhancers <http://www.bodybuildingforyou.com/forums/anabolic-steroids-prohormones-testosterone-enhancers/>/ Anabolic Steroids & Anabolic Chemistry & Testosterone Enhancers <http://www.bodybuildingforyou.com/forums/anabolic-steroids-anabolic-chemistry-testosterone-enhancers/>/ Anabolic Steroid, HGH, IGF, Insulin and Ancillary Profiles, pgf2a parts 3-5, post nos. 35-37 by RRAdam on Jul. 12, 2005, http://www.bodybuildingforyou.com/forums/anabolic-steroids-anabolic-chemistry-testosterone-enhancers/22591-anabolic-steroid-hgh-igf-insulin-ancillary-profiles-2.html (14 pages).
[No Author Listed] Excerpts from Wanna Be Big Bodybuilding and Weightlifting Forums: Community Central <http://www.wannabebigforums.com/archive/index.php/f-20.html>/ General Chat <http://www.wannabebigforums.com/archive/index.php/f-12.html>/The Myostatin Gene, posted at 4:22pm, Feb. 5, 2001, by Cackerot69, http://www.wannabebiciforums.com/archive/index.php/t-359.html (4 pages).
[No Author Listed] FDA CDER Approval Letter (3 pages) and Toxicology Study #5 from CDER Pharmacology Review (cover page and pp. 43-44 of 107 included) for Lumigan (Bimatoprost Ophthalmic Solution), NDA Application No. 21-275 (FDA Approval Date: Mar. 16, 2001), available at http://www.fda.gov/cder/foi/nda/2001/21275_Lumigan.htm (last visited May 23, 2008).
[No Author Listed] FDA CDER Toxicology Study #18 from CDER Pharmacology Review (cover page and pp. 67-69 of 107 included) for Lumigan (Bimatoprost Ophthalmic Solution), NDA Application No. 21-275 (FDA Approval Date: Mar. 16, 2001), available at http://www.fda.gov/cdergoi/nda/2001/21275_Lumigan.htm (last visited Dec. 22, 2008).
[No Author Listed] Kegg Drug: D02724, [online] retrieved on Nov. 30, 2007, (2007), retrieved from http://www.genome.ad.jp/dbget—bin/www_bget?drug+D02724 and http://www.genome.ad.jp/dbget-bin/www_bget?pathway+map07035, printed p. 1 and printed pp. 1-3, respectively.
[No Author Listed] Latisse and Safety. Last accessed on Jul. 24, 2012 at http://www.latisseonline.com/latisse-safety/ 2 pages.
[No Author Listed] Material Safety Data Sheet for Lutalyse® Sterile Solution, dated Jun. 23, 1997, available at httplApfww.lutelysacomipahirnageslmsde . . . usiLutalvse.pdf (last visited Dec. 22, 2006).
[No Author Listed] Original New Animal Drug Application for ProstaMateTm (dinoprost tromethamine injection) Sterile Solution

(56) References Cited

OTHER PUBLICATIONS (ANADA No. 200-253). Dated Feb. 12, 1999. Available at http://www.fdagovlohrmsidockets/98fr1200253fi.pdf. Last visited Dec. 22, 2008.
[No Author Listed] Pfizer Inc., Citizen Petition to the Food and Drug Administration: Revoke Approval of Allergan's Supplemental NDA #21-257/S-013 for Lumigan (Bimatoprost Ophthalmic Solution 0.03%) and Deny Alcon's Supplemental NDA for Travatan (Travoprost Ophthalmic Solution 0.004%), submitted on Nov. 1, 2006, available at http://www.fda.gov/ohrms/dockets/dockets/06p0450/06p-0450-cp00001-toc.htm.
[No Author Listed] Prescribing Information for Saflutan® 15 micrograms/ml eye drops, solution, single-dose container (tafluprost), dated Aug. 2009.
[No Author Listed] Product label of Decadron® dexamethasone tablets, label for May 17, 2004 approval (NDA No. 011664), available at http://dailymed.nlm.nih.gov/dailymed/druu1nfo.cfm?id=2934 (last visitedDec. 22, 2008).
[No Author Listed] Product Label of Lumigano (bimatoprost ophthalmic solution) 0.03%, label for Jun. 22, 2006 approval of new or modified indication, available at http://www.fda.gov/cder/foi/labe1/2006/021275s013Ib1.pdf (last visited Sep. 9, 2008).
[No Author Listed] Product Label of Travatan® (travoprost ophthalmic solution) 0.004%, label for Feb. 13, 2003 approval of efficacy supplement with clinical data to support, available at http://www.fda.gov/cder/foUlabe1/2003/021257s0061bl.pdf (last visited Sep. 9, 2008).
[No Author Listed] Product Label of Xalatan® (latanoprost ophthalmic solution), label for Dec. 20, 2002 approval of new or modified indication, available at http://www.fda.gov/cder/foi/label/2002/20597SE1-010_Xalatan_lbl.pdf (last visited Sep. 9, 2008).
[No Author Listed] Prostaglandin analogues. Entrepreneur.com. 2008. Available at http://www.entrepreneur.com/tradejournals/article/print/166777491.html. 2 pages.
[No Author Listed] Travatan™ (travoprost ophthalmic solution) 0.004% Sterile. NDA 21-257. Alcon Laboratories Inc. 2001. 7 pages.
Aihara et al., Incidence of deepening of the upper eyelid sulcus after switching from latanoprost to bimatoprost. Jpn J Ophthalmol. Nov. 2011;55(6):600-4. Epub Sep. 28, 2011.
Aydin et al., Recovery of orbital fat pad prolapsus and deepening of the lid sulcus from topical bimatoprost therapy: 2 case reports and review of the literature. Cutan Ocul Toxicol. Sep. 2010;29(3):212-6.
Casimir et al., Preadipocyte differentiation blocked by prostaglandin stimulation of prostanoid FP2 receptor in murine 3T3-L1 cells. Differentiation. Jul. 1996;60(4):203-10.
Casmir, Regulation of early preadipocyte differentiation: cAMP and prostaglandin F-2-alpha. ProQuest Dissertations and Theses; 1996; ProQuest Dissertations & Theses (PQDT). UMI No. 9634889. 162 pages.
Chapman et al., Glucocorticoid regulation of adipocyte differentiation: hormonal triggering of the developmental program and induction of a differentiation-dependent gene. J Cell Biol. Oct. 1985;101(4):1227-35.
Choi et al., In vitro study of antiadipogenic profile of latanoprost, travoprost, bimatoprost, and tafluprost in human orbital preadiopocytes. J Ocul Pharmacol Ther. Apr. 2012;28(2):146-52. Epub Nov. 22, 2011. E-pub version.
Davidson et al., Weight control and risk factor reduction in obese subjects treated for 2 years with orlistat: a randomized controlled trial. JAMA. Jan. 20, 1999;281(3):235-42. Erratum in: JAMA Apr. 7, 1999;281(13):1174.
Filippopoulos et al., Periorbital changes associated with topical bimatoprost. Ophthal Plast Reconstr Surg. Jul.-Aug. 2008;24(4):302-7.
Gaidhu et al., Chronic AMP-kinase activation with AICAR reduces adiposity by remodeling adipocyte metabolism and increasing leptin sensitivity. J Lipid Res. Sep. 2011;52(9):1702-11. Epub Jul. 7, 2011.
Grosskreutz et al., Periorbital Fat Loss and Eyelid Sulcus Deepening after Bimatoprost Therapy. Final Program and Abstract Book, pp. 49 and 53, distributed at The American Glaucoma Society 2006 Annual Meeting, Mar. 2-5, 2006.
Grosskreutz et al., Periorbital Fat Loss and Eyelid Sulcus Deepening after Bimatoprost Therapy. Poster presented at the American Glaucoma Society 2006 Annual Meeting, Charleston, South Carolina, Mar. 2-5, 2006 (1 page).
Grosskreutz, Abstract submitted on Nov. 1, 2005 to the American Glaucoma Society for the American Glaucoma Society 2006 Annual Meeting (1 page).
Hata et al., Pharmacology and signaling of prostaglandin receptors: multiple roles in inflammation and immune modulation. Pharmacol Ther. Aug. 2004;103(2):147-66.
Holmstrom et al., Analytic review of bimatoprost, latanoprost and travoprost in primary open angle glaucoma. Curr Med Res Opin. Nov. 2005;21(11):1875-83.
Husain et al., Acute effects of PGF2alpha on MMP-2 secretion from human ciliary muscle cells: a PKC- and ERK-dependent process. Invest Ophthalmol Vis Sci. May 2005;46(5):1706-13.
Inoue et al., Deepening of the Upper Eyelid Sulcus Caused by 5 Types of Prostaglandin Analogs. J Glaucoma. Aug. 29, 2012. [Epub ahead of print] E-pub version. 6 pages.
Jabbour et al., A positive feedback loop that regulates cyclooxygenase-2 expression and prostaglandin F2alpha synthesis via the F-series-prostanoid receptor and extracellular signal-regulated kinase 1/2 signaling pathway. Endocrinology. Nov. 2005;146(11):4657-64. Epub Aug. 4, 2005.
Klein et al., Non-invasive cryolipolysis for subcutaneous fat reduction does not affect serum lipid levels or liver function tests. Lasers Surg Med. Dec. 2009;41(10):785-90.
Lepak et al. Inhibition of adipose differentiation by 9 alpha, 11 beta-prostaglandin F2 alpha. Prostaglandins. Dec. 1993;46(6):511-7.
Lepak et al., Prostaglandin F2 alpha stimulates transforming growth factor-alpha expression in adipocyte precursors. Endocrinology. Aug. 1995;136(8):3222-9.
Liszka et al., Effect of lipectomy on growth and development of hyperinsulinemia and hyperlipidemia in the Zucker rat. Plast Reconstr Surg. Sep. 1998;102(4):1122-7.
Liu et al., Postaglandin F2alpha inhibits adipocyte differentiation via a G alpha q-calcium-calcineurin-dependent signaling pathway. J Cell Biochem. Jan. 1, 2007;100(1):161-73.
Löffler et al., Adipose tissue development: the role of precursor cells and adipogenic factors. Part II: the regulation of the adipogenic conversion by hormones and serum factors. Klin Wochenschr. Sep. 1, 1987;65(17):812-7.
Maxey et al., The hydrolysis of bimatoprost in corneal tissue generates a potent prostanoid FP receptor agonist. Surv Ophthalmol. Aug. 2002;47 Suppl 1:S34-40.
Miller et al., The mechanism of inhibition of 3T3-L1 preadipocyte differentiation by prostaglandin F2alpha. Endocrinology. Dec. 1996;137(12):5641-50.
Morley, Orexigenic and anabolic agents. Clin Geriatr Med. Nov. 2002;18(4):853-66. Review.
Nakajima et al., New fluoroprostaglandin F(2alpha) derivatives with prostanoid FP-receptor agonistic activity as potent ocular-hypotensive agents. Biol Pharm Bull. Dec. 2003;26(12):1691-5.
Nakakura et al., Latanoprost therapy after sunken eyes caused by travoprost or bimatoprost. Optom Vis Sci. Sep. 2011;88(9):1140-4.
Ota et al., The IOP-lowering effects and mechanism of action of tafluprost in prostanoid receptor-deficient mice. Br J Ophthalmol May 2007;91(5):673-6. Epub Nov. 23, 2006.
Pantoja et al., Glucocorticoid signaling defines a novel commitment state during adipogenesis in vitro. Mol Biol Cell. Oct. 2008;19(10):4032-41. Epub Jul. 23, 2008.
Park et al., Changes to upper eyelid orbital fat from use of topical bimatoprost, travoprost, and latanoprost. Jpn J Ophthalmol. Jan. 2011;55(1):22-7. Epub Feb. 18, 2011.
Paula et al., Periorbital Fat Loss and Eyelid Sulcus Deepening after Bimatoprost Therapy. Manuscript submitted to Archives of Ophthalmology, Oct. 21, 2005 (10 pages).
Peplinski et al., Deepening of lid sulcus from topical bimatoprost therapy. Optom Vis Sci. Aug. 2004;81(8):574-7.

(56) References Cited

OTHER PUBLICATIONS

Reginato et al., Prostaglandins promote and block adipogenesis through opposing effects on peroxisome proliferator-activated receptor gamma. J Biol Chem. Jan. 23, 1998;273(4):1855-8.

Robin, An accurate comparison of bimatoprost's efficacy and adverse effects. Arch Ophthalmol. Jul. 2002;120(7):999-1000; author reply 1000.

Sales et al., Expression, localization, and signaling of prostaglandin F2 alpha receptor in human endometrial adenocarcinoma: regulation of proliferation by activation of the epidermal growth factor receptor and mitogen-activated protein kinase signaling pathways. J Clin Endocrinol Metab. Feb. 2004;89(2):986-93.

Sales et al., F-prostanoid receptor regulation of fibroblast growth factor 2 signaling in endometrial adenocarcinoma cells. Endocrinology. Aug. 2007;148(8):3635-44. Epub May 3, 2007.

Schiwek et al., Glucocorticoid hormones contribute to the adipogenic activity of human serum. Endocrinology. Feb. 1987;120(2):469-74. Abstract only.

Selliah et al., AL-12182, a novel 11-oxa prostaglandin analog with topical ocular hypotensive activity in the monkey. Bioorg Med Chem Lett. Sep. 6, 2004;14(17):4525-8.

Serrero et al., Prostaglandin F2 alpha inhibits epidermal growth factor binding to cellular receptors on adipocyte precursors in primary culture. Biochem Biophys Res Commun. Jul. 26, 1995;212(3):1125-32.

Serrero et al., Prostaglandin F2 alpha inhibits the differentiation of adipocyte precursors in primary culture. Biochem Biophys Res Commun. Mar. 16, 1992;183(2):438-42.

Serrero et al., Prostaglandin F2alpha receptor (FP receptor) agonists are potent adipose differentiation inhibitors for primary culture of adipocyte precursors in defined medium. Biochem Biophys Res Commun. Apr. 7, 1997;233(1):200-2.

Sharif et al., Agonist activity of bimatoprost, travoprost, latanoprost, unoprostone isopropyl ester and other prostaglandin analogs at the cloned human ciliary body FP prostaglandin receptor. J Ocul Pharmacol Ther. Aug. 2002;18(4):313-24.

Shi et al., A glucocorticoid-induced leucine-zipper protein, GILZ, inhibits adipogenesis of mesenchymal cells. EMBO Rep. Apr. 2003;4(4):374-80. Epub Mar. 14, 2003.

Shugart et al., Dexamethasone signaling is required to establish the postmitotic state of adipocyte development. Cell Growth Differ. Oct. 1997;8(10):1091-8.

Tappeiner et al., [Orbital fat atrophy in glaucoma patients treated with topical bimatoprost—can bimatoprost cause enophthalmos?]. Klin Monbl Augenheilkd. May 2008;225(5):443-5. English abstract only.

Tsuboi et al., Prostanoid EP4 receptor is involved in suppression of 3T3-L1 adipocyte differentiation. Biochem Biophys Res Commun. Sep. 24, 2004;322(3):1066-72.

Woodward et al., The pharmacology of bimatoprost (Lumigan™). Surv Ophthalmol. May 2001;45 Suppl 4:S337-45.

Yam et al., Bilateral deepening of upper lid sulcus from topical bimatoprost therapy. J Ocul Pharmacol Ther. Oct. 2009;25(5):471-2.

International Search Report and Written Opinion for Application No. PCT/US2014/038067, mailed Sep. 29, 2014.

International Search Report and Written Opinion for Application No. PCT/US2014/037512, mailed Dec. 4, 2014.

Invitation to Pay Additional Fees for Application No. PCT/US2014/037512, mailed Aug. 21, 2014.

Anderson et al., High-carbohydrate, high-fiber diets for insulin-treated men with diabetes mellitus. Am J Clin Nutr. Nov. 1979;32(11):2312-21.

Ichhpujani et al., Comparison of human ocular distribution of bimatoprost and latanoprost. J Ocul Pharmacol Ther. Apr. 2012;28(2):134-45. doi: 10.1089/jop.2011.0097. Epub Dec. 2, 2011.

Klein et al., Absence of an effect of liposuction on insulin action and risk factors for coronary heart disease. N Engl J Med. Jun. 17, 2004;350(25):2549-57.

Mohammed et al., Long-term effects of large-volume liposuction on metabolic risk factors for coronary heart disease. Obesity (Silver Spring). Dec. 2008;16(12):2648-51. doi: 10.1038/oby.2008.418. Epub Sep. 25, 2008.

Porter et al., Abdominal subcutaneous adipose tissue: a protective fat depot? Diabetes Care. Jun. 2009;32(6):1068-75. doi: 10.2337/dc08-2280. Epub Feb. 24, 2009.

Ross, Does exercise without weight loss improve insulin sensitivity? Diabetes Care. Mar. 2003;26(3):944-5.

Shah et al., A cross-sectional survey of the association between bilateral topical prostaglandin analogue use and ocular adnexal features. PLoS One. May 1, 2013;8(5):e61638. doi: 10.1371/journal.pone.0061638. Print 2013. 7 pages.

Sjöquist et al., Ocular and systemic pharmacokinetics of latanoprost in humans. Surv Ophthalmol Aug. 2002;47 Suppl 1:S6-12.

Sjöquist et al., The pharmacokinetics of a new antiglaucoma drug, latanoprost, in the rabbit. Drug Metab Dispos. Aug. 1998;26(8):745-54.

* cited by examiner

| Group Number | Number of Animals | Treatment | Dose | Route | Frequency |
|---|---|---|---|---|---|
| 1 | 5 | Topical vehicle | 0.1 ml | Topical to all torso right of midline | Daily, days 0-27 |
| 2 | 5 | SC vehicle (PBS) | 0.1 ml | SC to right flank | Daily, days 0-27 |
| 3 | 5 | Bimatoprost | 100 mcg/0.1 ml | Topical to all torso right of midline | Daily, days 0-27 |
| 4 | 5 | Bimatoprost | 300 mcg/0.1 ml | Topical to all torso right of midline | Daily, days 0-27 |
| 5 | 5 | Bimatoprost free acid | 30 mcg/0.1 ml | SC to right flank | Daily, days 0-27 |
| 6 | 5 | Bimatoprost free acid | 30 mcg/0.1 ml | Intraperitoneal | Daily, days 0-27 |
| 7 | 5 | Bimatoprost free acid | 100 mcg/0.1 ml | Topical to all torso right of midline | Daily, days 0-27 |
| 8 | 5 | Bimatoprost free acid | 300 mcg/0.1 ml | Topical to all torso right of midline | Daily, days 0-27 |
| 9 | 5 | Bimatoprost isopropyl ester | 30 mcg/0.1 ml | SC to right flank | Daily, days 0-27 |
| 10 | 5 | Bimatoprost isopropyl ester | 100 mcg/0.1 ml | Topical to all torso right of midline | Daily, days 0-27 |
| 11 | 5 | Bimatoprost Isopropyl ester | 300 mcg/0.1 ml | Topical to all torso right of midline | Daily, days 0-27 |

Figure 1

| Group | Treatment | Weight gain (g) [95% CI] | Relative reduction vs. Topical Vehicle Control | Relative reduction vs. SC Vehicle Control |
|---|---|---|---|---|
| 1 | Vehicle Control (HRT base; topical) | 15.0 [13.7-16.3] | --- | --- |
| 2 | Vehicle Control (PBS; s.c.) | 16.3 [14.9-17.7] | --- | --- |
| 3 | 100 mcg/0.1 ml Bimatoprost (topical) | 17.3 [16.6-17.9] | -15.2% | --- |
| 4 | 300 mcg/0.1 ml Bimatoprost (topical) | 12.8 [11.2-14.3] | 14.8% | --- |
| 5 | 30 mcg/0.1 ml Bimatoprost free acid (s.c.) | 16.1 [14.7-17.5] | --- | 1.2% |
| 6 | 30 mcg/0.1 ml Bimatoprost free acid (i.p.) | 16.1 [15.4-16.8] | --- | 1.5% |
| 7 | 100 mcg/0.1 ml Bimatoprost free acid (topical) | 12.5 [11.4-13.6] | 16.4% | --- |
| 8 | 300 mcg/0.1 ml Bimatoprost free acid (topical) | 9.9 [8.6-11.2] | 33.9%* | --- |
| 9 | 30 mcg/0.1 ml Bimatoprost isopropyl ester (s.c.) | 16.3 [15.2-17.4] | --- | 0.0% |
| 10 | 100 mcg/0.1 ml Bimatoprost isopropyl ester (topical) | 8.2 [7.5-9.0] | 45.0%** | --- |
| 11 | 300 mcg/0.1 ml Bimatoprost isopropyl ester (topical) | 7.8 [6.6-8.9] | 48.3%** | --- |

*$p < .01$, **$p < .001$ by Tukey.

Figure 2

| Group | Treatment | Triglycerides reduction vs. control | Cholesterol reduction vs. control |
|---|---|---|---|
| 1 | Vehicle Control (HRT base; topical) | | |
| 2 | Vehicle Control (PBS; s.c.) | -4% (increase) | -19% (increase) |
| 3 | 100 mcg/0.1 ml Bimatoprost (topical) | 1% | 5% |
| 4 | 300 mcg/0.1 ml Bimatoprost (topical) | 3% | 11% |
| 5 | 30 mcg/0.1 ml Bimatoprost free acid (s.c.) | 3% | 12% |
| 6 | 30 mcg/0.1 ml Bimatoprost free acid (i.p.) | 2% | 0% |
| 7 | 100 mcg/0.1 ml Bimatoprost free acid (topical) | 23%** | 14% |
| 8 | 300 mcg/0.1 ml Bimatoprost free acid (topical) | 22%** | 10% |
| 9 | 30 mcg/0.1 ml Bimatoprost isopropyl ester (s.c.) | 0% | 0% |
| 10 | 100 mcg/0.1 ml Bimatoprost isopropyl ester (topical) | 44%** | 24%** |
| 11 | 300 mcg/0.1 ml Bimatoprost isopropyl ester (topical) | 42%** | 19% |

**$p < .01$ by Tukey.

Figure 4

| Group Number | Number of Animals | Treatment | Dose | Route | Frequency |
|---|---|---|---|---|---|
| 1 | 3 | Vehicle | 0.3 ml | Topical to all torso right of midline | Qd Days 0-27 |
| 2 | 3 | Latanoprost 0.005% | 15 mcg/ 0.3 ml | Topical to all torso right of midline | Qd Days 0-27 |
| 3 | 3 | Latanoprost 0.05% | 150 mcg/ 0.3 ml | Topical to all torso right of midline | Qd Days 0-27 |
| 4 | 3 | Latanoprost 0.5% | 1500 mcg/ 0.3 ml | Topical to all torso right of midline | Qd Days 0-27 |

Figure 6

| Group | Mean weight gain (g) ±SEM | Reduction vs. vehicle (%) |
|---|---|---|
| Vehicle (control) | 167.7 ( 0.7) | |
| Latanoprost 0.005% | 160.3 (11.9) | 4.4 |
| Latanoprost 0.05% | 152.7 ( 6.4) | 8.9* |
| Latanoprost 0.5% | 139.0 ( 1.2) | 17.1** |

*$p < .05$ by Tukey.  **$p < .01$ by Tukey.*

Figure 7

| Group | Triglycerides | LDL | HDL | HDL:LDL |
|---|---|---|---|---|
| Vehicle (control) | 778 ± 79 | 20.7 ± 2.7 | 56.3 ± 2.4 | 2.73 |
| Latanoprost 0.005% | 899 ± 240 (116%) | 23.0 ± 4.0 (111%) | 57.3 ± 3.3 (102%) | 2.49 (91%) |
| Latanoprost 0.05% | 655 ± 14 ( 84%) | 17.0 ± 1.7 ( 82%) | 57.7 ± 2.3 (102%) | 3.39 (124%) |
| Latanoprost 0.5% | 563 ± 85 ( 72%) | 14.3 ± 1.8 ( 69%) | 59.3 ± 2.3 (105%) | 4.14 (152%)* |

*$p < .05$ for one-sided superiority of latanoprost 0.5 vs. vehicle.

| Group | AUC$_{15-120}$ | % of Vehicle (control) |
|---|---|---|
| Vehicle (control) | 38,512 | |
| Latanoprost 0.005% | 38,337 | 100% |
| Latanoprost 0.05% | 33,840 | 88% |
| Latanoprost 0.5% | 28,532 | 74% |

Mean serum glucose Area Under the Curve, 15-120 minutes after oral glucose load (AUC$_{15-120}$), mg*min*dL$^{-1}$

Figure 11

| Route | Species | Weight kg | Conc. mg/ml | Dose ml/d | mg/d | mg/kg/d | mg/m^2/d |
|---|---|---|---|---|---|---|---|
| Eye drop | Human | 70 | 0.3 | 0.05 | 0.02 | 0.00002 | 0.008 |
| Skin* | Human | 70 | 7 | 1 | 7 | 0.1 | 3.7 |
| Skin | Mouse | 0.03 | 1 | 0.1 | 0.1 | 3 | 10 |
| Skin | Mouse | 0.03 | 3 | 0.1 | 0.3 | 10 | 30 |
| Skin | Rat | 0.25 | 0.05 | 0.3 | 0.015 | 0.06 | 0.36 |
| Skin | Rat | 0.25 | 0.5 | 0.3 | 0.15 | 0.6 | 3.6 |
| Skin | Rat | 0.25 | 5 | 0.3 | 1.5 | 6 | 36 |

*not tested

Figure 12

METHODS AND COMPOSITIONS FOR TREATING METABOLIC SYNDROME

CROSS-REFERENCE TO RELATED APPLICATIONS

The present application is a national stage filing under 35 U.S.C. §371 of international PCT application, PCT/US2012/021692, filed Jan. 18, 2012, which claims priority under 35 U.S.C. §119(e) to U.S. Provisional Patent Application, U.S. Ser. No. 61/434,337, filed Jan. 19, 2011, each of which is incorporated herein by reference.

FIELD OF THE INVENTION

The present invention relates to methods and compositions for treating and/or preventing metabolic syndrome or a disorder associated with metabolic syndrome, e.g., obesity, dyslipidemia, and/or a diabetic condition, in the body of a subject. More specifically, obesity, dyslipidemia, and/or a diabetic condition may be treated and/or prevented by administering to a subject a therapeutically effective amount of one or more compounds described herein.

BACKGROUND OF THE INVENTION

Metabolic syndrome, also known as metabolic syndrome X, cardiometabolic syndrome, syndrome X, and insulin resistance syndrome, is a cluster of medical disorders that, when occurring together, increase the risk of diabetes and cardiovascular disease. See, e.g., Alberti et al. *Circulation* 2009; 120:1640-1645. Metabolic syndrome affects 35-40% of American adults, and prevalence increases with age. Principal disorders associated with or used in the diagnosis of metabolic syndrome include, but are not limited to, obesity, dyslipidemia, and diabetic conditions, and conditions associated with these disorders, such as elevated glucose levels and hypertension.

Obesity is a risk factor for a wide array of diseases, for example, type 2 diabetes, hypertension, hyperlipidemia, coronary artery disease, stroke, breast and colon cancer, sleep apnea, gall bladder disease, gastroesophageal reflux disease, fatty liver disease, gout, and thromboembolism. Blood pressure, blood sugar, serum cholesterol, and serum uric acid are usually higher in obese people than in those of normal weight. Despite increased awareness of these health risks, the prevalence of obesity has risen steadily for decades in many industrialized nations. As a result, there has been considerable interest in ways to reduce obesity.

The excess body fat of obese subjects is typically deposited in adipose tissue. This tissue and its principal cell type, the adipocyte, have been implicated in a wide array of diseases, for example, metabolic syndrome, type 2 diabetes, atherosclerosis, fatty liver, hepatic fibrosis, breast cancer, inflammation, depression, and dementia. The causative role of adipose tissue in these diseases appears to involve mediators such as adiponectin, resistin, tumor necrosis factor alpha (TNF-α), interleukin-6 (IL-6), C-reactive protein (CRP), fibrinogen, plasminogen activator inhibitor-1 (PAI-1), and/or C-terminal binding protein (CtBP). As a result, the adipocyte per se, rather than being a mere storehouse for calories, plays a pathogenic role in many diseases and represents a target for therapeutic intervention.

A number of medical conditions are considered to be causes of obesity or local excesses of body fat. Examples include drug-induced obesity, hypothyroidism, pseudohypoparathyroidism, hypothalamic obesity, polycystic ovarian disease, depression, binge eating, Prader-Willi syndrome, Bardet-Biedl syndrome, Cohen syndrome, Down syndrome, Turner syndrome, growth hormone deficiency, growth hormone resistance, leptin deficiency or resistance, HIV lipodystrophy, and Cushing syndrome and pseudo-Cushing syndrome (i.e., characteristic syndrome of excess body fat and other findings due to excessive endogenous or exogenous corticosteroid levels). Some of these conditions, for example, Cushing syndrome, pseudo-Cushing syndrome, and HIV-related lipodystrophy, are associated with other features of metabolic syndrome, such as insulin resistance and dyslipidemia.

Medications known to cause obesity or local excess of body fat include cortisol and analogs, other corticosteroids, megace, sulfonylureas, antiretrovirals, tricyclic antidepressants, monoamine oxidase inhibitors, selective serotonin reuptake inhibitors, oral contraceptives, insulin, risperidone, clozapine, and thiazolidinediones. Some of these medications, for example, corticosteroids and antiretrovirals, are associated with other features of metabolic syndrome, such as insulin resistance and dyslipidemia.

Changes in hormonal status, including physiologic changes such as pregnancy or menopause, may result in obesity in a subject. Smoking cessation commonly leads to weight gain and obesity. Trauma may favor the accumulation of excess body fat by virtue of immobility or disuse of an extremity. Similar problems may affect an immobile subject, such as an astronaut or bedridden subject who is immobilized for an extended period of time. Some tumors, for example, lipomas, are characterized by collections of fat cells that may be amenable to methods to reduce body fat. Even in the absence of underlying pathology, a subject may have cosmetic concerns about body fat. These can usually be attributed to constitutional or hereditary factors, developmental history, age, gender, diet, alcohol use, or other aspects of lifestyle.

A number of methods have been developed to reduce obesity. It is helpful to classify these methods as extractive, metabolic, or adipolytic. Extractive methods, such as lipoplasty (e.g., liposuction) or local excision, are methods whereby fat is physically removed from areas of interest. Such methods do not appear to correct other features of metabolic syndrome. They are costly and may involve scars, post-surgical deformity or regression, discomfort, infection, and other adverse reactions.

In contrast to extractive methods, metabolic methods, which include medications, nutritional supplements, devices, bariatric surgery, and exercise or other body treatment, seek to modify the subject's metabolism (e.g., whether caloric intake, expenditure, or both) such that there is a net loss of fat in the subject. A disadvantage is potential concomitant loss of water, carbohydrates, protein, vitamins, minerals, and other nutrients. Furthermore, traditional diet medications may have undesired side effects, for example, palpitations, tremor, insomnia, and/or irritability in a subject who uses stimulants as appetite suppressants. Drawbacks of surgery are mentioned above. Despite salubrious value, the traditional metabolic methods of diet and exercise are not practical for everybody.

Adipolytic methods aim to cause breakdown of adipocytes and/or their lipid contents. For example, fat deposits can be reduced by exposure to cold temperature or to deoxycholate, a solubilizer which lyses cell membranes and results in local necrosis. Drawbacks of these methods can include poor discrimination between adipose and other nearby tissues, barriers to delivery that require hypodermic needles or special equipment, and adverse effects such as necrosis, inflammation, and pain.

Fat circulates in the blood in various lipid and lipoprotein forms. Common measures of lipid concentration in the blood include serum triglycerides, serum total cholesterol, serum low density lipoprotein (LDL), and serum high density lipoprotein (HDL). These lipid concentrations are heavily influenced by diet and metabolism.

Dyslipidemia is an abnormality in one or more lipid or lipoprotein levels in the blood. Dyslipidemia comprises one or more of: elevated serum triglycerides, elevated total cholesterol, elevated low density lipoprotein (LDL), reduced high density lipoprotein (HDL), and/or abnormal distribution of serum lipoproteins as measured, for example, by nuclear magnetic resonance spectroscopy.

Elevations of some lipid concentrations, e.g. triglycerides and/or LDL, are risk factors for diseases such as atherosclerosis, coronary heart disease, stroke, neurovascular disease, peripheral vascular disease, and diabetes. Conversely, abnormally low levels of HDL are associated with cardiovascular disease. Numerous medications have been developed to treat dyslipidemia, e.g., by reducing lipid and/or lipoprotein concentrations. Of these, the "statins" or HMG CoA reductase inhibitors, which decrease LDL levels, are well known examples. For many patients, however, the currently available therapies are insufficient or unsuitable, for example, due to side effects such as myopathy.

Diabetic conditions include diabetes mellitus and pre-diabetes. Diabetes mellitus, which comprises type 1 diabetes and type 2 diabetes, is a condition characterized by hyperglycemia resulting from the body's inability to use blood glucose for energy. Pre-diabetes is a condition wherein blood glucose levels are higher than normal but not high enough for a diagnosis of diabetes; people with pre-diabetes are at increased risk for developing type 2 diabetes. A common feature of type 2 diabetes and pre-diabetes, insulin resistance, is a physiological condition wherein insulin becomes less effective at lowering blood sugar levels, resulting in elevated blood sugar levels. Impaired glucose tolerance is a condition wherein glucose intake (for example, orally or intravenously) results in abnormally elevated blood sugar levels. Glucose tolerance can be measured, for example, by systematic challenge with an oral glucose load (oral glucose tolerance test). "Diabetic complications" include chronic and acute complications of diabetes. Chronic complications include atherosclerosis, stroke, myocardial ischemia, nephropathy, peripheral neuropathy, retinopathy, infection, foot ulcers, and death. Acute complications include metabolic acidosis, nonketotic hypersosmolar state, volume depletion, coma, and death.

Local reduction of adipose tissue does not treat dyslipidemia or diabetes. The peer-reviewed literature has even expressed concern that lysis of adipocytes could dump lipids into the bloodstream and thereby increase serum lipid concentrations. See, e.g., Klein et al, *Lasers Surg Med* 2009; 41:785-790. In one clinical trial, local reduction of flank fat by cryolipolysis did not cause any change in serum triglycerides, total cholesterol, LDL, or HDL See, e.g., Klein et al, *Lasers Surg Med* 2009; 41:785-790. Likewise, local reduction of hip fat by laser lipolysis caused no change in these parameters. See, e.g., Mordon et al, *J Cosmet Laser Ther* 2009; 11:74-74. Furthermore, surgical removal of subcutaneous fat in hamsters actually increased serum triglyceride levels and insulin resistance due to compensatory deposition of intra-abdominal fat. See, e.g., Weber et al, *Am J Physiol Regul Integr Comp Physiol* 2000; 279:R936-943. Even large-volume lipectomy, which is distinct from local fat reduction, does not consistently elicit a reduction in serum lipids or serum glucose. In one report, 9 of 10 patients who underwent large-volume lipectomy showed reduced serum total cholesterol, but no reduction in triglycerides, or in the HDL:LDL ratio. See, e.g., Baxter, *Aesthet Surg J* 1997; 17:213-215. Surgical lipectomy in Zucker rats showed mean reductions in serum triglycerides and total cholesterol, but no reductions in serum glucose. See, e.g., Liszka et al, *Plast Reconstr Surg* 1998; 102:1122-1127.

Even systemic medical therapy for weight loss does not necessarily lead to absolute benefits in serum lipids or glucose. A landmark randomized controlled trial studied the effects of two years of systemic Orlistat therapy in obese adults. See Davidson et al, *JAMA* 1999; 281:235-243. After two years, subjects randomized to Orlistat 120 mg three times daily lost 8.8% of baseline body weight, compared to 5.8% in the placebo group (p<0.001). However, this weight loss was not accompanied by any absolute improvement in serum lipids or serum glucose.

Therefore, there is a need for new approaches including new methods and compositions for treating and/or preventing metabolic syndrome and associated conditions, for example, treating or preventing obesity, dyslipidemia, and/or diabetic conditions, in a subject in need thereof. These approaches may include reducing fat and/or adipocytes in the subject and optionally also reducing levels of undesired serum lipids and/or serum glucose in the bloodstream.

SUMMARY OF THE INVENTION

The present invention arises in part from a new finding that systemic administration of certain F-series prostaglandins to obese, dyslipidemic, and/or diabetic subjects has a beneficial effect on the subjects. The effects observed in subjects systemically treated with such prostaglandins include reduced obesity, reduced weight gain, reduce serum triglycerides, reduced serum LDL, increased serum HDL, reduced serum glucose, and/or improved glucose tolerance.

The present invention also arises from the observation that systemic administration of certain F-series prostaglandin compounds to obese subjects reduces weight of the subject and/or reduces weight gain in those subjects.

The present invention also arises from the identification of certain particularly useful species from among the genus of F-series prostaglandins for the purposes of the invention.

U.S. Pat. No. 7,666,912, contemplates non-systemic topical, subcutaneous, intramuscular, and intralesional administration of certain prostaglandins, e.g., bimatoprost, latanoprost, and tavoprost, would locally reduce fat in a subject at the site of administration. For instance, the Examples of U.S. Pat. No. 7,666,912 contemplates non-systemic transdermal application of bimatoprost at concentrations of 0.003%, 0.03%, or 0.3%, would locally reduce fat in a subject at the site of administration. The inventor has now discovered that while 0.3% topical bimatoprost locally reduces subcutaneous fat in a subject, the isopropyl ester and free acid of bimatoprost are significantly more effective in reducing subcutaneous fat. The inventor has further discovered that transdermal administration of bimatoprost at 0.3% has no effect on systemic reduction of fat, while the corresponding free acid and isopropyl ester have dramatic systemic effects and systemic fat reduction. The inventor has further found that even higher doses, e.g., 0.7% dose of latanoprost, may be desirable in order to obtain systemic effects transdermally. Furthermore, the inventor discovered that neither subcutaneous nor intraaperitoneal administration of bimatoprost had any significant effect on fat reduction. The inventor contemplates that the observed benefits of transdermal administration may be similarly observed if a time-release formulation, such as a controlled or sustained release, for oral or subcutaneous administration is delivered. Other routes of administration for various time-release formulations are contemplated. These findings and observations, which are the basis for the present invention, are indeed surprising and unexpected, especially considering U.S. Pat. No. 7,666,912 dissuades from systemically administering such compounds.

In one aspect, the invention provides methods, compositions, kits, and systems for treating or preventing metabolic syndrome in a subject in need thereof, the method comprising administering systemically to the subject one or more compounds of Formula (I) or (II), as described below and herein, or a pharmaceutically acceptable salt, hydrate, solvate, stereoisomer, polymorph, tautomer, isotopically enriched derivative, or prodrug thereof.

In certain embodiments, the compound for use in the present invention is of Formula (I):

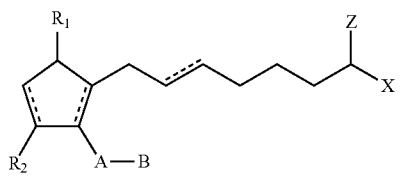

or a pharmaceutically acceptable salt, hydrate, solvate, stereoisomer, polymorph, tautomer, isotopically enriched derivative, or prodrug thereof;
wherein:
each instance of ===== independently represents a single bond or a double bond which can be in the cis or trans configuration;

A is optionally substituted $C_{1-10}$alkylene, optionally substituted $C_{2-10}$alkenylene, or optionally substituted $C_{2-10}$ alkynylene, wherein the alkylene, alkenylene, or alkynylene group is optionally interrupted by one or more —O— or —S— groups;

B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl;

X is —OR$_4$, —SR$_4$, or —N(R$_4$)$_2$, wherein each instance of R$_4$ is independently hydrogen, optionally substituted $C_{1-30}$alkyl, optionally substituted $C_{2-30}$alkenyl, optionally substituted $C_{2-30}$alkynyl, —C(=O)R$_5$, or —C(=O)OR$_5$, wherein R$_5$ is optionally substituted $C_{1-30}$alkyl, optionally substituted $C_{2-30}$alkenyl, or optionally substituted $C_{2-30}$alkynyl, or two R$_4$ groups are joined to form an optionally substituted 3-8-membered-heterocyclyl or optionally substituted 5-14-membered-heteroaryl ring;

Z is =O, =S, or =NR$_Z$, wherein R$_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms; and one of R$_1$ and R$_2$ is =O, —OH, or a —O(CO)R$_6$ group and the other one is —OH or —O(CO)R$_6$, or R$_1$ is =O and R$_2$ is H, wherein R$_6$ is a an optionally substituted $C_{1-20}$alkyl, optionally substituted $C_{2-20}$alkenyl, optionally substituted $C_{2-20}$ alkynyl, or —(CH$_2$)$_m$R$_7$ wherein m is 0 or an integer of between 1-10, inclusive, and R$_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl.

Exemplary compounds of Formula (I) include, but are not limited to:

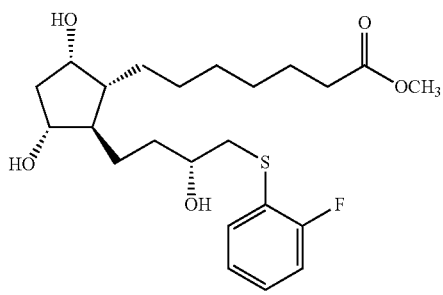 [SMILES: COC(=O)CCCCCC[C@@H]1[C@@H](CC[C@@H](O)CSc2ccccc2F)[C@H](O)C[C@@H]1O]

also referred to herein as CAY10509;

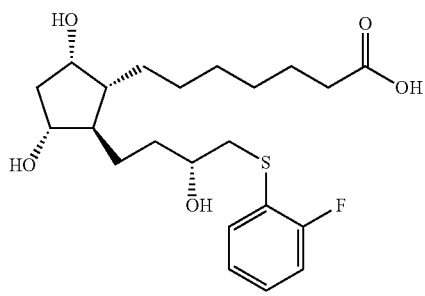 [SMILES: O=C(O)CCCCCC[C@@H]1[C@@H](CC[C@@H](O)CSc2ccccc2F)[C@H](O)C[C@@H]1O]

also referred to herein as CAY10509 free acid;

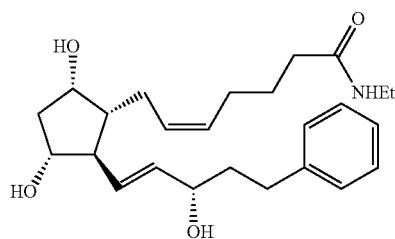

also referred to herein as 17-phenyl trinor prostaglandin F2α ethyl amide, or bimatoprost;

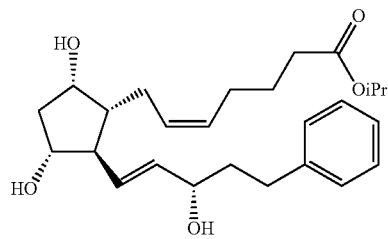 [SMILES: CC(C)OC(=O)CCC/C=C\C[C@@H]1[C@@H](/C=C/[C@@H](O)CCc2ccccc2)[C@H](O)C[C@@H]1O]

also referred to herein as 17-phenyl trinor prostaglandin F2α isopropyl ester, or bimatoprost isopropyl ester;

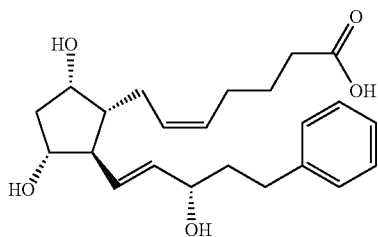 [SMILES: O=C(O)CCC/C=C\C[C@@H]1[C@@H](/C=C/[C@@H](O)CCc2ccccc2)[C@H](O)C[C@@H]1O]

also referred to herein as 17-phenyl trinor prostaglandin F2α, or bimatoprost free acid;

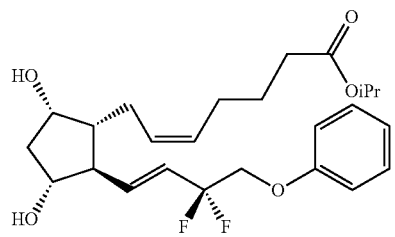

also referred to herein as tafluprost;

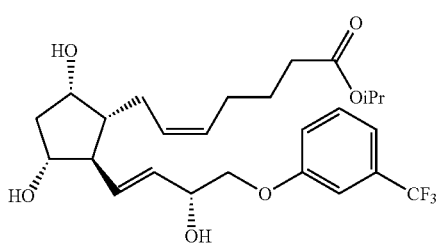 [SMILES: CC(C)OC(=O)CCC/C=C\C[C@@H]1[C@@H](/C=C/[C@@H](O)COc2cccc(C(F)(F)F)c2)[C@H](O)C[C@@H]1O]

also referred to herein as fluprostenol isopropyl ester, or travoprost;

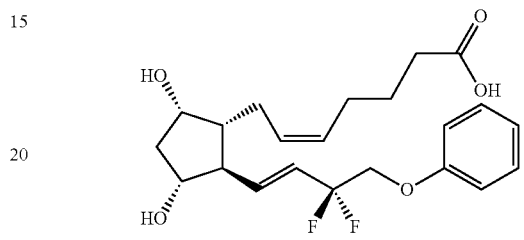

also referred to herein as tafluprost free acid;

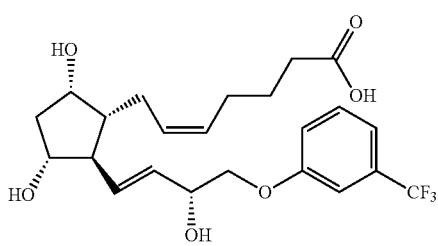 [SMILES: O=C(O)CCC/C=C\C[C@@H]1[C@@H](/C=C/[C@@H](O)COc2cccc(C(F)(F)F)c2)[C@H](O)C[C@@H]1O]

also referred to herein as travoprost free acid;

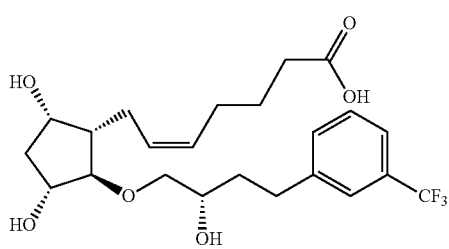

also referred to as AL-16082;
or a pharmaceutically acceptable salt, hydrate, solvate, stereoisomer, polymorph, tautomer, isotopically enriched derivative, or prodrug thereof.

In certain embodiments, the compound for use in the present invention is of Formula (II):

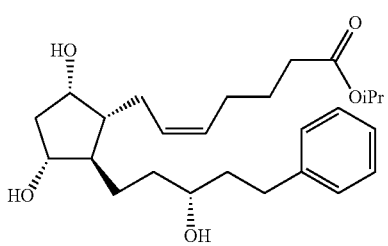 [SMILES: CC(C)OC(=O)CCC/C=C\C[C@@H]1[C@@H](CC[C@@H](O)CCc2ccccc2)[C@H](O)C[C@@H]1O]

also referred to herein as 17-phenyl-13,14-dihydro trinor prostaglandin F2α isopropyl ester, or latanoprost;

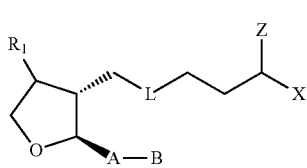

or a pharmaceutically acceptable salt, hydrate, solvate, stereoisomer, polymorph, tautomer, isotopically enriched derivative, or prodrug thereof;
wherein:
L is a group of the formula

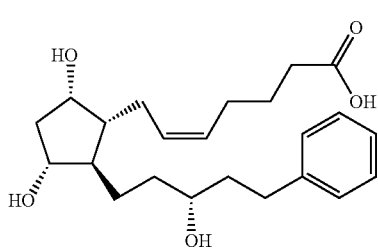 [SMILES: O=C(O)CCC/C=C\C[C@@H]1[C@@H](CC[C@@H](O)CCc2ccccc2)[C@H](O)C[C@@H]1O]

also referred to herein as latanoprost free acid;

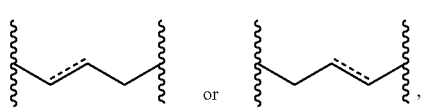

wherein ===== represents a single bond or a double bond, which can be in the cis or trans configuration;

A is optionally substituted $C_{1-10}$alkylene, optionally substituted $C_{2-10}$alkenylene, or optionally substituted $C_{2-10}$ alkynylene, wherein the alkylene, alkenylene, or alkynylene group is optionally interrupted by one or more —O— or —S— groups;

B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl;

X is —OR$_4$, —SR$_4$, or —N(R$_4$)$_2$, wherein each instance of R$_4$ is independently hydrogen, optionally substituted $C_{1-30}$alkyl, optionally substituted $C_{2-30}$alkenyl, optionally substituted $C_{2-30}$alkynyl, —C(=O)R$_5$, or —C(=O)OR$_5$, wherein R$_5$ is optionally substituted $C_{1-30}$alkyl, optionally substituted $C_{2-30}$alkenyl, or optionally substituted $C_{2-30}$alkynyl, or two R$_4$ groups are joined to form an optionally substituted 3-8-membered-heterocyclyl or optionally substituted 5-14-membered-heteroaryl ring;

Z is =O, =S, or =NR$_Z$, wherein R$_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms; and R$_1$ is =O, —OH, or —O(CO)R$_6$, wherein R$_6$ is a an optionally substituted $C_{1-20}$alkyl, optionally substituted $C_{2-20}$alkenyl, optionally substituted $C_{2-20}$ alkynyl, or —(CH$_2$)$_m$R$_7$ wherein m is 0 or an integer of between 1-10, inclusive, and R$_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl.

Exemplary compounds of Formula (II) include, but are not limited to,

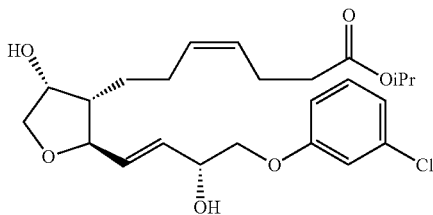

also referred to as AL-12182; and

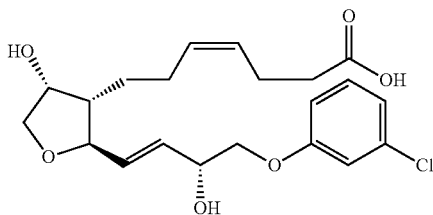 [SMILES: CC(C)OC(=O)CC/C=C\CC[C@H]1[C@@H](O)CO[C@@H]1/C=C/[C@@H](O)COc1cccc(Cl)c1]

also referred to as AL-12182 free acid;
or a pharmaceutically acceptable salt, hydrate, solvate, stereoisomer, polymorph, tautomer, isotopically enriched derivative, or prodrug thereof; wherein ===== , and n are as defined herein.

In certain embodiments, the compound of Formula (I) or (II) is a prodrug of any one of the compounds described herein. Exemplary prodrugs include esters, amides, and/or thioamides of the parent free acid and acyl groups present on the pentacyclic hydroxyl groups.

Compounds described herein are members of a class that has been previously described, for example, in U.S. Pat. Nos. 4,599,353, 5,296,504, 5,422,368, 5,688,819, 6,232,344, 6,403,649, and 7,666,912, Selliah et al (*Bioorg Med Chem Lett* 2004; 14:4525-4528), and Feng et al (*Bioorg Med Chem* 2009; 17:576-584), each of which is incorporated herein by reference. This class of compounds, which are analogs of Prostaglandin F2α, is known to reduce intraocular pressure in the eye.

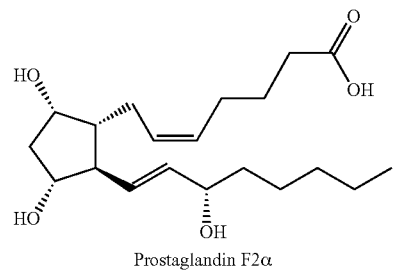 [SMILES: CCCCC[C@H](O)/C=C/[C@@H]1[C@@H](C/C=C\CCCC(=O)O)[C@@H](O)C[C@H]1O]

Prostaglandin F2α

In a second aspect, the invention provides methods, compositions, kits, and systems for treating or preventing a disorder associated with or used in the diagnosis of metabolic syndrome, such as obesity, dyslipidemia, and/or a diabetic condition, and/or a condition associated with these disorders, in a subject in need thereof, the method comprising administering to the subject one or more compounds of Formula (I) or (II), or a pharmaceutically acceptable salt, hydrate, solvate, stereoisomer, polymorph, tautomer, isotopically enriched derivative, or prodrug thereof.

In a third aspect, the invention provides a methods, compositions, kits, and systems for treating or preventing obesity in a subject, the method including administering to a subject one or more compounds of Formula (I) or (II), or a pharmaceutically acceptable salt, hydrate, solvate, stereoisomer, polymorph, tautomer, isotopically enriched derivative, or prodrug thereof. In some embodiments, the subject has obesity but does not suffer from metabolic syndrome.

In certain embodiments, the method of treating obesity comprises reducing adipocytes. In certain embodiments, the subject also suffers from or is likely to suffer from an adipocyte-related disease. In certain embodiments, the adipocyte-related disease is selected from the group consisting of metabolic syndrome, excess body fat (e.g., being overweight, obesity), dyslipidemia, hypercholesterolemia, hypertriglyceridemia, diabetes (e.g., type 2 diabetes), atherosclerosis, vascular disease, coronary artery disease, stroke, cerebrovascular disease, peripheral vascular disease, fatty liver disease, hepatic fibrosis, pancreatitis, cancer (e.g., breast cancer, uterine cancer, colon cancer, colorectal cancer, kidney cancer, esophageal cancer), inflammation or inflammatory disease, depression, and dementia. In certain embodiments, the adipocyte-related disease is selected from the group consisting of metabolic syndrome, diabetes (e.g., type 2 diabetes), liver disease, atherosclerosis, fatty liver disease, hepatic fibrosis, breast cancer, colon cancer, inflammation or inflammatory disease, depression, and dementia.

In a fourth aspect, the invention provides methods, compositions, kits, and systems for treating or preventing dyslipidemia, comprising administering to a subject one or more compounds of Formula (I) or (II), or a pharmaceutically acceptable salt, hydrate, solvate, stereoisomer, polymorph, tautomer, isotopically enriched derivative, or prodrug thereof. In some embodiments, the subject has dyslipidemia but does not suffer from metabolic syndrome.

In certain embodiments, treating dyslipidemia comprises one or more of reducing serum triglycerides, reducing serum total cholesterol, reducing serum lipoprotein (e.g., low density lipoprotein (LDL), very low density lipoprotein (VLDL)), and/or increasing serum high density lipoprotein (HDL). In certain embodiments, treating dyslipidemia comprises reducing the concentration of lipid (e.g., triglycerides, cholesterol, lipoproteins, e.g., low density lipoprotein (LDL), and/or very low density lipoprotein (VLDL)) in the blood of the subject. In certain embodiments, the subject suffers from or is likely to suffer from a disease, disorder, or condition associated with dyslipidemia. In certain embodiments, the subject suffers from or is likely to suffer from a disease, disorder, or condition selected from the group consisting of dyslipidemia, hypercholesterolemia, hypertriglyceridemia, a heritable disorder characterized at least in part by one or more abnormal serum lipid levels (e.g., familial hypercholesterolemia, familial hypertriglyceridemia), excess body fat (e.g., overweight, obesity), metabolic syndrome, vascular disease, atherosclerosis, coronary artery disease, stroke, cerebrovascular disease, peripheral vascular disease, metabolic syndrome, diabetes (e.g., type 2 diabetes), fatty liver disease, hepatic fibrosis, pancreatitis, cancer (e.g., breast cancer, uterine cancer, colon cancer, colorectal cancer, kidney cancer, esophageal cancer), inflammation or inflammatory disease, depression, and dementia.

In a fifth aspect, the invention provides methods, compositions, kits, and systems for treating and/or preventing a diabetic condition, comprising administering to a subject one or more compounds of Formula (I) or (II), or a pharmaceutically acceptable salt, hydrate, solvate, stereoisomer, polymorph, tautomer, isotopically enriched derivative, or prodrug thereof. In some embodiments, the subject has a diabetic condition but does not suffer from metabolic syndrome.

In certain embodiments, treating a diabetic condition comprises reducing serum glucose, reducing glycated hemoglobin levels, reducing serum insulin, increasing insulin sensitivity, improving glucose tolerance (e.g., reducing the glucose levels measured during a glucose tolerance test), reducing a subject's need for another medication (e.g., insulin) to maintain normal blood sugar levels, and/or treating or preventing a diabetic complication.

In certain embodiments, the diabetic subject being treated suffers from or is likely to suffer from a disease, disorder or condition selected from the group consisting of type 2 diabetes mellitus, type 1 diabetes mellitus, prediabetes, hyperglycemia, insulin resistance, hyperinsulinemia, diabetic nephropathy, diabetic retinopathy, diabetic neuropathy, atherosclerosis, coronary artery disease, stroke, myocardial ischemia, myocardial infarction, diabetic myocardial small vessel disease, diabetic gastroparesis, diabetic hearing loss, a diabetic skin disease, a diabetes-related infection, diabetic oral disease (e.g., gingivitis), diabetic acidosis (e.g., diabetic ketoacidosis), nonketotic hyperosmolar state, and diabetic foot ulcer.

For any of the inventive methods or compositions, in certain embodiments, the route of administering is selected from the group consisting of topical (e.g., transdermal), enteral (e.g., oral), and parenteral (e.g., subcutaneous) administration. In certain embodiments, the route of administration is transdermal. In certain embodiments, the compound is administered in a lipophilic excipient. The foregoing aspects and embodiments of the invention may be more fully understood by reference to the following Definitions, Figures, Detailed Description, Examples, and the Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Certain compounds as described herein can comprise one or more asymmetric centers, and thus can exist in various isomeric forms, e.g., enantiomers and/or diastereomers. The compounds provided herein can be in the form of an individual enantiomer, diastereomer or geometric isomer, or can be in the form of a mixture of stereoisomers, including racemic mixtures and mixtures enriched in one or more stereoisomer. In certain embodiments, the compounds as described herein are enantiopure compounds. In certain other embodiments, mixtures of stereoisomers are provided.

Furthermore, certain compounds, as described herein may have one or more double bonds that can exist as either the cis or trans, or the E or Z isomer, unless otherwise indicated. The invention additionally encompasses the compounds as individual isomers substantially free of other isomers, and alternatively, as mixtures of various isomers, e.g., racemic mixtures of E/Z isomers or mixtures enriched in one E/Z isomer.

The terms "enantiomerically enriched," "enantiomerically pure" and "non-racemic," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, more preferably at least 75% by weight, and even more preferably at least 80% by weight. In some embodiments, the enrichment can be much greater than 80% by weight, providing a "substantially enantiomerically enriched," "substantially enantiomerically pure" or a "substantially non-racemic" preparation, which refers to preparations of compositions which have at least 85% by weight of one enantiomer relative to other enantiomer, more preferably at least 90% by weight, and even more preferably at least 95% by weight. In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, alone or as part of another group, "alkyl" refers to a radical of a straight-chain or branched saturated hydrocarbon group having from 1 to 30 carbon atoms ("$C_{1-30}$ alkyl"). In some embodiments, an alkyl group has 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Unless otherwise specified, each instance of an alkyl group is independently unsubstituted ("unsubstituted alkyl") or substituted ("substituted alkyl") are substituted with one or more substituents. In certain embodiments, the alkyl group is an unsubstituted $C_{1-6}$ alkyl (e.g., —$CH_3$). In certain embodiments, the alkyl group is a substituted $C_{1-6}$ alkyl.

As used herein "perhaloalkyl" or "halosubstituted alkyl" as defined herein refers to an alkyl group having from 1 to 10 carbon atoms wherein all of the hydrogen atoms are each independently replaced halogen, e.g., selected from fluoro, bromo, chloro or iodo ("$C_{1-10}$ perhaloalkyl"). In some embodiments, the alkyl moiety has 1 to 6 carbon atoms ("$C_{1-6}$ perhaloalkyl"). In some embodiments, the alkyl moiety has 1 to 5 carbon atoms ("$C_{1-5}$ perhaloalkyl l"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, —$CF_2Cl$ and the like.

As used herein, "alkyloxy" refers to an alkyl group, as defined herein, substituted with an oxygen atom, wherein the point of attachment is the oxygen atom. In certain embodiments, the alkyl group has 1 to 6 carbon atoms ("$C_{1-6}$ alkyloxy"). In some embodiments, the alkyl group has 1 to 4 carbon atoms ("$C_{1-4}$ alkyloxy"). Examples of $C_{1-4}$ alkyloxy groups include methoxy ($C_1$), ethoxy ($C_2$), propoxy ($C_3$), isopropoxy ($C_3$), butoxy ($C_4$), tert-butoxy ($C_5$) and the like. Examples of $C_{1-6}$ alkyloxy groups include the aforementioned $C_{1-4}$ alkyloxy groups as well as pentyloxy ($C_5$), isopentyloxy ($C_5$), neopentyloxy ($C_5$), hexyloxy ($C_6$) and the like. Unless otherwise specified, each instance of the alkyl moiety of the alkyloxy group is independently unsubstituted ("unsubstituted alkyloxy") or substituted ("substituted alkyloxy") with one or more substituents. In certain embodiments, the alkyloxy group is an unsubstituted $C_{1-6}$ alkyloxy. In certain embodiments, the alkyloxy group is a substituted $C_{1-6}$ alkyloxy.

As used herein, "alkylcarboxy" refers to a group of the formula —C(=O)OR$^a$ or —OC(=O)R$^a$, wherein R$^a$ is an alkyl group as defined herein. In certain embodiments, the alkyl of the alkylcarboxy group has 1 to 6 carbon atoms ("$C_{1-6}$ alkylcarboxy"). In some embodiments, the alkyl of the alkylcarboxy group has 1 to 5 carbon atoms ("$C_{1-5}$ alkylcarboxy"). In some embodiments, the alkyl of the alkylcarboxy group has 1 to 4 carbon atoms ("$C_{1-4}$ alkylcarboxy"). In some embodiments, the alkyl of the alkylcarboxy group has 1 to 3 carbon atoms ("$C_{1-3}$ alkylcarboxy"). In some embodiments, the alkyl of the alkylcarboxy group has 1 to 2 carbon atoms ("$C_{1-2}$ alkylcarboxy"). Unless otherwise specified, each instance of the alkyl of the alkylcarboxy group is independently unsubstituted ("unsubstituted alkylcarboxy") or substituted ("substituted alkylcarboxy") with one or more substituents. In certain embodiments, the alkylcarboxy group is an unsubstituted $C_{1-6}$ alkylcarboxy. In certain embodiments, the alkylcarboxy group is a substituted $C_{1-6}$ alkylcarboxy.

As used herein, alone or as part of another group, "alkenyl" refers to a radical of a straight-chain or branched hydrocarbon group having from 2 to 30 carbon atoms and one or more carbon-carbon double bonds ("$C_{2-30}$ alkenyl"). In some embodiments, an alkenyl group has 2 to 10 carbon atoms ("$C_{2-20}$ alkenyl"). In some embodiments, an alkenyl group has 2 to 20 carbon atoms ("$C_{2-10}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-6}$ alkenyl. In certain embodiments, the alkenyl group is a substituted $C_{2-6}$ alkenyl.

As used herein, alone or as part of another group, "alkynyl" refers to a radical of a straight-chain or branched hydrocarbon group having from 2 to 30 carbon atoms and one or more carbon-carbon triple bonds ("$C_{2-30}$ alkynyl"). In some embodiments, an alkynyl group has 2 to 20 carbon atoms ("$C_{2-20}$ alkynyl"). In some embodiments, an alkynyl group has 2 to 10 carbon atoms ("$C_{2-10}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has two carbon atom ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$) and the like. Examples of $C_{2-6}$ alkenyl groups include the aforementioned $C_{2-4}$ alkynyl groups as well as pentynyl ($C_5$), hexynyl ($C_6$) and the like. Unless otherwise specified, each instance of an alkynyl group is independently unsubstituted ("unsubstituted alkynyl") or substituted ("substituted alkynyl") with one or more substituents. In certain embodiments, the alkynyl group is an unsubstituted $C_{2-6}$ alkynyl. In certain embodiments, the alkynyl group is a substituted $C_{2-6}$ alkynyl.

As used herein, a "saturated or unsaturated acyclic hydrocarbon" refers to radical of a saturated or unsaturated, straight-chain or branched, hydrocarbon group having from 1 to 20 carbon atoms and optionally one or more carbon-carbon double or triple bonds. In certain embodiments, the hydrocarbon group is saturated. In some embodiments, the hydrocarbon group is unsaturated, and contains one or more carbon-carbon double or triple bonds. In some embodiments, the hydrocarbon group contains 1-10 carbon atoms. In certain embodiments, the hydrocarbon group contains 1-5 carbon atoms. In some embodiments, the hydrocarbon group contains 1-4 carbon atoms. In some embodiments, the hydrocarbon group contains 1-3 carbon atoms. In some embodiments, the hydrocarbon group contains 1-2 carbon atoms.

As used herein, "carbocyclyl" refers to a radical of a non-aromatic cyclic hydrocarbon group having from 3 to 7 ring carbon atoms ("$C_{3-7}$ carbocyclyl") and zero heteroatoms in the non-aromatic ring system. In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). Exemplary $C_{3-7}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted ("unsubstituted carbocyclyl") or substituted ("substituted carbocyclyl") with 1, 2, 3, 4, or 5 substituents as described herein. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 7 ring carbon atoms ("$C_{3-7}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-7}$ cycloalkyl groups include the aforementioned $C_{3-6}$ cycloalkyl groups as well as cycloheptyl ($C_7$). Unless otherwise specified, each instance of a cycloalkyl group is independently unsubstituted ("unsubstituted cycloalkyl") or substituted ("substituted cycloalkyl") with one or more substituents. In certain embodiments, the cycloalkyl group is an unsubstituted $C_{3-7}$ cycloalkyl. In certain embodiments, the cycloalkyl group is a substituted $C_{3-7}$ cycloalkyl.

As used herein, alone or as part of another group, "heterocyclyl" refers to a radical of a 3- to 8-membered non-aromatic ring system having ring carbon atoms and 1 to 4 ring heteroatoms, wherein each heteroatom is independently selected from nitrogen, oxygen and sulfur ("3-8 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system.

In some embodiments, a heterocyclyl group is a 5-8 membered non-aromatic ring system having ring carbon atoms and 1-4 ring heteroatoms, wherein each heteroatom is independently selected from nitrogen, oxygen and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen and sulfur ("5-6 membered heterocyclyl"). In some embodiments, the 5-6 membered heterocyclyl has 1-3 ring heteroatoms selected from nitrogen, oxygen and sulfur. In some embodiments, the 5-6 membered heterocyclyl has 1-2 ring heteroatoms selected from nitrogen, oxygen and sulfur. In some embodiments, the 5-6 membered heterocyclyl has 1 ring heteroatom selected from nitrogen, oxygen and sulfur. Exemplary 3-membered heterocylyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Unless otherwise specified, each instance of heterocyclyl is independently unsubstituted ("unsubstituted heterocyclyl") or substituted ("substituted heterocyclyl") with one or more substituents. In certain embodiments, the heterocyclyl group is an unsubstituted 3-8 membered heterocyclyl. In certain embodiments, the heterocyclyl group is a substituted 3-8 membered heterocyclyl.

As used herein, alone or as part of another group, "aryl" refers to a radical of a monocyclic or polycyclic (e.g., bicyclic or tricyclic) 4n+2 aromatic ring system having 6-10 ring carbon atoms and zero heteroatoms provided in the aromatic ring system ("$C_{6-10}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). "Aryl" also includes ring systems wherein the aryl ring, as defined above, is fused with one or more cycloalkyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents as described herein. In certain embodiments, the aryl group is an unsubstituted $C_{6-10}$ aryl. In certain embodiments, the aryl group is a substituted $C_{6-10}$ aryl.

As used herein, alone or as part of another group, "heteroaryl" refers to a radical of a 5-14 membered monocyclic or polycyclic (e.g., bicyclic) 4n+2 aromatic ring system having 4-10 ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocycyl or heterocycyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or on the heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen and sulfur ("5-6 membered heteroaryl"). In some embodiments, the 5-6 membered heteroaryl has 1-3 ring heteroatoms selected from nitrogen, oxygen and sulfur. In some embodiments, the 5-6 membered heteroaryl has 1-2 ring heteroatoms selected from nitrogen, oxygen and sulfur. In some embodiments, the 5-6 membered heteroaryl has 1 ring heteroatom selected from nitrogen, oxygen and sulfur. Exemplary 5-membered heteroaryls containing 1 heteroatom include, without limitation, pyrrolyl, furanyl and thiophenyl. Exemplary 5-membered heteroaryls containing 2 heteroatoms include, without limitation, imidazolyl, pyrazolyl, oxazolyl, isoxazolyl, thiazolyl, and isothiazolyl. Exemplary 5-membered heteroaryls containing 3 heteroatoms include, without limitation, triazolyl, oxadiazolyl, thiadiazolyl. Exemplary 5-membered heteroaryls containing 4 heteroatoms include, without limitation, tetrazolyl. Exemplary 6-membered heteroaryls containing 1 heteroatom include, without limitation, pyridinyl. Exemplary 6-membered heteroaryls containing 2 heteroatoms include, without limitation, pyridazinyl, pyrimidinyl and pyrazinyl. Exemplary 6-membered heteroaryls containing 3 or 4 heteroatoms include, without limitation, triazinyl and tetrazinyl, respectively. Exemplary 7 membered heteroaryls containing 1 heteroatom include, without limitation, azepinyl, oxepinyl and thiepinyl. Exemplary 5,6-bicyclic heteroaryls include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryls include, without limitation, naphthyridinyl, pteridinyl, quinolinyl, isoquinolinyl, cinnolinyl, quinoxalinyl, phthalazinyl and quinazolinyl. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-10 membered heteroaryl. In certain embodiments, the heteroaryl group is a substituted 5-10 membered heteroaryl.

Alkyl, alkenyl, alkynyl, carbocyclyl, heterocyclyl, aryl and heteroaryl, referred to without the suffix "-ene," describe a monoradical of alkyl, alkenyl, alkynyl, carbocyclyl, heterocyclyl, aryl, or heteroaryl, respectively, and as defined herein, wherein the monoradical is attached to another group by only one single bond. Groups referred to with the suffix "-ene", such as alkylene, alkenylene, alkynylene, carbocyclylene, heterocyclylene, arylene and heteroarylene groups, describe a diradical of alkyl, alkenyl, alkynyl, carbocyclyl, heterocyclyl, aryl, or heteroaryl, respectively, and as defined herein, wherein the diradical is attached to one or two groups by two single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom etc.) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group (e.g., 1, 2, 3, 4 or 5 positions), and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —SC(=O)OR$^{aa}$, SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl, or two R$^{aa}$ groups are joined to form a 3-8 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl, or two R$^{bb}$ groups are joined to form a 3-8 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl, or two R$^{cc}$ groups are joined to form a 3-8 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl, or two R$^{ff}$ groups are joined to form a 3-8 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_1$— alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_1$— alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_1$— alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_1$— alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl; or two geminal R$^{gg}$ substituents can be joined to form =O or =S.

As used herein, the term "halo" or "halogen" refers to fluorine (fluoro, —F), chlorine (chloro, —Cl), bromine (bromo, —Br), or iodine (iodo, —I).

As used herein, "nitro" refers to the group —NO$_2$.

As used herein, "oxo" refers to the group =O.

As used herein, "hydroxyl" or "hydroxy" refers to the group —OH. The term "substituted hydroxyl" or "substituted hydroxy," by extension, refers to a hydroxyl group wherein the oxygen atom is substituted with a group other than hydrogen, e.g., selected from —OR$^{aa}$, —ON(R$^{bb}$)$_2$, —OC(=O) R$^{aa}$, —OC(=O)SR$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N (R$^{bb}$)$_2$, —OS(=O)R$^{aa}$, —OSO$_2$R$^{aa}$, —OSi(R$^{aa}$)$_3$, —OP (R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O) (NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. As used herein, the term "substituted amino" refers to a monosubstituted, disubstituted, or trisubstituted amino group, as defined herein.

As used herein, the term "monosubstituted amino" refers to an amino group substituted with one hydrogen and one group other than hydrogen, and includes groups selected from —NH(R$^{bb}$), —NHC(=O)R$^{aa}$, —NHCO$_2$R$^{aa}$, —NHC(=O) N(R$^{bb}$)$_2$, —NHC(=NR$^{bb}$)N(R$^{bb}$)$_2$, —NHSO$_2$R$^{aa}$, —NHP (=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group substituted with two groups other than hydrogen, and includes groups selected from —N(R$^{bb}$)$_2$, —NR$^{bb}$C (=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P (=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O) N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O) (R$^{aa}$)$_2$, —P(=O)$_2$N(R$^{cc}$)$_2$, —P(=O)(NR$^{cc}$)$_2$, C$_{1-6}$ alkyl, C$_{2-6}$ alkenyl, C$_{2-6}$ alkynyl, C$_{3-7}$ carbocyclyl, 3-8 membered heterocyclyl, C$_{6-10}$ aryl, and 5-10 membered heteroaryl, or two R$^{cc}$ groups attached to an N atom are joined to form a 3-8 membered heterocyclyl or 5-10 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an "amino protecting group". Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$— SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on the oxygen atom is an "oxygen protecting group". Oxygen protecting groups include, but are not limited to —R$^{aa}$, —N(R$^{bb}$)$_2$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O) (OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy) ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3 methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl) methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), isobutyl carbonate, vinyl carbonate, allyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, N,N,N',N'-tetramethylphosphorodiamidate, N-phenylcarbamate, dimethylphosphinothioyl, 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl) ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino) ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

These and other exemplary substituents are described in more detail in the Detailed Description, the Examples and in the Claims. The invention is not intended to be limited in any manner by the above exemplary listing of substituents.

Other Definitions

As used herein, the terms "salt", "acceptable salt", or "pharmaceutically acceptable salt" refer to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "prodrug" means a biologically active derivative of a compound that can hydrolyze, oxidize, or otherwise react under biological conditions (in vitro or in vivo) to provide the pharmacologically active compound. In this instance, the "prodrug" is a compound administered to a subject, and the pharmacologically active compound is the "active metabolite thereof." In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from across the skin, or it may enhance drug stability for long-term storage.

"Metabolic syndrome" is a combination of medical disorders that, when occurring together, increases the risk of developing cardiovascular disease and diabetes. A recent joint scientific statement (Alberti, supra) requires the presence at least 3 of the following 5 findings: elevated waist circumference (definition varies by country), elevated triglycerides (greater than or equal to 150 mg/dL), reduced HDL (under 40 mg/dL in males or under 50 mg/dL in females), elevated blood pressure (systolic greater than or equal to 130 mm and/or diastolic greater than or equal to 85 mm Hg), and elevated fasting glucose (greater than or equal to 100 mg/dL). Principal disorders associated with or used in the diagnosis of metabolic syndrome include, but are not limited to, obesity, dyslipidemia, and diabetic conditions, and conditions associated with these disorders, such as elevated glucose levels and hypertension.

As used herein, an "individual" or "subject" to which administration is contemplated includes, but is not limited to, humans (i.e., a male or female of any age group, e.g., a pediatric subject (e.g., child, adolescent) or adult subject (e.g., young adult, middle-aged adult or senior adult)), other primates (e.g., cynomolgus monkeys, rhesus monkeys) and commercially relevant mammals such as cattle, pigs, horses, sheep, goats, cats, and/or dogs. In any aspect and/or embodiment of the invention, the subject is a human subject.

As used herein, and unless otherwise specified, a "therapeutically effective amount" "an amount sufficient" or "sufficient amount" of a compound means the level, amount or concentration of the compound needed to treat or prevent metabolic syndrome and/or a disorder associated with metabolic syndrome, or to treat or prevent a particular parameter (e.g., body weight, body fat, adipocytes, lipid or glucose concentrations in the blood) in the body of a subject, without causing significant negative or adverse side effects to body or the treated tissue. The term "therapeutically effective amount" can encompass an amount that improves overall therapy, reduces or avoids symptoms or causes of metabolic syndrome and/or a disorder associated with metabolic syndrome, or enhances the therapeutic efficacy of another therapeutically active agent.

As used herein, a "therapeutically effective concentration" refers to the concentration (e.g., μg/mL) of a compound, or active metabolite thereof, in the blood of a subject within the therapeutic range. The "therapeutic range" refers to the concentration above the minimal effective concentration (i.e., the required level of a compound needed for therapeutic effect) and below the minimum effective concentration for adverse effects (i.e., the toxic level of the compound).

As used herein, the terms "reduce", "reduction", "reducing", "lower", or "lowering" means to diminish or lessen the volume, size, mass, bulk, density, amount, and/or quantity of a substance (e.g., body weight, body fat, adipocyte size, adipocyte number, adipose tissue volume, adipose tissue thickness, lipid concentration, glucose concentration) in the body of a subject.

As used herein, the term "eliminate" means to completely remove any unwanted or undesired volume, size, mass, bulk, density, amount, and/or quantity of a substance (e.g., excess body weight, excess body fat, excess adipocytes, excess adipose tissue, elevated lipid concentration, elevated glucose concentration) in the body of a subject.

As used herein, "suffer", "suffers" or "suffering from" refers to a subject having metabolic syndrome and/or a disorder associated with metabolic syndrome. As used herein, "likely to suffer" refers to a subject who has not been diagnosed with metabolic syndrome and/or a disorder associated with metabolic syndrome by a medical practitioner, but has a predisposition (e.g., genetic and/or physiologic predisposition), or exhibits signs or symptoms of metabolic syndrome and/or a disorder associated with metabolic syndrome.

As used herein, and unless otherwise specified, the terms "treat," "treating" and "treatment" contemplate an action that occurs while a subject is suffering from metabolic syndrome and/or a disorder associated with metabolic syndrome, which reduces the severity of the metabolic syndrome and/or a disorder associated with metabolic syndrome, or retards or slows the progression of metabolic syndrome and/or a disorder associated with metabolic syndrome.

As used herein, unless otherwise specified, the terms "prevent," "preventing" and "prevention" contemplate an action that occurs before a subject begins to suffer from metabolic syndrome and/or a disorder associated with metabolic syndrome, which inhibits or reduces the severity of the metabolic syndrome and/or a disorder associated with metabolic syndrome.

BRIEF DESCRIPTION OF THE DRAWINGS

FIG. 1 depicts a randomized, controlled, repeat-dose, 4-week trial conducted on (db−/db−) mice, which are defective for the leptin receptor (Jackson Laboratories). These mice are genetically obese, dyslipidemic, and diabetic. Mice were obtained from Jackson Laboratories and acclimated to the facility. At about 5 weeks of age, mice were prospectively randomized into groups and assigned to the treatment conditions shown in FIG. 1. Topical treatments were applied in a thin film to the right flank skin without occlusive dressings; subcutaneous injections were also administered to the right flank. Mice were observed for condition and weighed daily. They were housed in the same room, in 11 cages according to group, and fed ad libitum. Skin tissue was sampled and serum lipids tested on day 28. Tissue was fixed in formalin and stained with hematoxylin and eosin.

FIG. 2 shows mean weight gain of the mice treated in FIG. 1 for days 0 to 28, by group. Animals treated with vehicle only (Groups 1 and 2) showed an expected amount of weight gain for the strain (normative data, Jackson Laboratories). Transdermal bimatoprost isopropyl ester (BIE) and bimatoprost free acid (BFA) reduced weight gain significantly and in a dose-dependent manner, but topical bimatoprost did not. Subcutaneous BIE, subcutaneous BFA, and intraperitoneal BFA had no significant effect on weight gain.

FIG. 4 shows mean, unfasted, serum lipid concentrations for each group (day 28), expressed as a percent reduction relative to control (Group 1).

FIG. 6 depicts a controlled, repeat-dose, 4-week, dose-ranging study of latanoprost transdermal cream was conducted in Zucker Diabetic Fatty (ZDF) rats (ZDF-Lepr$^{fa}$/Crl), which are defective for the leptin receptor, obese, hyperlipidemic, and diabetic. Male ZDF rats, approximately 8 weeks old, were obtained from Jackson Laboratories and acclimated to the facility. They were prospectively assigned to treatment conditions shown in FIG. 6. There were 3 animals per treatment arm. Test articles were applied in a thin film to the right flank without occlusive dressings, at 0.3 ml daily for 28 days. Rats were fed ad libitum and housed in the same room in 4 cages according to group. They were observed for condition and weighed daily. Food consumption was measured by residual weight of chow. Animals were fasted overnight prior to day 29, and Oral Glucose Tolerance Tests were conducted on day 29 (1 g glucose per kg body weight). Skin tissue and serum chemistries were collected at day 29.

FIG. 7 depicts shows mean weight gain, by group, for days 0 to 29. Compared to vehicle, topical latanoprost 0.5%, 0.05%, 0.005% caused a dose-dependent reductions in weight gain, which were statistically significant for the 0.5% and 0.05% concentrations.

FIG. 11 indicates the serum glucose Area Under the Curve from 15 to 120 minutes post-glucose load ($AUC_{15\text{-}120}$) was 12% and 26% lower in animals treated with latanoprost 0.05% and 0.5%, respectively, compared to vehicle-treated animals. There was no effect on oral glucose tolerance with latanoprost 0.005%.

FIG. 12 compares various topical doses of latanoprost in mouse, rat, and human, with respect to projected systemic dose.

DETAILED DESCRIPTION OF CERTAIN EMBODIMENTS OF THE INVENTION

Figure 3:
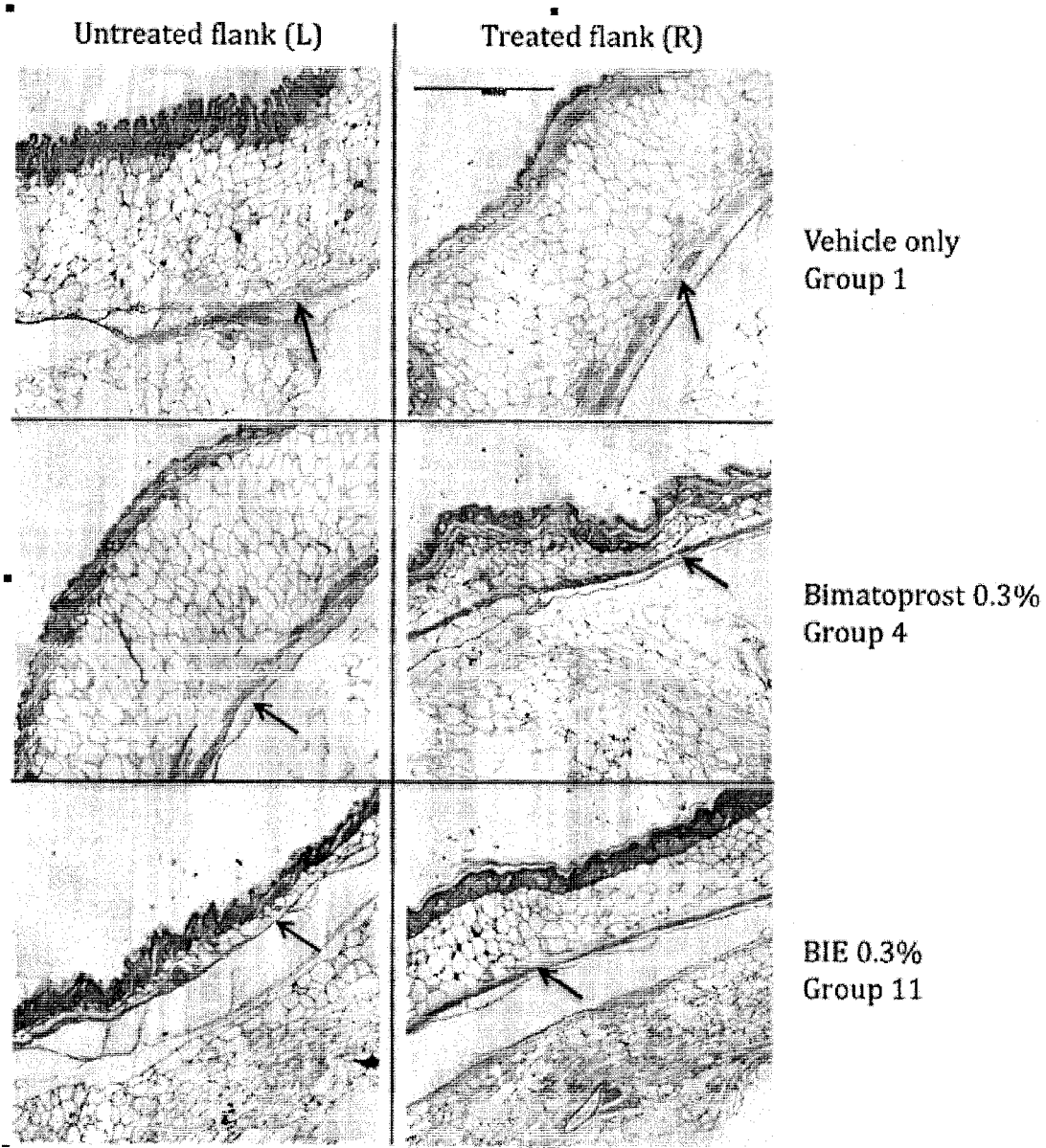
FIG. 3 shows representative histologic sections of skin and subcutaneous fat from untreated (left) and treated (right) flanks of animals assigned to vehicle only (Group 1), topical bimatoprost 0.3% (Group 4), and topical BIE 0.3% (Group 11). All sections are shown at the same magnification (scale bar at top right=640 microns). The surface of the skin is oriented toward the top and left of each panel. Arrows in each section denote the panniculus carnosus, an anatomic layer that separates the first layer of subdermal fat from deeper, subpannicular fat (separation artifact is commonly seen deep to the panniculus and is not an in vivo process).

The present invention describes uses of certain prostaglandins, i.e., one or more compounds of compounds of Formula (I) or (II), or a pharmaceutically acceptable salt, hydrate, solvate, stereoisomer, polymorph, tautomer, isotopically enriched derivative, or prodrug thereof, as described herein, to reduce, or eliminate altogether, body fat, for example, adipose tissue and/or adipocytes, in a subject, for example, a human. The invention further relates to uses of said compounds to reduce the concentration of lipid (e.g., triglycerides, cholesterol, lipoproteins (e.g., low density lipoprotein and very low density lipoprotein)), and/or increase HDL, in the blood of a subject.

Previously members of the genus of F-series prostaglandins were recognized as hypotensive agents. For example, see U.S. Pat. Nos. 5,688,819 and 6,403,649, incorporated herein by reference. These compounds were shown to effect vasodilation and thereby were predicted to relieve symptoms of various diseases associated with increased blood pressure, including acute myocardial infarction, vascular thrombosis, hypertension, pulmonary hypertension, ischemic heart disease, congestive heat failure, and angina pectoris. These compounds were also shown to be effective ocular hypotensive agents useful for the treatment of elevated intraocular pressure, for example, glaucoma.

Previous studies have shown that the use of bimatoprost eyedrops for the treatment of glaucoma does decrease intraocular pressure, but also induces unwanted side effects, which were eventually understood to be due to the atrophy of the fat normally present around the eye, i.e., the orbital fat. The use of bimatoprost to reduce unwanted fat by local administration was disclosed in U.S. Pat. No. 7,666,912, incorporated herein by reference.

The present invention arises in part from a new finding that administration of certain F-series prostaglandins to obese, dyslipidemic, and/or diabetic animals has beneficial effects on disorders associated with metabolic syndromes in these animals. The observed effects include reduced obesity, reduced weight gain, reduce serum triglycerides, reduced serum LDL, increased serum HDL, reduced serum glucose, and/or improved glucose tolerance.

The present invention also arises from the observation that systemic administration of certain F-series prostaglandins to obese animals reduces weight and/or weight gain in those animals.

The present invention also arises from the experimental identification of certain preferred species from among the genus of F-series prostaglandins for the purposes of the invention.

Prior to this work, it was envisioned that bimatoprost, when non-systemically and locally administered topically, subcutaneously, intramuscularly, or intralesionally at certain concentrations, e.g., 0.003%, 0.03%, or 0.3%, would locally reduce fat in a subject at the site of administration. See, e.g., the Examples of U.S. Pat. No. 7,666,912, incorporated herein by reference. In a human, an overall dose of 30 mg/m$^2$/d (about 57 mg) using 0.3% ointment would involve application of about 20 g of ointment daily. The inventor has now discovered that while 0.3% topical bimatoprost (at an overall dose of about 30 mg/m$^2$/d) locally reduces subcutaneous fat in a subject, the isopropyl ester and free acid of bimatoprost are significantly more effective in reducing subcutaneous fat. The inventor has further observed that while topical administration of bimatoprost locally reduces fat, topical administration of the isopropyl ester and free acid of bimatoprost reduces fat not only locally but also throughout the body, indicative of a systemic effect. In fact, topical administration of 0.3% bimatoprost isopropyl ester (at an overall dose of about 30 mg/m$^2$/d) shows a significant systemic effect in reduction of serum lipids in the bloodstream of a subject, while topical administration of bimatoprost shows no systemic effect. See Example 1 below. The findings and observations disclosed herein are indeed surprising and unexpected, especially considering U.S. Pat. No. 7,666,912 dissuades from systemically administering such compounds.

Furthermore, the inventor discovered that, unlike transdermal administration of bimatoprost ester or the free acid, neither subcutaneous nor intraperitoneal administration of bimatoprost ester or free acid had any significant effect on fat reduction. Without wishing to be bound by any particular theory, the inventor postulates that even if the compound is eliminated rapidly from the bloodstream (e.g., latanoprost has a serum elimination half-life of about 17 minutes), transdermal administration may provide a depot effect whereby a compound applied to the skin may result in slow release of the active ingredient into the bloodstream, and thereby result in a more sustained therapeutically effective concentration in the bloodstream. Furthermore, without wishing to be bound by theory, a similar effect can be obtained, for example, with a time release formulation, such as a controlled, extended, or sustained release formulation for oral, subcutaneous, intraperitoneal administration, or a continuous intravenous infusion, and the like.

Without wishing to be bound by any particular theory, reduction in fat as a function of administration of the compounds disclosed herein may include reducing the number of fat cells (adipocytes), reducing the volume of one or more fat cells (adipocytes), reducing maturation of one or more fat cells (adipocytes), and/or dedifferentiating one or more fat cells (adipocytes). Such effects may be mediated through prostaglandin or prostaglandin-like receptors, and compounds according to the invention may exert their effects as herein disclosed by acting as agonists at these receptors. Because adipocytes have been specifically implicated in a wide array of human diseases, the present invention suggests a means for treating and/or preventing adipocyte-related diseases, such as, but not limited to, metabolic syndrome, diabetes (e.g., type 2 diabetes), liver disease, atherosclerosis, fatty liver, hepatic fibrosis, inflammation or inflammatory disease, depression, and dementia. The invention can be used to reduce adipocytes by administration of one or more of the compounds described herein, e.g., one or more compounds of the Formula (I) or (II).

Thus, in one aspect, the present invention is directed to the use of certain prostaglandins, e.g., one or more compounds of the Formula (I) or (II), for treating and/or preventing metabolic syndrome or a disorder associated with metabolic syndrome in the body of a subject, by systemically administering the compound to the subject, e.g., at a concentration sufficient to produce a systemic effect in the bloodstream of a subject. More specifically a condition such as obesity, dyslipidemia, and/or a diabetic condition may be treated and/or prevented by administering to a subject a compound described herein. Furthermore, diseases and/or medical outcomes associated with the metabolic syndrome, obesity, dyslipidemia, and/or a diabetic condition may be treated and/or prevented by administering to a subject a compound described herein.

The F-series prostaglandins disclosed herein are considered to be members of the class of prostaglandin F2α receptor agonists, which are known to be in vitro inhibitors of adipocyte differentiation and survival. See, e.g., Serrero et al. (1992) *Biochem. Biophys. Res. Commun.* 183:438-442; Lepak et al. (1993) *Prostaglandins* 46:511-517; Serrero et al. (1995) *Biochem. Biophys. Res. Commun.* 212:1125-1132; and Lepak et al. (1995) *Endocrinology* 136:3222-3229. Accordingly, without wishing to be bound by any particular theory, the fat-reducing properties of these compounds may relate to its agonism of prostaglandin or prostaglandin-like receptors, in particular the prostaglandin FP receptor (PTGFR).

Compounds for Use in the Present Invention

The present invention relates to uses of a compound of Formula (I) or (II), or a pharmaceutically acceptable salt, hydrate, solvate, stereoisomer, polymorph, tautomer, isotopically enriched derivative, or prodrug thereof.

In certain embodiments, the compound useful in the present invention is of Formula (I) or (II):

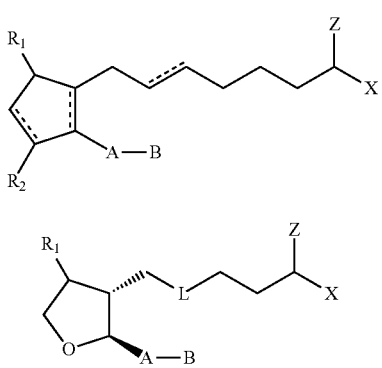

or a pharmaceutically acceptable salt, hydrate, solvate, stereoisomer, polymorph, tautomer, isotopically enriched derivative, or prodrug thereof;
wherein:
L is a group of the formula

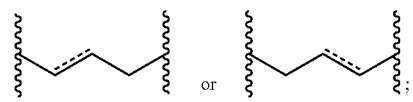

each instance of ===== independently represents a single bond or a double bond which can be in the cis or trans configuration;

A is optionally substituted $C_{1-10}$alkylene, optionally substituted $C_{2-10}$alkenylene, or optionally substituted $C_{2-10}$ alkynylene, wherein the alkylene, alkenylene, or alkynylene group is optionally interrupted by one or more —O— or —S— groups;

B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl;

X is —$OR_4$, —$SR_4$, or —$N(R_4)_2$, wherein each instance of $R_4$ is independently hydrogen, optionally substituted $C_{1-30}$alkyl, optionally substituted $C_{2-30}$alkenyl, optionally substituted $C_{2-30}$alkynyl, —C(=O)$R_5$, or —C(=O)O$R_5$, wherein $R_5$ is optionally substituted $C_{1-30}$alkyl, optionally substituted $C_{2-30}$alkenyl, or optionally substituted $C_{2-30}$alkynyl, or two $R_4$ groups are joined to form an optionally substituted 3-8-membered-heterocyclyl or optionally substituted 5-14-membered-heteroaryl ring;

Z is =O, =S, or =$NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms;

with regard to the compound of Formula (I), one of $R_1$ and $R_2$ is =O, —OH, or a —O(CO)$R_6$ group and the other one is —OH or —O(CO)$R_6$, or $R_1$ is =O and $R_2$ is H, wherein $R_6$ is a an optionally substituted $C_{1-20}$alkyl, optionally substituted $C_{2-20}$alkenyl, optionally substituted $C_{2-20}$ alkynyl, or —(CH$_2$)$_m$$R_7$ wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl; and with regard to the compound of Formula (II), $R_1$ is =O, —OH, or —O(CO)$R_6$, wherein $R_6$ is a an optionally substituted $C_{1-20}$alkyl, optionally substituted $C_{2-20}$alkenyl, optionally substituted $C_{2-20}$ alkynyl, or —(CH$_2$)$_m$$R_7$ wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$-aryl, or optionally substituted 5-14-membered-heteroaryl.

In certain embodiments, the compound is not bimatoprost. In certain embodiments, the compound is not latanoprost. In certain embodiments, the compound is not travoprost.

In certain embodiments, the endocyclic dotted lines of Formula (I) (i.e., depicted in the 5-membered ring) each represent a single bond.

For example, in certain embodiments, wherein the endocyclic dotted lines of Formula (I) each represent a single bond, provided is a compound having any one of the following stereochemistry:

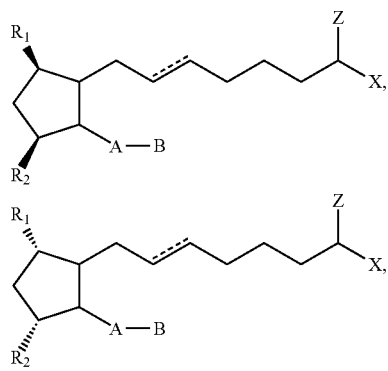

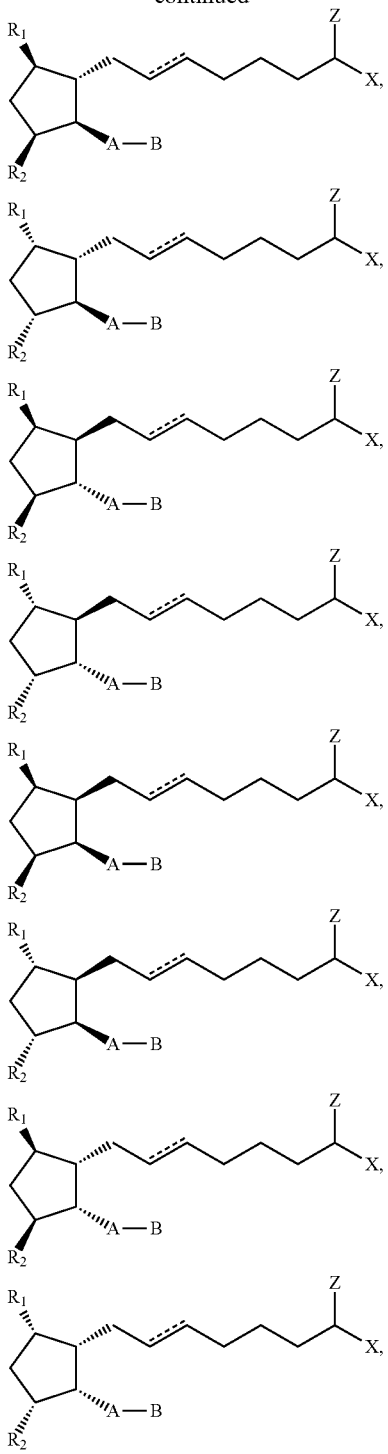

pharmaceutically acceptable salt, hydrate, solvate, stereoisomer, polymorph, tautomer, isotopically enriched derivative, or prodrug thereof, wherein =====, $R_1$, $R_2$, A, B, Z and X are as defined herein.

In certain embodiments, the exocyclic dotted line ===== (i.e., depicted outside of the 5-membered ring) of Formula (I) or (II) or a subset thereof represents a double bond in the cis or trans configuration. In certain embodiments, the exocyclic dotted line ===== represents a double bond in the cis configuration.

In certain embodiments, each instance of ===== independently represents a single bond or a double bond which can be in the cis or trans configuration.

As generally defined above, one of $R_1$ and $R_2$ is =O, —OH, or a —O(CO)$R_6$ group and the other one is —OH or —O(CO)$R_6$, or $R_1$ is =O and $R_2$ is H, wherein $R_6$ is an optionally substituted $C_{1-20}$alkyl, optionally substituted $C_{2-20}$alkenyl, optionally substituted $C_{2-20}$ alkynyl, or —(CH$_2$)$_m$R$_7$ wherein m is 0 or an integer of between 1-10, inclusive, and $R_7$ is optionally substituted $C_{3-7}$carbocyclyl, optionally substituted 3-8-membered-heterocyclyl, optionally substituted $C_{6-10}$aryl, or optionally substituted 5-14-membered-heteroaryl.

In certain embodiments, $R_1$ is =O and $R_2$ is H.

In certain embodiments, one of $R_1$ and $R_2$ is —OH, substituted hydroxyl, or —O(CO)$R_3$, and the other one is —OH, substituted hydroxyl, or —O(CO)$R_6$.

In certain embodiments, both $R_1$ and $R_2$ are —OH.

As generally defined above, A is optionally substituted $C_{1-10}$alkylene, optionally substituted $C_{2-10}$alkenylene or optionally substituted $C_{2-10}$alkynylene, wherein the alkylene, alkenylene, or alkynylene group is optionally interrupted by one or more —O— or —S— groups. As used herein, "interrupted by" refers to an alkylene, alkenylene, or alkynylene which may optionally be flanked by an —O— or —S— group and/or an —O— or —S— group is included within the carbon chain.

In certain embodiments, A is optionally substituted $C_{1-10}$alkylene, optionally substituted $C_{2-10}$alkenylene or optionally substituted $C_{2-10}$alkynylene, wherein the alkylene, alkenylene, or alkynylene group is optionally interrupted by one —O— group.

In certain embodiments, A is optionally substituted $C_{4-6}$alkylene, optionally substituted $C_{4-6}$alkenylene or optionally substituted $C_{4-6}$alkynylene, wherein the alkylene, alkenylene, or alkynylene group is optionally interrupted by one —O— group.

In certain embodiments, A is optionally substituted $C_{4-6}$alkylene optionally interrupted by one —O— group. In certain embodiments, A is optionally substituted $C_{4-6}$alkenylene optionally interrupted by one —O— group. In certain embodiments, A is optionally substituted $C_{4-6}$alkynylene optionally interrupted by one —O— group.

In certain embodiments, A is optionally substituted $C_{1-10}$alkylene, optionally substituted $C_{2-10}$alkenylene or optionally substituted $C_{2-10}$alkynylene, wherein the alkylene, alkenylene, or alkynylene group is optionally interrupted by one —S— group.

In certain embodiments, A is optionally substituted $C_{4-6}$alkylene, optionally substituted $C_{4-6}$alkenylene or optionally substituted $C_{4-6}$alkynylene, wherein the alkylene, alkenylene, or alkynylene group is optionally interrupted by one —S— group.

In certain embodiments, A is optionally substituted $C_{4-6}$alkylene optionally interrupted by one —S— group. In certain embodiments, A is optionally substituted $C_{4-6}$alkenylene optionally interrupted by one —S— group. In certain embodiments, A is optionally substituted $C_{4-6}$alkynylene optionally interrupted by one —S— group.

In certain embodiments, A is substituted with one or more groups selected from the group consisting of halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, and optionally substituted 5-14-membered-heteroaryl.

In certain embodiments, A is substituted with =O.

In certain embodiments, A is substituted with —OC(=O)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$, wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl.

In certain embodiments, A is substituted with —OH or substituted hydroxyl.

In certain embodiments, A is substituted with substituted hydroxyl.

In certain embodiments, A is substituted with —OH.

In certain embodiments, A is substituted with halogen, e.g., —F.

In certain embodiments, A is a group of the formula (i), (ii), (iii), (iv), (v), or (vi):

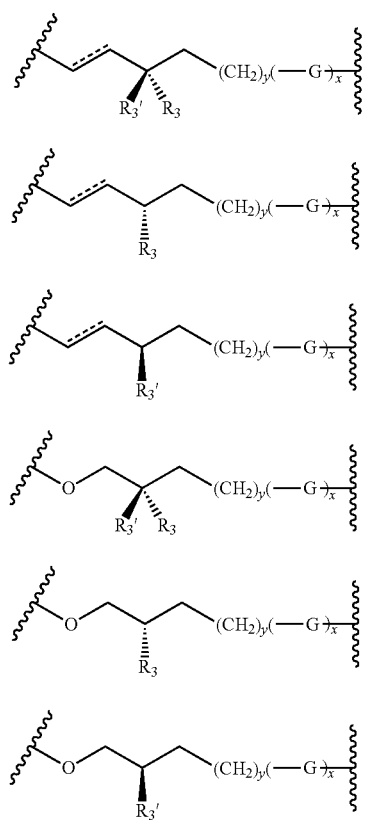

wherein each instance of ===== independently represents a single bond or a double bond which can be in the cis or trans configuration;

each instance of $R_3$ and $R_3$' is hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3$' are joined to form =O;

G is —O— or —S—;

y is 0, 1, or 2; and x is 0 or 1.

In certain embodiments, G is —O—. In certain embodiments, G is —S—.

In certain embodiments, ===== of formula (i), (ii), or (iii) represents a double bond in the cis configuration.

In certain embodiments, ===== of formula (i), (ii), or (iii) represents a double bond in the trans configuration.

In certain embodiments, the group of the formula (i) is of the formula:

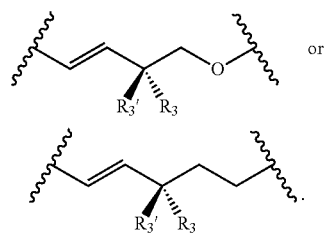

In certain embodiments, the group of the formula (ii) is of the formula:

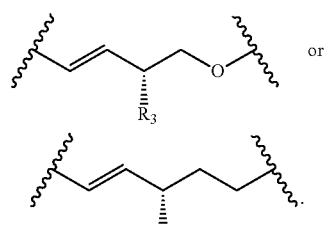

In certain embodiments, ===== formula (i), (ii), or (iii) represents a single bond.

In certain embodiments, the group of the formula (i) is of the formula:

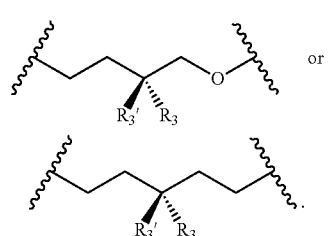

In certain embodiments, the group of the formula (ii) is of the formula:

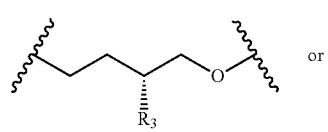

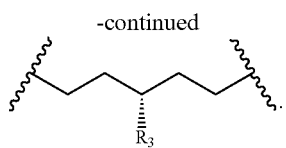

As generally defined above, each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl; or $R_3$ and $R_3'$ are joined to form =O.

In certain embodiments, $R_3$ is hydrogen. In certain embodiments, $R_3'$ is hydrogen. In certain embodiments, $R_3$ is hydrogen and $R_3'$ is a non-hydrogen group. In certain embodiments, $R_3'$ is hydrogen and $R_3$ is a non-hydrogen group. In certain embodiments, however, neither $R_3$ nor $R_3'$ is hydrogen.

In certain embodiments, $R_3$ and $R_3'$ are joined to form =O.

In certain embodiments, $R_3$ and $R_3'$ are the same group. In certain embodiments, $R_3$ and $R_3'$ are different groups.

In certain embodiments, $R_3$ is —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl. In certain embodiments, $R_3$ is —O(CO)$R_8$. In certain embodiments, $R_3$ is —OH or substituted hydroxyl. In certain embodiments, $R_3$ is substituted hydroxyl. In certain embodiments, $R_3$ is —OH.

In certain embodiments, $R_3'$ is —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl. In certain embodiments, $R_3'$ is —O(CO)$R_8$. In certain embodiments, $R_3'$ is —OH or substituted hydroxyl. In certain embodiments, $R_3'$ is substituted hydroxyl. In certain embodiments, $R_3'$ is —OH.

In certain embodiments, $R_3$ is halogen, e.g., selected from fluoro, chloro, bromo, and iodo. In certain embodiments, $R_3'$ is halogen, e.g., selected from fluoro, chloro, bromo, and iodo. In certain embodiments, $R_3$ is halogen and $R_3'$ is halogen, e.g., each independently selected from fluoro, chloro, bromo, and iodo. In certain embodiments, both $R_3$ and $R_3'$ are fluoro.

In certain embodiments, y is 0 and x is 1. In certain embodiments, y is 0 and x is 0. In certain embodiments, y is 1 and x is 1. In certain embodiments, y is 1 and x is 0. In certain embodiments, y is 2 and x is 0. In certain embodiments, y is 2 and x is 1.

As defined generally above, B is hydrogen, optionally substituted $C_{3-7}$carbocyclyl, optionally substituted 3-8-membered-heterocyclyl, optionally substituted 5-14-membered-heteroaryl, optionally substituted $C_{6-10}$aryl, optionally substituted $C_{1-30}$alkyl, optionally substituted $C_{2-30}$alkenyl, or optionally substituted $C_{2-30}$alkynyl.

In certain embodiments, B is hydrogen.

In certain embodiments, B is optionally substituted $C_{1-30}$alkyl. In certain embodiments, B is optionally substituted $C_{2-30}$alkenyl. In certain embodiments, B is optionally substituted $C_{2-30}$alkynyl.

In certain embodiments, B is optionally substituted $C_{3-7}$carbocyclyl, e.g., optionally substituted cyclohexyl. In certain embodiments, B is optionally substituted 3-8-membered-heterocyclyl. In certain embodiments, B is optionally substituted 5-14-membered-heteroaryl. In certain embodiments, B is optionally substituted $C_{6-10}$aryl. In certain embodiments, B is optionally substituted $C_6$aryl (i.e., phenyl). In certain embodiments, B is optionally substituted $C_{10}$aryl (i.e., napthyl).

For example, in certain embodiments, B is an optionally substituted phenyl of the formula (viii): (viii)

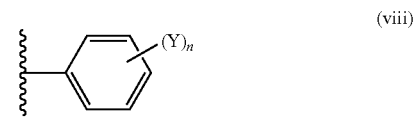

wherein:

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino; and n is 0 or an integer of from 1 to 5, inclusive.

In certain embodiments, n is 0 or an integer from 1 to 3, inclusive. In certain embodiments, n is 0 or an integer from 1 to 2, inclusive. In certain embodiments, n is 0. In certain embodiments, n is 1. In certain embodiments, n is 2. In certain embodiments, n is 3.

For example, in certain embodiments, wherein n is 1, the group of the formula (viii) is of the formula:

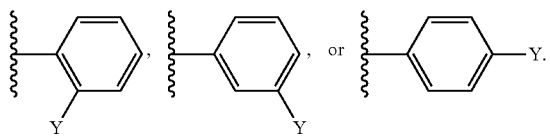

In certain embodiments, wherein n is 2, the group of the formula (viii) is of the formula:

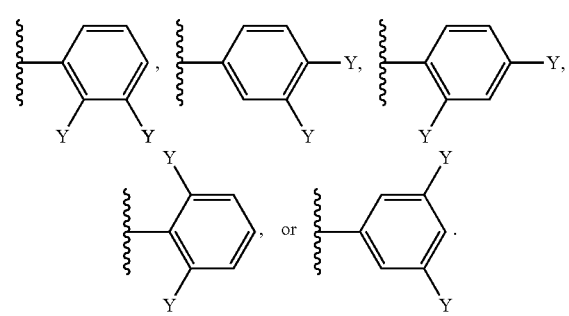

In certain embodiments, Y is halo, i.e. selected from fluoro, iodo, bromo, or chloro. In certain embodiments Y is chloro. In certain embodiments Y is fluoro.

In certain embodiments, Y is optionally substituted $C_{1-10}$alkyl or $C_{1-10}$perhaloalkyl.

In certain embodiments, Y is optionally substituted $C_{1-10}$alkyl. In certain embodiments, Y is optionally substituted $C_{1-6}$alkyl. In certain embodiments, Y is optionally substituted $C_{1-4}$alkyl. In certain embodiments, Y is optionally substituted $C_{1-3}$alkyl. In certain embodiments, Y is optionally substituted $C_{1-2}$alkyl. In certain embodiments, Y is —$CH_3$, —$CH_2F$, or —$CHF_2$.

In certain embodiments, Y is $C_{1-10}$perhaloalkyl. In certain embodiments, Y is $C_{1-6}$perhaloalkyl. In certain embodiments, Y is $C_{1-4}$perhaloalkyl. In certain embodiments, Y is $C_{1-3}$perhaloalkyl. In certain embodiments, Y is $C_{1-2}$perhaloalkyl. In certain embodiments, Y is —$CF_3$, —$CF_2Cl$, or —$CFCl_2$.

As generally defined above, Z is =O, =S, or =$NR_Z$, wherein $R_Z$ is selected from hydrogen, an amino protecting group, —OH, substituted hydroxyl, optionally substituted $C_{1-10}$ alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl, or Z represents two hydrogen atoms.

In certain embodiments, Z is =O.
In certain embodiments, Z is =S.
In certain embodiments, Z is =$NR_Z$, wherein $R_Z$ is selected from hydrogen, an amino protecting group, —OH, substituted hydroxyl, optionally substituted $C_{1-10}$alkyl, optionally substituted $C_{2-10}$alkenyl, optionally substituted $C_{2-10}$alkynyl, optionally substituted $C_{3-7}$carbocyclyl, optionally substituted 3-8-membered-heterocyclyl, optionally substituted $C_{6-10}$aryl, or optionally substituted 5-14-membered-heteroaryl. In certain embodiments, Z is =$NR_Z$ and $R_Z$ is hydrogen.

In certain embodiments, Z represents two hydrogen atoms.

As generally defined above, X is —$OR_4$, —$SR_4$, or —$N(R_4)_2$, wherein each instance of $R_4$ is independently hydrogen, optionally substituted $C_{1-30}$alkyl, optionally substituted $C_{2-30}$alkenyl, optionally substituted $C_{2-30}$alkynyl, —C(=O)$R_5$, or —C(=O)$OR_5$, wherein $R_5$ is optionally substituted $C_{1-30}$alkyl, optionally substituted $C_{2-30}$alkenyl, or optionally substituted $C_{2-30}$alkynyl, or two $R_4$ groups are joined to form an optionally substituted 3-8-membered-heterocyclyl or optionally substituted 5-14-membered-heteroaryl ring.

In certain embodiments, X is —$OR_4$. In certain embodiments, X is —$OR_4$, and $R_4$ is hydrogen. In certain embodiments, X is —$OR_4$, and $R_4$ is optionally substituted $C_{1-20}$alkyl, optionally substituted $C_{2-20}$alkenyl, or optionally substituted $C_{2-20}$alkynyl. In certain embodiments, $R_4$ is optionally substituted $C_{1-10}$ alkyl, optionally substituted $C_{2-10}$alkenyl, or optionally substituted $C_{2-10}$alkynyl. In certain embodiments, $R_4$ is optionally substituted $C_{1-6}$alkyl, e.g., $C_{1-3}$alkyl, $C_{3-4}$alkyl, or $C_{4-6}$alkyl. In certain embodiments, $R_4$ is optionally substituted $C_{2-6}$alkenyl, e.g., $C_{2-3}$alkenyl, $C_{3-4}$alkenyl, or $C_{4-6}$alkenyl. In certain embodiments, $R_4$ is optionally substituted $C_{2-6}$alkynyl, e.g., $C_{2-3}$alkynyl, $C_{3-4}$alkynyl, or $C_{4-6}$alkynyl.

In certain embodiments, X is —$OR_4$, wherein $R_4$ is —C(=O)$R_5$, or —C(=O)$OR_5$.

In certain embodiments, X is —$OR_4$, and $R_4$ is —C(=O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$OR_4$, and $R_4$ is —C(=O)$OR_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$. In certain embodiments, X is —$SR_4$, and $R_4$ is hydrogen. In certain embodiments, X is —$SR_4$, and $R_4$ is optionally substituted $C_{1-20}$alkyl, optionally substituted $C_{2-20}$alkenyl, or optionally substituted $C_{2-20}$alkynyl. In certain embodiments, $R_4$ is optionally substituted $C_{1-10}$ alkyl, optionally substituted $C_{2-10}$alkenyl, or optionally substituted $C_{2-10}$alkynyl. In certain embodiments, $R_4$ is optionally substituted $C_{1-6}$alkyl, e.g., $C_{1-3}$alkyl, $C_{3-4}$alkyl, or $C_{4-6}$alkyl. In certain embodiments, $R_4$ is optionally substituted $C_{2-6}$alkenyl, e.g., $C_{2-3}$alkenyl, $C_{3-4}$alkenyl, or $C_{4-6}$alkenyl. In certain embodiments, $R_4$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$, wherein $R_4$ is —C(=O)$R_5$, or —C(=O)$OR_5$.

In certain embodiments, X is —$SR_4$, and $R_4$ is —C(=O)$R_5$, and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$ alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$SR_4$, and $R_4$ is —C(=O)$OR_5$ and $R_5$ is optionally substituted $C_{1-20}$alkyl, optionally substituted $C_{2-20}$alkenyl, or optionally substituted $C_{2-20}$alkynyl. In certain embodiments, $R_5$ is optionally substituted $C_{1-10}$alkyl, optionally substituted $C_{2-10}$alkenyl, or optionally substituted $C_{2-10}$alkynyl. In certain embodiments, $R_5$ is optionally substituted $C_{1-6}$ alkyl, e.g., $C_{1-3}$alkyl, $C_{3-4}$alkyl, or $C_{4-6}$alkyl. In certain embodiments, $R_5$ is optionally substituted $C_{2-6}$alkenyl, e.g., $C_{2-3}$alkenyl, $C_{3-4}$alkenyl, or $C_{4-6}$alkenyl. In certain embodiments, $R_5$ is optionally substituted $C_{2-6}$alkynyl, e.g., $C_{2-3}$alkynyl, $C_{3-4}$alkynyl, or $C_{4-6}$alkynyl.

In certain embodiments, X is —$N(R_4)_2$. In certain embodiments, X is —$N(R_4)_2$ and at least one $R_4$ group is hydrogen. In certain embodiments, X is —$N(R_4)_2$ and neither of the two $R_4$ groups are hydrogen. In certain embodiments, X is —$N(R_4)_2$ and at least one $R_4$ is optionally substituted $C_{1-20}$alkyl, optionally substituted $C_{2-20}$alkenyl, or optionally substituted $C_{2-20}$alkynyl. In certain embodiments, X is —$N(R_4)_2$ and at least one $R_4$ is optionally substituted $C_{1-10}$alkyl, optionally substituted $C_{2-10}$alkenyl, or optionally substituted $C_{2-10}$alkynyl. In certain embodiments, X is —$N(R_4)_2$ and at least one $R_4$ is optionally substituted $C_{1-6}$alkyl, e.g., $C_{1-3}$alkyl, $C_{3-4}$alkyl, or $C_{4-6}$alkyl In certain embodiments, X is —$N(R_4)_2$ and at least one $R_4$ is optionally substituted $C_{2-6}$alkenyl, e.g., $C_{2-3}$alkenyl, $C_{3-4}$alkenyl, or $C_{4-6}$alkenyl. In certain embodiments, X is —$N(R_4)_2$ and at least one $R_4$ is optionally substituted $C_{2-6}$alkynyl, e.g., $C_{2-3}$alkynyl, $C_{3-4}$alkynyl, or $C_{4-6}$alkynyl. However, in certain embodiments, X is not —NH(iPr).

In certain embodiments, X is —$N(R_4)_2$ and at least one $R_4$ is —C(=O)$R_5$, or —C(=O)$OR_5$.

In certain embodiments, X is —N(R$_4$)$_2$ and at least one R$_4$ is —C(=O)R$_5$, and R$_5$ is optionally substituted C$_{1-20}$alkyl, optionally substituted C$_{2-20}$alkenyl, or optionally substituted C$_{2-20}$alkynyl. In certain embodiments, R$_5$ is optionally substituted C$_{1-10}$alkyl, optionally substituted C$_{2-10}$alkenyl, or optionally substituted C$_{2-10}$alkynyl. In certain embodiments, R$_5$ is optionally substituted C$_{1-6}$alkyl, e.g., C$_{1-3}$alkyl, C$_{3-4}$alkyl, or C$_{4-6}$alkyl. In certain embodiments, R$_5$ is optionally substituted C$_{2-6}$alkenyl, e.g., C$_{2-3}$alkenyl, C$_{3-4}$alkenyl, or C$_{4-6}$alkenyl. In certain embodiments, R$_5$ is optionally substituted C$_{2-6}$alkynyl, e.g., C$_{2-3}$alkynyl, C$_{3-4}$alkynyl, or C$_{4-6}$alkynyl.

In certain embodiments, X is —N(R$_4$)$_2$ and at least one R$_4$ is —C(=O)OR$_5$ and R$_5$ is optionally substituted C$_{1-20}$alkyl, optionally substituted C$_{2-20}$alkenyl, or optionally substituted C$_{2-20}$alkynyl. In certain embodiments, R$_5$ is optionally substituted C$_{1-10}$alkyl, optionally substituted C$_{2-10}$alkenyl, or optionally substituted C$_{2-10}$alkynyl. In certain embodiments, R$_5$ is optionally substituted C$_{1-6}$ alkyl, e.g., C$_{1-3}$alkyl, C$_{3-4}$alkyl, or C$_{4-6}$alkyl. In certain embodiments, R$_5$ is optionally substituted C$_{2-6}$alkenyl, e.g., C$_{2-3}$alkenyl, C$_{3-4}$alkenyl, or C$_{4-6}$alkenyl. In certain embodiments, R$_5$ is optionally substituted C$_{2-6}$alkynyl, e.g., C$_{2-3}$alkynyl, C$_{3-4}$alkynyl, or C$_{4-6}$alkynyl.

In other embodiments, X is —N(R$_4$)$_2$ and the two R$_4$ groups are joined to form an optionally substituted 3-8-membered-heterocyclyl or optionally substituted 5-14-membered-heteroaryl ring.

In certain embodiments, wherein X is —OR$_4$, —SR$_4$, or —N(R$_4$)$_2$, any one of R$_4$ or R$_5$ is optionally substituted C$_{1-30}$alkyl (e.g., C$_{1-10}$alkyl, C$_{1-6}$ alkyl, C$_{1-3}$alkyl, C$_{7-30}$alkyl, C$_{10-30}$alkyl, C$_{7-25}$alkyl, C$_{10-25}$alkyl, C$_{15-25}$alkyl). In certain embodiments, any one of R$_4$ or R$_5$ is optionally substituted C$_{2-30}$alkenyl (e.g., C$_{2-10}$alkenyl, C$_{2-6}$alkenyl, C$_{1-3}$alkenyl, C$_{7-30}$alkenyl, C$_{1-30}$alkenyl, C$_{7-25}$alkenyl, C$_{10-25}$alkenyl, C$_{15-25}$alkenyl). In certain embodiments, any one of R$_4$ or R$_5$ is optionally substituted C$_{2-30}$alkynyl (e.g., C$_{2-10}$alkynyl, C$_{2-6}$alkynyl, C$_{1-3}$alkynyl, C$_{7-30}$alkynyl, C$_{10-30}$alkynyl, C$_{7-25}$alkynyl, C$_{10-25}$alkynyl, C$_{15-25}$alkynyl).

In any of the above embodiments, when R$_4$ or R$_5$ are defined as a C$_{7-30}$alkyl or C$_{7-30}$alkenyl groups, such groups may also be referred to as "lipid tails." Lipid tails present in these lipid groups can be saturated and unsaturated, depending on whether or not the lipid tail comprises double bonds. The lipid tail can also comprise different lengths, often categorized as medium (i.e., with tails between 7-12 carbons, e.g., C$_{7-12}$ alkyl or C$_{7-12}$ alkenyl), long (i.e., with tails greater than 12 carbons and up to 22 carbons, e.g., C$_{13-22}$ alkyl or C$_{13-22}$ alkenyl), or very long (i.e., with tails greater than 22 carbons, e.g., C$_{23-30}$ alkyl or C$_{23-30}$ alkenyl).

Exemplary unsaturated lipid tails include, but are not limited to:

| | |
|---|---|
| Myristoleic | —(CH$_2$)$_7$CH=CH(CH$_2$)$_3$CH$_3$, |
| Palmitoliec | —(CH$_2$)$_7$CH=CH(CH$_2$)$_5$CH$_3$, |
| Sapienic | —(CH$_2$)$_4$CH=CH(CH$_2$)$_8$CH$_3$, |
| Oleic | —(CH$_2$)$_7$CH=CH(CH$_2$)$_7$CH$_3$, |
| Linoleic | —(CH$_2$)$_7$CH=CHCH$_2$CH=CH(CH$_2$)$_4$CH$_3$, |
| α-Linolenic | —(CH$_2$)$_7$CH=CHCH$_2$CH=CHCH$_2$CH=CHCH$_2$CH$_3$, |
| Arachinodonic | —(CH$_2$)$_3$CH=CHCH$_2$CH=CHCH$_2$CH=CHCH$_2$CH=CH(CH$_2$)$_4$CH$_3$, |
| Eicosapentaenoic | —(CH$_2$)$_3$CH=CHCH$_2$CH=CHCH$_2$CH=CHCH$_2$CH=CHCH$_2$CH=CHCH$_2$CH$_3$, |
| Erucic | —(CH$_2$)$_{11}$CH=CH(CH$_2$)$_7$CH$_3$, and |
| Docosahexaenoic | —(CH$_2$)$_2$CH=CHCH$_2$CH=CHCH$_2$CH=CHCH$_2$CH=CHCH$_2$CH=CHCH$_2$CH=CH—CH$_2$CH$_3$. |

Exemplary saturated lipid tails include, but are not limited to:

| | |
|---|---|
| Lauric | —(CH$_2$)$_{10}$CH$_3$, |
| Myristic | —(CH$_2$)$_{12}$CH$_3$, |
| Palmitic | —(CH$_2$)$_{14}$CH$_3$, |
| Stearic | —(CH$_2$)$_{16}$CH$_3$, |
| Arachidic | —(CH$_2$)$_{18}$CH$_3$, |
| Behenic | —(CH$_2$)$_{20}$CH$_3$, |
| Lignoceric | —(CH$_2$)$_{22}$CH$_3$, and |
| Cerotic | —(CH$_2$)$_{24}$CH$_3$. |

In certain embodiments of Formula (I), the compound is of Formula (I-a):

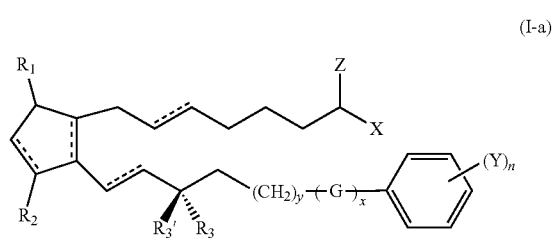

(I-a)

or a pharmaceutically acceptable salt, hydrate, solvate, stereoisomer, polymorph, tautomer, isotopically enriched derivative, or prodrug thereof; wherein R$_1$, R$_2$, Z, and X are as defined herein;

each instance of ===== independently represents a single bond or a double bond which can be in the cis or trans configuration;

each instance of R$_3$ and R$_3$' is independently hydrogen, halogen, —OH, substituted hydroxyl, or —O(CO)R$_8$, wherein R$_8$ is optionally substituted C$_{1-20}$alkyl, optionally substituted C$_{2-20}$alkenyl, optionally substituted C$_{2-20}$alkynyl, or —(CH$_2$)$_m$R$_9$ wherein m is 0 or an integer between 1-10, inclusive, and R$_9$ is optionally substituted C$_{3-7}$carbocyclyl, optionally substituted C$_{6-10}$aryl, or optionally substituted 5-14-membered-heteroaryl, or R$_3$ and R$_3$' are joined to form =O;

Y is selected from the group consisting of optionally substituted C$_{1-10}$alkyl, C$_{1-10}$perhaloalkyl, optionally substituted C$_{2-10}$alkenyl, optionally substituted C$_{2-10}$alkynyl, halo, nitro, cyano, thiol, substituted thiol, hydroxyl, substituted hydroxyl, amino, monosubstituted amino, and disubstituted amino;

G is —O— or —S—;

y is 0, 1, or 2;

x is 0 or 1; and n is 0 or an integer of from 1 to 5, inclusive.

In certain embodiments of Formula (I-a), wherein $R_3'$ is hydrogen, the compound is of Formula (I-b):

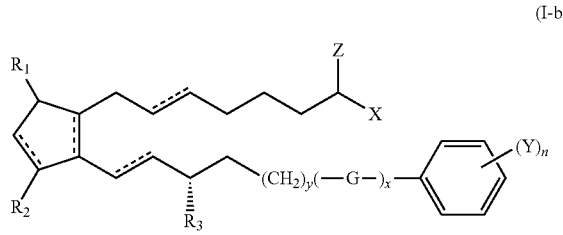
(I-b)

or a pharmaceutically acceptable salt, hydrate, solvate, stereoisomer, polymorph, tautomer, isotopically enriched derivative, or prodrug thereof; wherein ═══, $R_1$, $R_2$, $R_3$, Z, X, Y, G, y, x, and n are as defined herein.

In certain embodiments of Formula (I-a), wherein $R_3$ is hydrogen, the compound is of Formula (I-c):

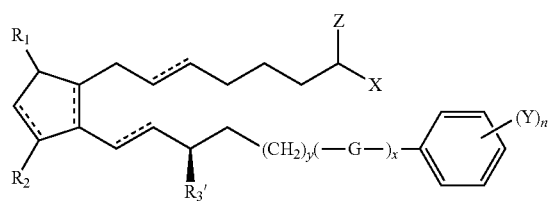
(I-c)

or a pharmaceutically acceptable salt, hydrate, solvate, stereoisomer, polymorph, tautomer, isotopically enriched derivative, or prodrug thereof; wherein ═══, $R_1$, $R_2$, $R_3'$, Z, X, Y, G, y, x, and n are as defined herein.

In certain embodiments, G is —O—. In certain embodiments, G is —S—.

In certain embodiments of Formula (I-a), wherein G is —O—, provided is a compound of Formula (I-a1):

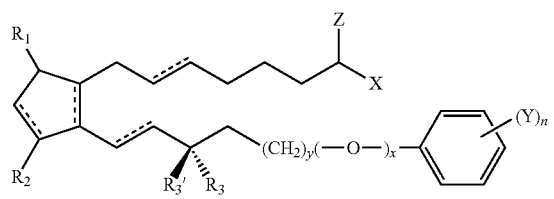
(I-a1)

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein ═══, $R_1$, $R_2$, $R_3$, $R_3'$, Z, X, Y, y, x, and n are as defined herein.

In certain embodiments of Formula (I-b), wherein G is —O—, the compound is of Formula (I-b1):

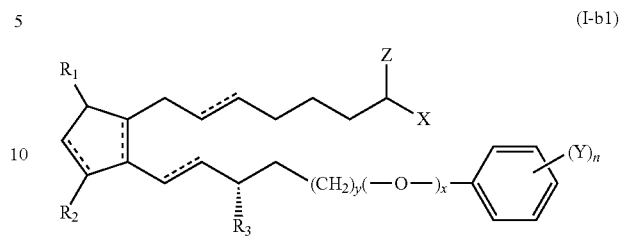
(I-b1)

or a pharmaceutically acceptable salt, hydrate, solvate, stereoisomer, polymorph, tautomer, isotopically enriched derivative, or prodrug thereof; wherein ═══, $R_1$, $R_2$, $R_3$, Z, X, Y, y, x, and n are as defined herein.

In certain embodiments of Formula (I-c), wherein G is —O—, the compound is of Formula (I-c1):

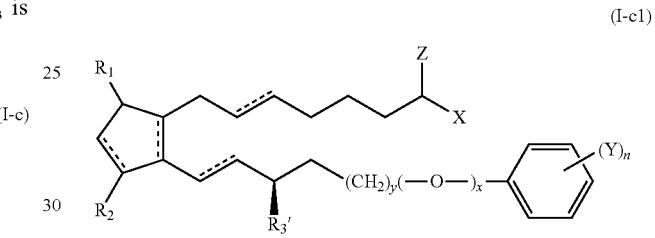
(I-c1)

or a pharmaceutically acceptable salt, hydrate, solvate, stereoisomer, polymorph, tautomer, isotopically enriched derivative, or prodrug thereof; wherein ═══, $R_1$, $R_2$, $R_3'$, Z, X, Y, y, x, and n are as defined herein.

In certain embodiments of Formula (I-a), wherein G is —S—, provided is a compound of Formula (I-a2):

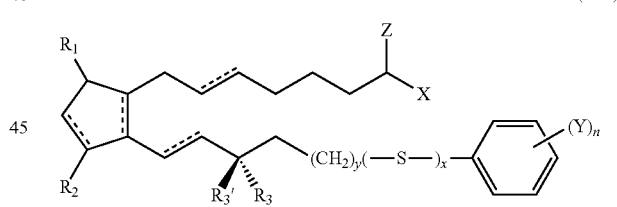
(I-a2)

or a pharmaceutically acceptable salt, hydrate, solvate, stereoisomer, polymorph, tautomer, isotopically enriched derivative, or prodrug thereof; wherein ═══, $R_1$, $R_2$, $R_3$, $R_3'$, Z, X, Y, y, x, and n are as defined herein.

In certain embodiments of Formula (I-b), wherein G is —S—, the compound is of Formula (I-b2):

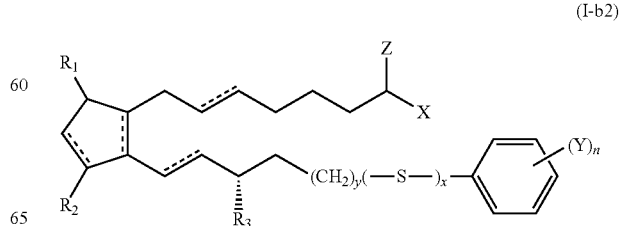
(I-b2)

or a pharmaceutically acceptable salt, hydrate, solvate, stereoisomer, polymorph, tautomer, isotopically enriched derivative, or prodrug thereof; wherein ≈≈≈, $R_1$, $R_2$, $R_3$, Z, X, Y, y, x, and n are as defined herein.

In certain embodiments of Formula (I-c), wherein G is —S—, the compound is of Formula (I-c2):

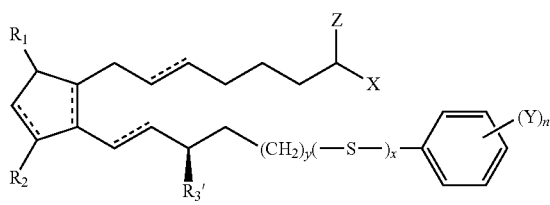

(I-c2)

or a pharmaceutically acceptable salt, hydrate, solvate, stereoisomer, polymorph, tautomer, isotopically enriched derivative, or prodrug thereof; wherein ≈≈≈, $R_1$, $R_2$, $R_3'$, Z, X, Y, y, x, and n are as defined herein.

In certain embodiments, the compound of Formula (I-a) has the following stereochemistry, also referred to herein as a compound of Formula (I-d):

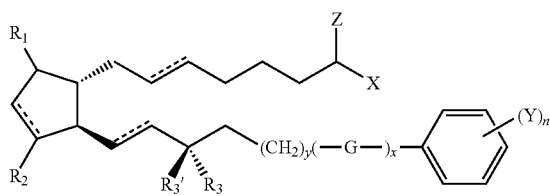

(I-d)

or a pharmaceutically acceptable salt, hydrate, solvate, stereoisomer, polymorph, tautomer, isotopically enriched derivative, or prodrug thereof; wherein ≈≈≈, $R_1$, $R_2$, $R_3$, $R_3'$, Z, Y, G, X, y, x, and n are as defined herein.

In certain embodiments of Formula (I-d), wherein $R_3'$ is hydrogen, the compound is of Formula (I-e):

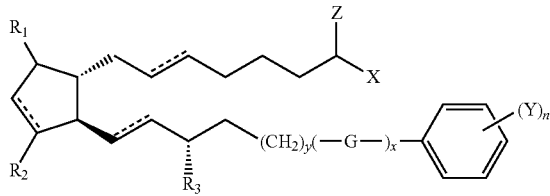

(I-e)

or a pharmaceutically acceptable salt, hydrate, solvate, stereoisomer, polymorph, tautomer, isotopically enriched derivative, or prodrug thereof; wherein ≈≈≈, $R_1$, $R_2$, $R_3$, Z, X, Y, G, y, x, and n are as defined herein.

In certain embodiments of Formula (I-d), wherein $R_3$ is hydrogen, the compound is of Formula (I-f):

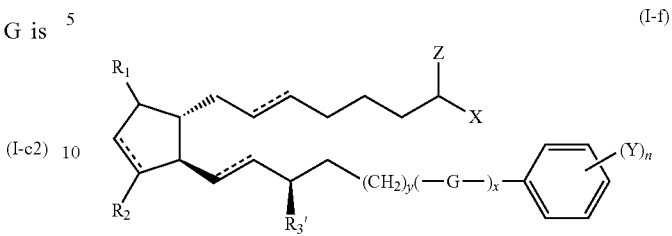

(I-f)

or a pharmaceutically acceptable salt, hydrate, solvate, stereoisomer, polymorph, tautomer, isotopically enriched derivative, or prodrug thereof; wherein ≈≈≈, $R_1$, $R_2$, $R_3'$ Z, X, Y, G, y, x, and n are as defined herein.

In certain embodiments, G is —O—. In certain embodiments, G is —S—.

In certain embodiments of Formula (I-d), wherein G is —O—, the compound is of Formula (I-d1):

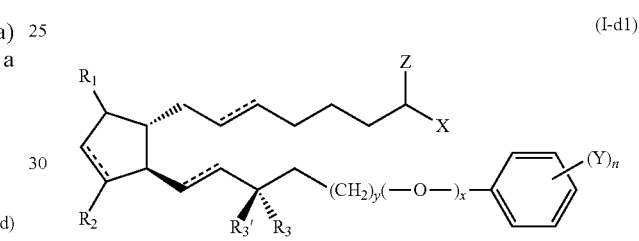

(I-d1)

or a pharmaceutically acceptable salt, hydrate, solvate, stereoisomer, polymorph, tautomer, isotopically enriched derivative, or prodrug thereof; wherein ≈≈≈, $R_1$, $R_2$, $R_3$, $R_3'$, Z, Y, X, y, x, and n are as defined herein.

In certain embodiments of Formula (I-e), wherein G is —O—, the compound is of Formula (I-e1):

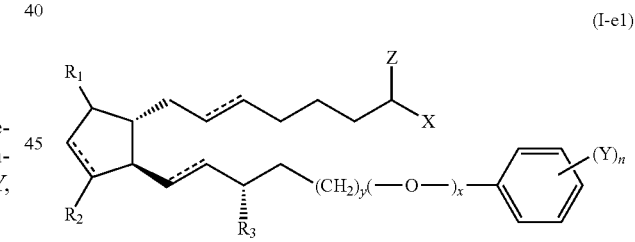

(I-e1)

or a pharmaceutically acceptable salt, hydrate, solvate, stereoisomer, polymorph, tautomer, isotopically enriched derivative, or prodrug thereof; wherein ≈≈≈, $R_1$, $R_2$, $R_3$, Z, X, Y, y, x, and n are as defined herein.

In certain embodiments of Formula (I-f), wherein G is —O—, the compound is of Formula (I-f1):

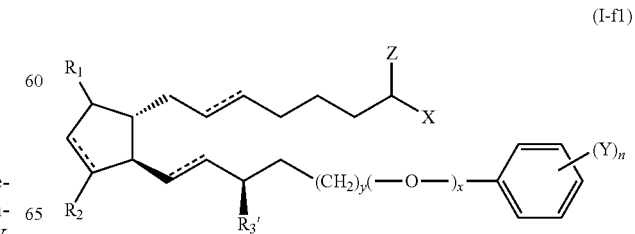

(I-f1)

or a pharmaceutically acceptable salt, hydrate, solvate, stereoisomer, polymorph, tautomer, isotopically enriched derivative, or prodrug thereof; wherein ═════, R₁, R₂, R₃', Z, X, Y, y, x, and n are as defined herein.

In certain embodiments of Formula (I-d), wherein G is —S—, the compound is of Formula (I-d2):

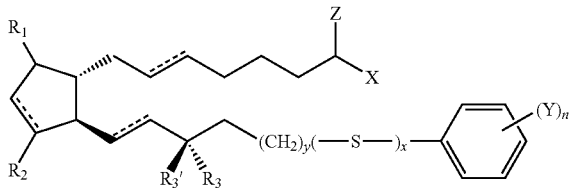

(I-d2)

or a pharmaceutically acceptable salt, hydrate, solvate, stereoisomer, polymorph, tautomer, isotopically enriched derivative, or prodrug thereof; wherein ═════, R₁, R₂, R₃, R₃', Z, Y, X, y, x, and n are as defined herein.

In certain embodiments of Formula (I-e), wherein G is —S—, the compound is of Formula (I-e2):

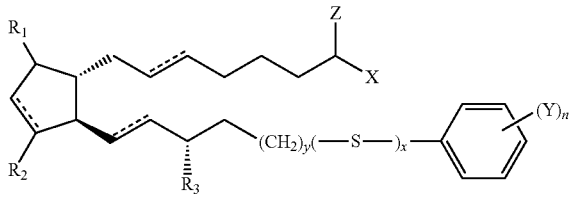

(I-e2)

or a pharmaceutically acceptable salt, hydrate, solvate, stereoisomer, polymorph, tautomer, isotopically enriched derivative, or prodrug thereof; wherein ═════, R₁, R₂, R₃, Z, X, Y, y, x, and n are as defined herein.

In certain embodiments of Formula (I-f), wherein G is —S—, the compound is of Formula (I-f2):

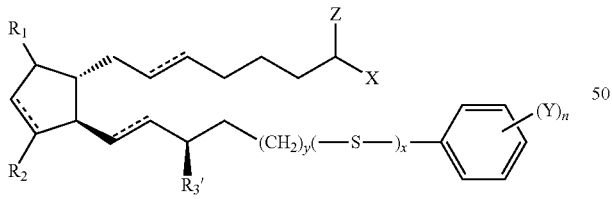

(I-f2)

or a pharmaceutically acceptable salt, hydrate, solvate, stereoisomer, polymorph, tautomer, isotopically enriched derivative, or prodrug thereof; wherein ═════, R₁, R₂, R₃', Z, X, Y, y, x, and n are as defined herein.

In certain embodiments, Z is ═O.

In certain embodiments, each ═════ represents a single bond.

In certain embodiments, each instance of R₁ and R₂ is —OH.

In certain embodiments of Formula (I-d2), wherein Z is ═O and each ═════ represents a single bond, provided is a compound of Formula (I-g):

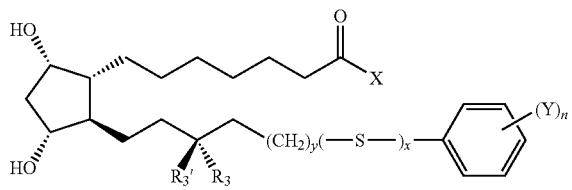

(I-g)

or a pharmaceutically acceptable salt, hydrate, solvate, stereoisomer, polymorph, tautomer, isotopically enriched derivative, or prodrug thereof; wherein X, Y, y, x, and n are as defined herein.

In certain embodiments, the compound for use in the present invention is

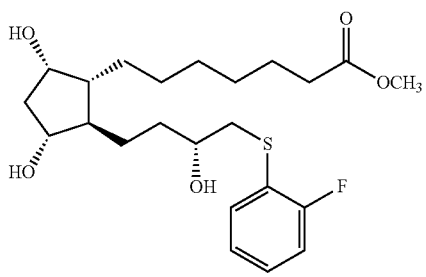 [SMILES: COC(=O)CCCCCC[C@@H]1[C@@H](CC[C@@H](O)CSc2ccccc2F)[C@H](O)C[C@@H]1O]

also referred to herein as CAY10509, or a pharmaceutically acceptable salt, hydrate, solvate, stereoisomer, polymorph, tautomer, isotopically enriched derivative, or prodrug thereof.

In certain embodiments, the compound for use in the present invention is

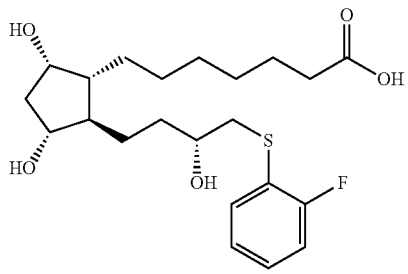 [SMILES: O=C(O)CCCCCC[C@@H]1[C@@H](CC[C@@H](O)CSc2ccccc2F)[C@H](O)C[C@@H]1O]

also referred to herein as CAY10509 free acid, or a pharmaceutically acceptable salt, hydrate, solvate, stereoisomer, polymorph, tautomer, isotopically enriched derivative, or prodrug thereof.

In certain embodiments at least one exocyclic ═════ represents a cis-double bond.

For example, in certain embodiments of Formula (I-d1), wherein each instance of R₁ and R₂ is —OH, and Z is ═O, provided is a compound of Formula (I-e):

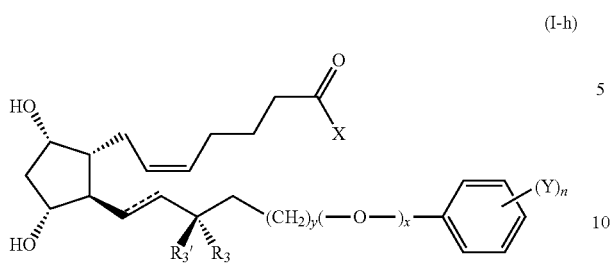

(I-h)

or a pharmaceutically acceptable salt, hydrate, solvate, stereoisomer, polymorph, tautomer, isotopically enriched derivative, or prodrug thereof; wherein ━━━, $R_3$, $R_3'$, Y, X, y, x, and n are as defined herein.

In certain embodiments of Formula (I-h), wherein $R_3'$ is hydrogen, provided is a compound of Formula (I-i):

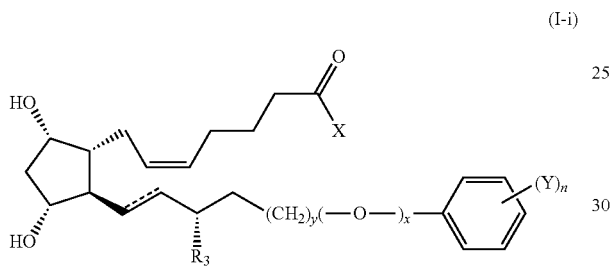

(I-i)

or a pharmaceutically acceptable salt, hydrate, solvate, stereoisomer, polymorph, tautomer, isotopically enriched derivative, or prodrug thereof; wherein ━━━, $R_3$, Y, X, y, x, and n are as defined herein.

In certain embodiments of Formula (I-i), wherein $R_3$ is —OH, the compound for use in the present invention is of Formula (I-j):

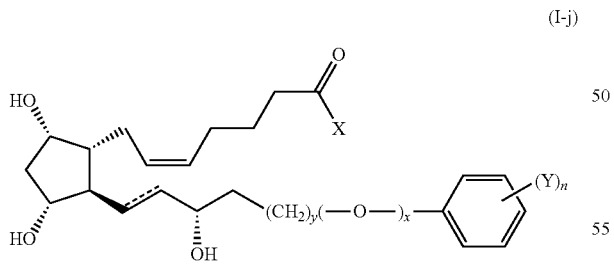

(I-j)

or a pharmaceutically acceptable salt, hydrate, solvate, stereoisomer, polymorph, tautomer, isotopically enriched derivative, or prodrug thereof; wherein Y, X, y, x, and n are as defined herein.

In certain embodiments, the compound of Formula (I-j), wherein ━━━ is a trans double bond, X is —NHCH$_2$CH$_3$, y is 1, x is 0, and n is 0, is the compound:

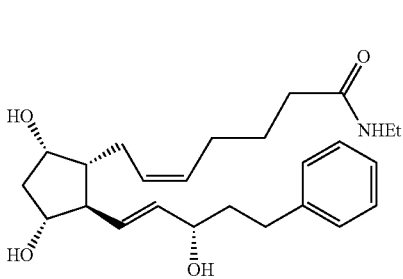

also referred to herein as 17-phenyl trinor prostaglandin F2α ethyl amide, or bimatoprost; or a pharmaceutically acceptable salt, hydrate, solvate, stereoisomer, polymorph, tautomer, isotopically enriched derivative, or prodrug thereof.

In certain embodiments, the compound of Formula (I-j), wherein ━━━ is a trans double bond, X is —OCH(CH$_3$)$_2$, y is 1, x is 0, and n is 0, is the compound:

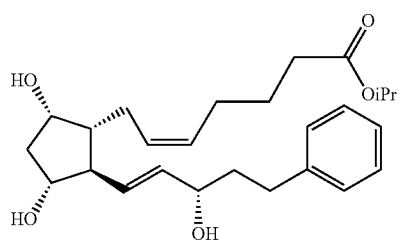 [SMILES: CC(C)OC(=O)CCC/C=C\C[C@@H]1[C@@H](/C=C/[C@@H](O)CCc2ccccc2)[C@H](O)C[C@@H]1O]

also referred to herein as 17-phenyl trinor prostaglandin F2α isopropyl ester, or bimatoprost isopropyl ester; or a pharmaceutically acceptable salt, hydrate, solvate, stereoisomer, polymorph, tautomer, isotopically enriched derivative, or prodrug thereof.

In certain embodiments, the compound of Formula (I-j), wherein ━━━ is a trans double bond, X is —OH, y is 1, x is 0, and n is 0, is the compound:

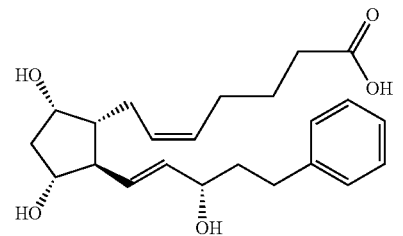 [SMILES: O=C(O)CCC/C=C\C[C@@H]1[C@@H](/C=C/[C@@H](O)CCc2ccccc2)[C@H](O)C[C@@H]1O]

also referred to herein as 17-phenyl trinor prostaglandin F2α, or bimatoprost free acid; or a pharmaceutically acceptable salt, hydrate, solvate, stereoisomer, polymorph, tautomer, isotopically enriched derivative, or prodrug thereof.

In certain embodiments, the compound of Formula (I-j), wherein ━━━ is a trans double bond, X is —OCH(CH$_3$)$_2$, y is 0, x is 1, and n is 1, is the compound:

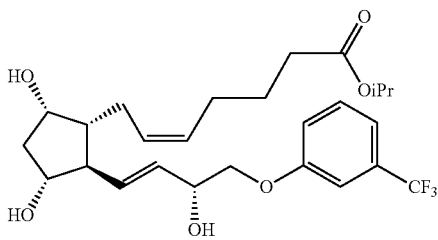 [SMILES: CC(C)OC(=O)CCC/C=C\C[C@@H]1[C@@H](/C=C/[C@@H](O)COc2cccc(C(F)(F)F)c2)[C@H](O)C[C@@H]1O]

also referred to herein as fluprostenol isopropyl ester, or travoprost; or a pharmaceutically acceptable salt, hydrate, solvate, stereoisomer, polymorph, tautomer, isotopically enriched derivative, or prodrug thereof.

In certain embodiments, the compound of Formula (I-j), wherein ===== is a trans double bond, X is —OH, y is 0, x is 1, and n is 1, is the compound:

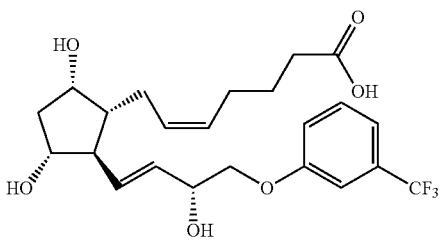 [SMILES: O=C(O)CCC/C=C\C[C@@H]1[C@@H](/C=C/[C@@H](O)COc2cccc(C(F)(F)F)c2)[C@H](O)C[C@@H]1O]

also referred to herein as travoprost free acid; or a pharmaceutically acceptable salt, hydrate, solvate, stereoisomer, polymorph, tautomer, isotopically enriched derivative, or prodrug thereof.

In certain embodiments, the compound of Formula (I-j), wherein ===== is a single bond, X is —OCH(CH$_3$)$_2$, y is 1, x is 0, and n is 0, is the compound:

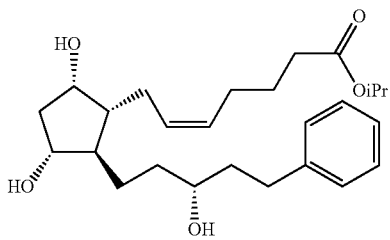 [SMILES: CC(C)OC(=O)CCC/C=C\C[C@@H]1[C@@H](CC[C@@H](O)CCc2ccccc2)[C@H](O)C[C@@H]1O]

also referred to herein as 17-phenyl-13,14-dihydro trinor prostaglandin F2α isopropyl ester, or latanoprost; or a pharmaceutically acceptable salt, hydrate, solvate, stereoisomer, polymorph, tautomer, isotopically enriched derivative, or prodrug thereof.

In certain embodiments, the compound of Formula (I-j), wherein ===== is a single bond, X is —OH, y is 1, x is 0, and n is 0, is the compound:

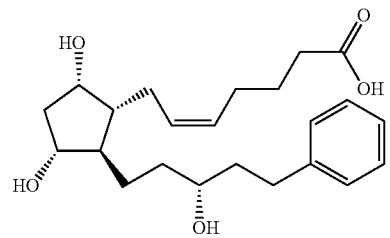 [SMILES: O=C(O)CCC/C=C\C[C@@H]1[C@@H](CC[C@@H](O)CCc2ccccc2)[C@H](O)C[C@@H]1O]

also referred to herein as latanoprost free acid; or a pharmaceutically acceptable salt, hydrate, solvate, stereoisomer, polymorph, tautomer, isotopically enriched derivative, or prodrug thereof.

In certain embodiments of Formula (I-h), wherein R$_3$ is F and R$_3$' is F, the compound for use in the present invention is of Formula (I-k):

(I-k)

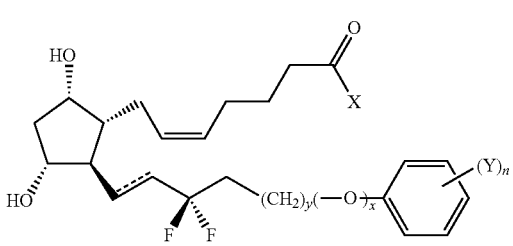

or a pharmaceutically acceptable salt, hydrate, solvate, stereoisomer, polymorph, tautomer, isotopically enriched derivative, or prodrug thereof; wherein =====, Y, X, y, x, and n are as defined herein.

In certain embodiments, the compound of Formula (I-k), wherein ===== is a trans double bond, X is —OCH(CH$_3$)$_2$, y is 1, x is 1, and n is 0, is the compound:

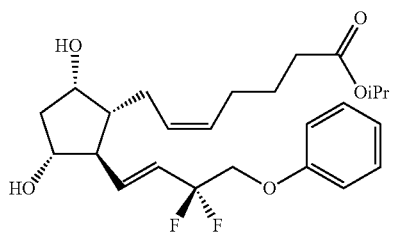

also referred to herein as tafluprost; or a pharmaceutically acceptable salt, hydrate, solvate, stereoisomer, polymorph, tautomer, isotopically enriched derivative, or prodrug thereof.

In certain embodiments, the compound of Formula (I-k), wherein ===== is a trans double bond, X is —OH, y is 1, x is 1, and n is 0, is the compound:

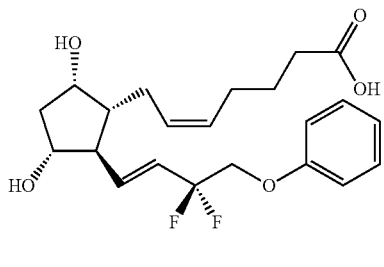

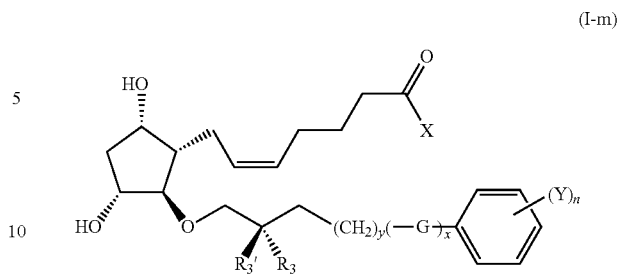

also referred to herein as tafluprost free acid; or a pharmaceutically acceptable salt, hydrate, solvate, stereoisomer, polymorph, tautomer, isotopically enriched derivative, or prodrug thereof.

In certain embodiments of Formula (I), the compound of Formula (I-l):

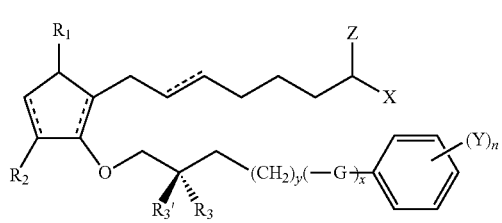

or a pharmaceutically acceptable salt, hydrate, solvate, stereoisomer, polymorph, tautomer, isotopically enriched derivative, or prodrug thereof; wherein $R_1$, $R_2$, Z, and X are as defined herein;

each instance of ═══ independently represents a single bond or a double bond which can be in the cis or trans configuration;

each instance of $R_3$ and $R_3'$ is independently hydrogen, halogen, —OH, substituted hydroxyl, or —O(CO)$R_8$, wherein $R_8$ is optionally substituted $C_{1-20}$alkyl, optionally substituted $C_{2-20}$alkenyl, optionally substituted $C_{2-20}$alkynyl, or —(CH$_2$)$_m$R$_9$ wherein m is 0 or an integer between 1-10, inclusive, and $R_9$ is optionally substituted $C_{3-7}$carbocyclyl, optionally substituted $C_{6-10}$aryl, or optionally substituted 5-14-membered-heteroaryl, or $R_3$ and $R_3'$ are joined to form ═O;

Y is selected from the group consisting of optionally substituted $C_{1-10}$alkyl, $C_{1-10}$perhaloalkyl, optionally substituted $C_{2-10}$alkenyl, optionally substituted $C_{2-10}$alkynyl, halo, nitro, cyano, thiol, substituted thiol, hydroxyl, substituted hydroxyl, amino, monosubstituted amino, and disubstituted amino;

G is —O— or —S—;

y is 0, 1, or 2;

x is 0 or 1; and n is 0 or an integer of from 1 to 5, inclusive.

In certain embodiments of Formula (I-1), wherein Z is ═O, and $R_1$ and $R_2$ are each —OH, provided is a compound of Formula (I-m):

or a pharmaceutically acceptable salt, hydrate, solvate, stereoisomer, polymorph, tautomer, isotopically enriched derivative, or prodrug thereof; wherein $R_1$, $R_2$, Z, and X are as defined herein.

In certain embodiments of Formula (I-m), wherein $R_3'$ is hydrogen, y is 2 and x is 0, provided is a compound of Formula (I-n):

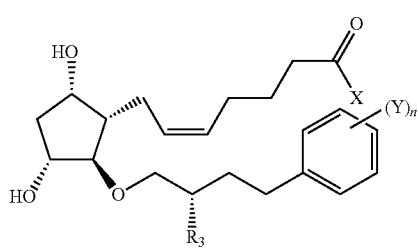

or a pharmaceutically acceptable salt, hydrate, solvate, stereoisomer, polymorph, tautomer, isotopically enriched derivative, or prodrug thereof; wherein $R_1$, $R_2$, Z, and X are as defined herein.

In certain embodiments, the compound of Formula (I-n), wherein $R_3$ is —OH, and X is —OH, is the compound:

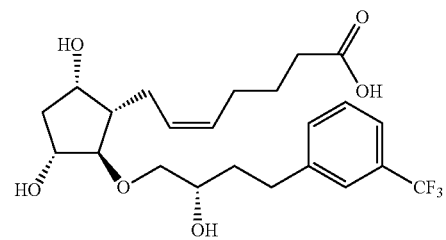 [SMILES: O=C(O)CCC/C=C\C[C@@H]1[C@@H](OC[C@@H](O)CCc2cccc(C(F)(F)F)c2)[C@H](O)C[C@@H]1O]

also referred to as AL-16082, or a pharmaceutically acceptable salt, hydrate, solvate, stereoisomer, polymorph, tautomer, isotopically enriched derivative, or prodrug thereof; wherein $R_1$, $R_2$, Z, and X are as defined herein. See, e.g., Feng et al, supra, incorporated herein by reference.

In certain embodiments, the compound useful in the present invention is of Formula (I):

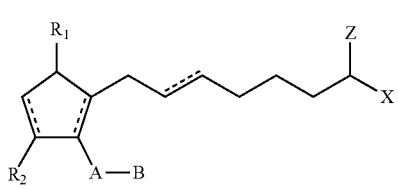

or a pharmaceutically acceptable salt, hydrate, solvate, stereoisomer, polymorph, tautomer, isotopically enriched derivative, or prodrug thereof;

wherein each instance of ===== independently represents a single bond or a double bond which can be in the cis or trans configuration;

A is alkylene or alkenylene having from two to six carbon atoms, wherein the alkylene or alkenylene group is optionally interrupted by one or more —O— groups and optionally substituted with one or more halogen, hydroxy, oxo, alkyloxy or alkylcarboxy groups, wherein each instance of alkyl alone or part of another group independently comprises from one to six carbon atoms;

B is cycloalkyl having from three to seven carbon atoms, aryl having from six to ten carbon atoms, or heteroaryl having from four to ten carbon atoms and one to four heteroatoms selected from the group consisting of nitrogen, oxygen and sulfur;

X is —OR$_4$ or —N(R$_4$)$_2$, wherein R$_4$ is selected from the group consisting of hydrogen, alkyl having from one to six carbon atoms, —C(=O)R$_5$, or —C(=O)OR$_5$, wherein R$_5$ is alkyl having from one to six carbon atoms;

Z is =O or represents two hydrogen atoms; and one of R$_1$ and R$_2$ is =O, —OH, or a —O(CO)R$_6$ group and the other one is —OH or —O(CO)R$_6$, or R$_1$ is =O and R$_2$ is H, wherein R$_6$ is a saturated or unsaturated acyclic hydrocarbon group having from 1 to about 20 carbon atoms or —(CH$_2$)$_m$R$_7$ wherein m is 0-10, and R$_7$ is cycloalkyl having from three to seven carbon atoms, aryl having from six to ten carbon atoms, or heteroaryl having from four to ten carbon atoms and one to four heteroatoms selected from the group consisting of nitrogen, oxygen and sulfur.

As generally defined above, in certain embodiments, the compound useful in the present invention is of Formula (II):

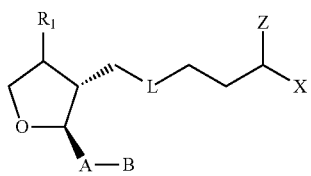

(II)

or a pharmaceutically acceptable salt, hydrate, solvate, stereoisomer, polymorph, tautomer, isotopically enriched derivative, or prodrug thereof;
wherein A, B, X, Z, L, and R$_1$ are as defined herein. are as defined herein.

In certain embodiments, L is a group of the formula

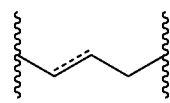

wherein ===== represents a single bond.

In certain embodiments, L is a group of the formula

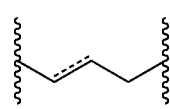

wherein ===== represents a double bond which can be in the cis or trans configuration. In certain embodiments, the double bond is in the cis configuration. In certain embodiments, the double bond is in the trans configuration In certain embodiments, L is a group of the formula

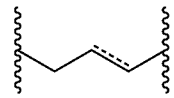

wherein ===== represents a single bond.

In certain embodiments, L is a group of the formula

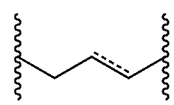

wherein ===== represents a double bond which can be in the cis or trans configuration. In certain embodiments, the double bond is in the cis configuration. In certain embodiments, the double bond is in the trans configuration In certain embodiments of Formula (II), the compound of Formula (II-a):

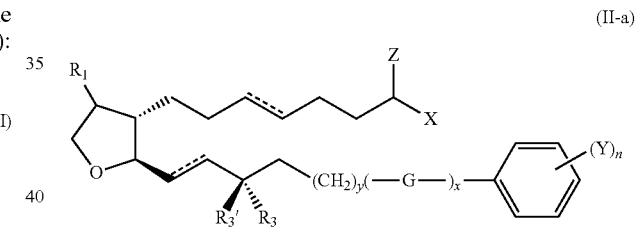

(II-a)

or a pharmaceutically acceptable salt, hydrate, solvate, stereoisomer, polymorph, tautomer, isotopically enriched derivative, or prodrug thereof; wherein R$_1$, Z, and X are as defined herein; wherein =====, R$_1$, Z, X, Y, G, R$_3$, R$_3$', y, x, and n are as defined herein.

In certain embodiments of Formula (II-a), wherein R$_3$' is hydrogen, the compound is of Formula (II-b):

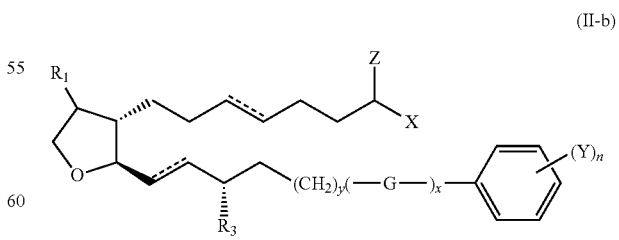

(II-b)

or a pharmaceutically acceptable salt, hydrate, solvate, stereoisomer, polymorph, tautomer, isotopically enriched derivative, or prodrug thereof; wherein =====, R$_1$, R$_3$, Z, X, Y, G, y, x, and n are as defined herein.

In certain embodiments of Formula (II-a), wherein $R_3$ is hydrogen, the compound is of Formula (II-c):

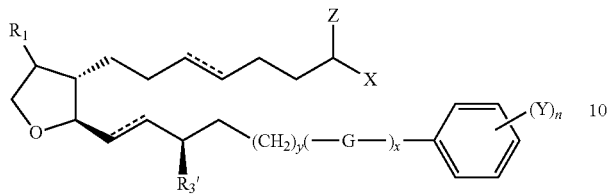
(II-c)

or a pharmaceutically acceptable salt, hydrate, solvate, stereoisomer, polymorph, tautomer, isotopically enriched derivative, or prodrug thereof; wherein =====, $R_1$, $R_2$, $R_3'$, Z, X, Y, G, y, x, and n are as defined herein.

In certain embodiments, G is —O—. In certain embodiments, G is —S—.

In certain embodiments of Formula (II-a), wherein G is —O—, provided is a compound of Formula (II-a1):

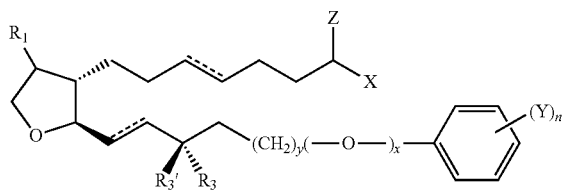
(II-a1)

or a pharmaceutically acceptable salt, hydrate, solvate, stereoisomer, polymorph, tautomer, isotopically enriched derivative, or prodrug thereof; wherein $R_1$, $R_2$, Z, and X are as defined herein; wherein =====, $R_1$, $R_2$, $R_3$, $R_3'$, Z, X, Y, y, x, and n are as defined herein.

In certain embodiments, Z is =O.

In certain embodiments at least one exocyclic ===== represents a cis-double bond.

For example, in certain embodiments of Formula (II-a1), wherein Z is =O, provided is a compound of Formula (II-d):

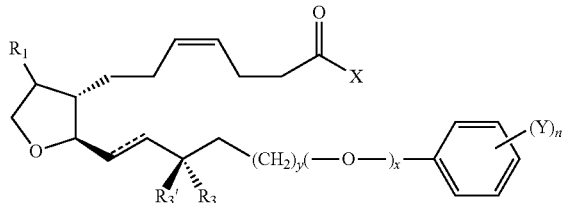
(II-d)

or a pharmaceutically acceptable salt, hydrate, solvate, stereoisomer, polymorph, tautomer, isotopically enriched derivative, or prodrug thereof; wherein =====, $R_1$, $R_3$, $R_3'$, Y, X, y, x, and n are as defined herein.

In certain embodiments of Formula (II-d), wherein $R_1$ is OH, $R_3'$ is hydrogen, $R_3$ is —OH, y is 0, and x is 1, provided is a compound of Formula (II-e):

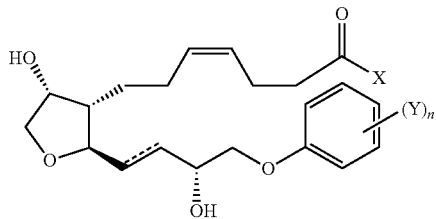
(II-e)

or a pharmaceutically acceptable salt, hydrate, solvate, stereoisomer, polymorph, tautomer, isotopically enriched derivative, or prodrug thereof; wherein =====, Y, X, and n are as defined herein.

In certain embodiments of Formula (II-e), wherein X is —OCH(CH$_3$)$_2$, the compound is:

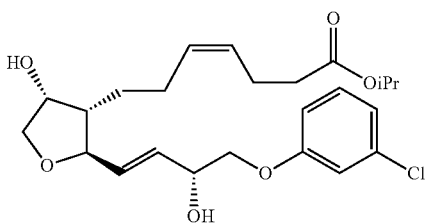 [SMILES: CC(C)OC(=O)CC/C=C\CC[C@H]1[C@@H](O)CO[C@@H]1/C=C/[C@@H](O)COc1cccc(Cl)c1]

also referred to as AL-12182, or a pharmaceutically acceptable salt, hydrate, solvate, stereoisomer, polymorph, tautomer, isotopically enriched derivative, or prodrug thereof; wherein =====, Y, X, and n are as defined herein.

In certain embodiments of Formula (II-e), wherein X is —OH, the compound is:

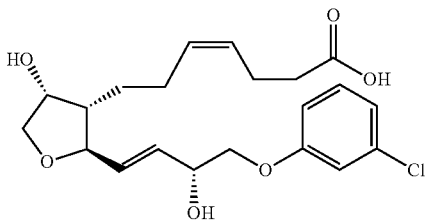

also referred to as AL-12182 free acid, or a pharmaceutically acceptable salt, hydrate, solvate, stereoisomer, polymorph, tautomer, isotopically enriched derivative, or prodrug thereof; wherein =====, Y, X, and n are as defined herein.

Other compounds of Formula (II) for use in the present invention are contemplated herein; See, e.g., Selliah et al, supra, incorporated herein by reference.

In certain embodiments, the compound of Formula (I) or (II) is a prodrug of any one of the compounds described herein. Exemplary prodrugs include esters, amides, and/or thioamides of the parent free acid and acyl groups present on the pentacyclic hydroxyl groups. Without being bound by any particular theory, the invention envisions that the free acid of compounds described herein (e.g. for example, wherein Z is =O, and X is —OH, such as, but not limited to bimatoprost free acid, travoprost free acid, latanoprost free acid, tafluprost free acid, or salts thereof) represents the principal pharmacologically active compound ("active metabolite") for the purposes of this invention. It is also envisioned that certain compounds of the present invention will serve as substrates for hydrolases in the body (e.g., esterases such as lipases, amidases), which will in turn produce the corresponding free acid in vitro or in vivo.

Pharmaceutical Compositions and Formulations

In certain embodiments, the present invention provides pharmaceutical compositions and formulations for use in any of the inventive methods, described herein, comprising one or more compounds of the Formula (I) or (II) described herein (the "active ingredient") and a pharmaceutically acceptable excipient.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

Pharmaceutical compositions described herein can be prepared by any method known in the art of pharmacology. In general, such preparatory methods include the steps of bringing the active ingredient into association with a carrier and/or one or more other accessory ingredients, and then, if necessary and/or desirable, shaping and/or packaging the product into a desired single- or multi-dose unit.

In certain embodiment, the pharmaceutical composition is formulated as a time release formulation, e.g., a sustained-release (SR), sustained-action (SA), extended-release (ER, XR, or XL), timed-release (TR), controlled-release (CR), modified release (MR), and continuous-release (CR) formulations, refer to dosage forms useful in releasing an active ingredient at a predetermined rate by maintaining a constant level of the active ingredient or active metabolite thereof in the bloodstream for a specific period of time with minimum side effect. Time release formulations may comprise imbedding the active ingredient in a matrix of insoluble particles, micro-encapsulation, use of liposomes and/or use of gels (e.g., hydrogels).

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include lipids/natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

A pharmaceutical formulation may comprise excipients that cause the active pharmaceutical ingredient(s) to be transported, trafficked, deposited, concentrated, and/or retained in adipose tissue or more specifically, in or near an adipocyte. For example, a "lipophilic excipient" (e.g., selected from the group consisting of an liposomes, oil, a surface active agent, an emulsifier, or a mixture thereof, as defined above and herein) may be used in an enteral (e.g., oral) formulation, whereby the active ingredient is administered with a lipophilic excipient, which together are absorbed by enterocytes of the small intestine and formed into chylomicrons, which are in turn preferentially transported by the bloodstream to adipose tissue. As an alternative example, liposomes may be used as a lipophilic excipient for enteral, parenteral, or topical formulation.

Liquid dosage forms for oral and parenteral administration include pharmaceutically acceptable emulsions, microemulsions, solutions, suspensions, syrups and elixirs. In addition to the active ingredient, the liquid dosage forms may comprise inert diluents commonly used in the art such as, for example, water or other solvents (e.g., ethyl carbonate, ethyl acetate, benzyl benzoate, dimethylformamide), fatty acid esters of sorbitan, polysorbates, solubilizing agents such as alcohols (e.g., ethyl alcohol, isopropyl alcohol, tetrahydrofurfuryl alcohol, benzyl alcohol, glycerol and glycols (e.g., 1,3-butylene glycol, propylene glycol, polyethylene glycols)), oils (e.g., cottonseed, groundnut, corn, germ, olive, castor, and sesame oils), Cremophor, cyclodextrins, polymers) and mixtures thereof. Besides inert diluents, the oral compositions can include adjuvants such as wetting agents, emulsifying and suspending agents, sweetening, flavoring, and perfuming agents. In certain embodiments, for parenteral administration, the active ingredient is mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be provided in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Compositions for rectal or vaginal administration are typically suppositories which can be prepared by mixing the active ingredient with a suitable non-irritating excipient or carrier such as cocoa butter, polyethylene glycol or a suppository wax which are solid at ambient temperature but liquid at body temperature and therefore melt in the rectum or vaginal cavity and release the active ingredient.

In certain embodiments, the pharmaceutical composition further comprises one or more excipients adapted for transdermal administration. Dosage forms for topical and/or transdermal administration of an active ingredient may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel. Exemplary carriers for transdermal administration include dimethyl sulfoxide, HRT (hormone replacement therapy) base, Pluronic™ lecithin organogel, Lipoderm®, Vanpen®, Aladerm®, and anhydrous gels.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices that limit the effective penetration length of a needle into the skin, such as those described in PCT publication WO 99/34850 and functional equivalents thereof. Jet injection devices that deliver liquid vaccines to the dermis via a liquid jet injector and/or via a needle that pierces the stratum corneum and produces a jet that reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices that use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 0.3% to about 10% (w/w) or (w/v) of the active ingredient, although the concentration of the active ingredient can be as high as the solubility limit of the active ingredient in the solvent. Formulations for topical administration may further comprise one or more of the additional ingredients described herein.

A pharmaceutical composition can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered, by rapid inhalation through the nasal passage from a container of the powder held close to the s suitable for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation suitable for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions that are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in Remington: The Science and Practice of Pharmacy 21st ed., Lippincott Williams & Wilkins, 2005.

Still further encompassed by the invention are kits comprising a compound as described herein and instructions for use. Kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

The active ingredient can be administered using any amount and any route of administration effective for treatment. The exact amount required will vary from subject to subject, depending on the species, age, and general condition of the subject, the severity of the infection, the particular composition, its mode of administration, its mode of activity, and the like.

The active ingredient is typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject will depend upon a variety of factors including the condition being treated and the severity of the condition; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The active ingredient can be administered by any route, including enteral (e.g., oral, rectal), parenteral (e.g., intravenous, intramuscular, intra-arterial, intramedullary, intrathecal, subcutaneous, intraventricular, interdermal), and topical administration (e.g., transdermal, transmucosal).

In certain embodiments, the active ingredient is administered systemically. As used herein, "systemic administration" or "administering systemically" or "systemic effect" means administration to the subject by enteral, parenteral, or topical (e.g., transdermal) administration, whereby the active ingredient or active metabolite thereof reaches and maintains a therapeutically effective concentration in the bloodstream for a period of time. A systemic effect is distinguishable from a local effect in a variety of ways, e.g., for example, as demonstrated in Example 1, a systemic effect is indicative of fat reduction in both treated and untreated areas of a subject's body.

In certain embodiments, "systemic administration" or "administering systemically" or "systemic effect" refers to the administration of an active ingredient to the subject, whereby the active ingredient or active metabolite thereof reaches and maintains a therapeutically effective concentration in the bloodstream for at least 4 hours, at least 8 hours, at least 10 hours, at least 12 hours, at least 15 hours, at least 24 hours, between 4 hours and 24 hours, between 8 hours and 24 hours, between 10 hours and 24 hours, or between 15 hours and 24 hours. In certain embodiments, the administration is transdermal administration. Without wishing to be bound by any particular theory, even if the active ingredient is eliminated rapidly from the bloodstream (e.g., latanoprost has a serum elimination half-life of about 17 minutes), transdermal administration can provide a depot effect whereby a single application to the skin can result in slow release of the active ingredient into the bloodstream, and thereby result in a more sustained therapeutically effective concentration in the bloodstream. Other formulations or techniques, such as time release formulations or continuous IV infusion, may enable this desired slow release of the active ingredient via other routes of administration.

In certain embodiments, the active ingredient is administered to the subject twice daily, daily, every 3 days, or weekly for at least 1 week, at least 2 weeks, at least one month, at least 2 months, at least 3 months, at least 4 months, at least 5 months, at least 6 months, between 1 week to 6 months, between 2 weeks to 6 months, between 1 month to 6 months, between 2 months to 6 months, between 3 months to 6 months, between 4 months to 6 months or between 5 months to 6 months. In certain embodiments, the administration is transdermal administration. In certain embodiments, the active ingredient is administered transdermally once daily.

The exact amount of the active ingredient required to achieve a therapeutically effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations). As demonstrated in the accompanying Examples, daily administration to the subject can be adequate (but not necessarily preferable) to achieve the desired effect. A daily administration schedule is considered convenient for human use. The active ingredient may be administered by the subject to himself or herself repeatedly and without special equipment or training, although a medical professional also can also administer the active ingredient to the subject.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

In certain embodiments, a therapeutically effective concentration of the compound is in the range of about 50 pg/ml and 1000 pg/ml, inclusive, e.g., greater than 50 pg/ml, greater than 60 pg/ml, greater than 70 pg/ml, greater than 80 pg/ml, greater than 90 pg/ml, greater than 100 pg/ml, greater than 150 pg/ml, greater than 200 pg/ml, greater than 250 pg/ml, greater than 300 pg/ml, greater than 350 pg/ml, greater than 400 pg/ml, greater than 450 pg/ml, greater than 500 pg/ml, greater than 550 pg/ml, greater than 600 pg/ml, greater than 650 pg/ml, greater than 700 pg/ml, greater than 750 pg/ml, greater than 800 pg/ml, greater than 850 pg/ml, greater than 900 pg/ml, greater than 950 pg/ml. The present invention contemplates a significant amount of compound or active metabolite thereof, e.g., the free acid, to appear systemically, i.e., in the blood. However, the concentration is not necessarily maintained within this range throughout the entire dosing interval, and may fluctuate during the dosing interval.

In certain embodiments, the compound is administered, e.g., orally, subcutaneously, or intravenously, at a dose of between about 0.5 mg in a 24-hour period and about 50 mg in a 24-hour period, inclusive, e.g., between about 0.5 mg to about 40 mg, between about 0.5 mg to about 30 mg, between about 0.5 mg to about 20 mg, between about 0.5 mg to about 10 mg, between about 0.5 mg to about 5 mg, between about 1 mg to about 50 mg, between about 10 mg to about 50 mg, between about 15 mg to about 50 mg, between about 20 mg to about 50 mg, between about 30 mg to about 50 mg, between about 40 mg to about 50 mg, in a 24-hour period, inclusive.

In certain embodiments, the compound is administered, e.g., to the skin, at a dose of between about 3 mg in a 24-hour period and about 50 mg in a 24-hour period, inclusive, e.g., between about 3 mg to about 40 mg, between about 3 mg to about 30 mg, between about 3 mg to about 20 mg, between about 3 mg to about 10 mg, between about 3 mg to about 5 mg, between about 5 mg to about 50 mg, between about 10 mg to about 50 mg, between about 20 mg to about 50 mg, between about 30 mg to about 50 mg, or between about 40 mg to about 50 mg, in a 24-hour period, inclusive.

In certain embodiments, the compound is administered, e.g., to the skin, and delivered to bloodstream of a subject a dose between about 0.05 mg and about 2 mg per hour, inclusive, e.g., between about 0.1 mg and about 2 mg, between about 0.5 mg and about 2 mg, between about 1 mg and about 2 mg, per hour, inclusive.

In certain embodiments, the compound is administered to the skin by a transdermal patch or gel.

In certain embodiments, a composition comprises greater than or equal to about 0.3% (w/v) of the active ingredient in order to achieve a systemic effect. In certain embodiments, the composition comprises greater than 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, or 10.0% (w/v) of the active ingredient. In certain embodiments, the composition comprises between about 0.4% and about 10%, weight per volume, inclusive. In certain embodiments, the composition comprises between about 0.4% and about 2%, weight per volume, inclusive.

In a particular embodiment, a composition for application to the skin comprises at or greater than or equal to about 0.3% (w/v) of the active ingredient in order to achieve a systemic effect. In certain embodiments, the composition comprises greater than 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, or 10.0% (w/v) of the active ingredient. In certain embodiments, the composition comprises between about 0.4% and about 10%, weight per volume, inclusive. In certain embodiments, the composition comprises between about 0.4% and about 2%, weight per volume, inclusive.

In a particular embodiment, a composition for subcutaneous injection comprises at or greater than or equal to 0.05% (w/v) of the active ingredient in order to achieve a systemic effect. In certain embodiments, the composition comprises greater than 0.1%, 0.3%, 0.5%, 1%, 2%, 3%, 4%, 5.0%, 6.0%, 7.0%, 8.0%, 9.0%, or 10.0% (w/v) of the active ingredient. In certain embodiments, the composition comprises between about 0.4% and about 10%, weight per volume, inclusive. In certain embodiments, the composition comprises between about 0.4% and about 2%, weight per volume, inclusive.

In certain embodiments, the compound is administered at a dose of about 0.5 mg/m$^2$/d to about 50 mg/m$^2$/d, e.g., between about 0.5 mg/m$^2$/d to about 40 mg/m$^2$/d, between about 0.5 mg/m$^2$/d to about 30 mg/m$^2$/d, between about 0.5 mg/m$^2$/d to about 20 mg/m$^2$/d, between about 0.5 mg/m$^2$/d to about 10 mg/m$^2$/d, between about 0.5 mg/m$^2$/d to about 5 mg/m$^2$/d, between about 0.5 mg/m$^2$/d to about 4 mg/m$^2$/d, between about 1 mg/m$^2$/d to about 5 mg/m$^2$/d, between about 2 mg/m$^2$/d to about 5 mg/m$^2$/d, between about 3 mg/m$^2$/d to about 5 mg/m$^2$/d, between about 3 mg/m$^2$/d to about 4 mg/m$^2$/d, between about 5 mg/m$^2$/d to about 50 mg/m$^2$/d, between about 10 mg/m$^2$/d to about 50 mg/m$^2$/d, between about 20 mg/m$^2$/d to about 50 mg/m$^2$/d, between about 30 mg/m$^2$/d to about 50 mg/m$^2$/d, or between about 40 mg/m$^2$/d to about 50 mg/m$^2$/d, in a 24-hour period, inclusive.

It is appreciated that more potent compounds may be administered at lower dosages than less potent compounds. For example, as shown in Example 3, a latanoprost dose of about 3.7 mg/m$^2$/d may be acceptable for systemic therapy, but for more potent compounds the systemic dose could be lower.

It will be also appreciated that the active ingredient can be administered in combination with one or more additional therapeutically active agents ("agents" or "active agents"). The compound or composition can be administered concurrently with, prior to, or subsequent to, one or more additional agents. In general, the active ingredient and each additional active agent will be administered at a dose and/or on a time schedule determined for the ingredient and agent. In will further be appreciated that the active ingredient and active agent utilized in this combination can be administered together in a single composition or administered separately in different compositions. The particular combination to employ in a regimen will take into account compatibility of the active ingredient with the active agent and/or the desired therapeutic effect to be achieved. In general, it is expected that additional active agents utilized in combination be utilized at levels that do not exceed the levels at which they are utilized individually. In some embodiments, the levels utilized in combination will be lower than those utilized individually.

The active ingredient can be administered in combination with active agents that improve their bioavailability, reduce and/or modify their metabolism, inhibit their excretion, and/or modify their distribution within the body. It will also be appreciated that therapy employed may achieve a desired effect for the same disorder (for example, an active ingredient can be administered in combination with an anti-inflammatory and/or anti-depressive agent, etc.), and/or it may achieve different effects (e.g., control of adverse side-effects).

Exemplary active agents include, but are not limited to, anti-obesity agents, steroidal agents, steroidal anti-inflammatory agent, non-steroidal anti-inflammatory agents, hormones, prostaglandins, progestational agents, anti-glaucoma agents, ophthalmic agents, diuretics, cardiovascular active agents, vasoactive agents, vasodilating agents, anti-hypertensive agents, angiogenic agents, or modulators of cell-extracellular matrix interactions (e.g. cell growth inhibitors and anti-adhesion molecules). Active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

Methods for Treating a Disorder Associated with Metabolic Syndrome

In one aspect, the invention provides a method of treating and/or preventing a metabolic syndrome or a disorder associated with metabolic syndrome in a subject in need thereof, comprising administering to a subject a compound of Formula (I) or (II).

The method encompasses administering one or more compounds of Formula (I) or (II) to a subject by any contemplated systemic route in an amount sufficient to treat and/or prevent metabolic syndrome or a disorder associated with metabolic syndrome in the subject. In certain embodiments, the compound is systemically administered to a subject transdermally. In certain embodiments, the compound is systemically administered to a subject orally. In certain embodiments, the compound is systemically administered to a subject parenterally.

In some embodiments, the disorder associated with metabolic syndrome is selected from the group consisting of obesity, dyslipidemia, and a diabetic condition, as described herein.

Methods for Treating Obesity

In this aspect, the present invention provides a method of treating and/or preventing obesity in a subject, comprising administering to a subject in need thereof one or more compounds of Formula (I) or (II).

The method encompasses administering one or more compounds of Formula (I) or (II) to a subject by any contemplated systemic route in an amount sufficient to treat and/or prevent obesity in the subject. In certain embodiments, the compound is systemically administered to a subject transdermally. In certain embodiments, the compound is systemically administered to a subject orally. In certain embodiments, the compound is systemically administered to a subject parenterally.

In certain embodiments, the present invention provides a method of reducing adipocytes in a subject, comprising administering systemically to a subject in need thereof one or more compounds as described herein. Reducing adipocytes in a subject includes, but is not limited to, reducing fat cell amount (e.g., for example, fat cell number), reducing fat cell volume, reducing fat cell formation, reducing fat cell maturation, dedifferentiating a fat cell, and/or inducing the death of a fat cell (e.g., for example, by apoptosis) as measured by at least one of volume, size, mass, bulk, density, amount, and/or quantity. In certain embodiments, the method of reducing adipocytes comprises reducing the fat cell amount, reducing fat cell volume, reducing fat cell formation, or reducing fat cell maturation, in a subject by greater than or equal to 75%, greater than or equal to 70%, greater than or equal to 60%, greater than or equal to 50%, greater than or equal to 40%, greater than or equal to 30%, greater than or equal to 25%, greater than or equal to 20%, greater than or equal to 15%, greater than or equal to 10%, or greater than or equal to 5%. Treating obesity can include reducing body weight or reducing body mass index (BMI). The present invention is expected to reduce body weight by greater than or equal to 75%, greater than or equal to 70%, greater than or equal to 60%, greater than or equal to 50%, greater than or equal to 40%, greater than or equal to 30%, greater than or equal to 25%, greater than or equal to 20%, greater than or equal to 15%, greater than or equal to 10%, or greater than or equal to 5%.

Treating obesity can include reducing body fat, as measured by at least one of volume, size, mass, bulk, density, amount, and/or quantity. Body fat can be measured by skin calipers, dual energy x-ray Absorptiometry (DEXA), computed tomography (CT), magnetic resonance imaging (MRI), or any other suitable method known in the art, The measurement can be of total body fat, or only body fat on a particular part of the body. Fat reduction can also include reducing fat cell amount (for example, fat cell number), reducing fat cell volume, reducing fat cell maturation, and/or dedifferentiating a fat cell. These phenomena can be seen and measured, for example, by histologic examination of body fat.

The present invention is expected to reduce fat by greater than or equal to 75%, greater than or equal to 70%, greater than or equal to 60%, greater than or equal to 50%, greater than or equal to 40%, greater than or equal to 30%, greater than or equal to 25%, greater than or equal to 20%, greater than or equal to 15%, greater than or equal to 10%, or greater than or equal to 5%.

In certain embodiments, the subject is overweight. "Overweight" is a medical condition, and is defined by the subject's BMI. Any subject with a BMI of greater than or equal to 25 is considered overweight. An overweight subject encompasses pre-obese subjects (e.g., having a BMI of between 25 and 30) and obese subjects (e.g., having a BMI of greater than or equal to 30). In some embodiments of the invention, methods or compositions used to treat or prevent "obesity" can likewise be used to treat or prevent "overweight" or "pre-obesity."

In certain embodiments, the overweight subject is obese and suffers from obesity. Any subject with a BMI of between 35 and 40, inclusive, is considered "severely obese" and suffers from "severe obesity". Any subject with a BMI between 40 and 45 is considered "morbidly obese" and suffers from "morbid obesity". Any subject with a BMI greater than or equal to 45 is considered "super obese" and suffers from "super obesity".

In certain embodiments, the subject has obesity as a side effect of medication (e.g., for example, cortisol and analogs, corticosteroids, megace, sulfonylureas, antiretrovirals, antidepressants, monoamine oxidase inhibitors, selective serotonin reuptake inhibitors, oral contraceptives, insulin or a form of insulin, risperidone, clozapine, and thiazolidinediones).

In certain embodiments, the subject has obesity due to changes in hormonal status (e.g., as a result of physiologic changes such as pregnancy or menopause).

In certain embodiments, the subject with obesity is undergoing or has recently undergone smoking cessation.

In certain embodiments, the subject with obesity is also suffering or likely to suffer from diabetes, hypertension, hyperlipidemia, coronary artery disease, stroke, sleep apnea, gallbladder disease, gastroesophogeal reflux disease, fatty liver disease, gout, thromboembolism, elevated blood pressure, elevated blood sugar, elevated serum cholesterol, elevated serum uric acid, cancer (e.g., breast cancer, colon cancer, lipomas, fatty tumors, particularly if there are multiple fatty tumors), or a genetic disorder or medical condition characterized at least in part by excess body fat (e.g., Cushing syndrome, pseudo-Cushing syndrome, drug-induced obesity, HIV-related lipodystrophy, partical lipodystrophy, benign symmetric lipomatosis, Madelung's disease, hypothyroidism, pseudohypoparathyroidism, hypothalamic obesity, polycystic ovarian disease, depression, binge eating, Prader-Willi syndrome, Bardet-Biedl syndrome, Cohen syndrome, Down syndrome, Turner syndrome, growth hormone deficiency, growth hormone resistance, and leptin deficiency or resistance). The present invention contemplates treating any such disease, disorder, or condition using any of the described inventive methods.

In certain embodiments, the subject is not overweight. For example, the method of reducing body fat in a subject is contemplated useful for not only treating obesity in a subject, but also useful in treating subjects who are not overweight, but still desire to increase the proportion of lean body mass to total body mass.

In certain embodiments, the subject does not suffer from metabolic syndrome.

In certain embodiments, the methods of the present invention are useful for treating or preventing an adipocyte-related disease. As used herein, "adipocyte-related disease" means a disease: (i) wherein reduction of adipocytes treats the disease, disorder, or condition from which the subject is suffering; or (ii) whose mechanism comprises an adipocyte and/or its molecular products, e.g., secreted proteins, e.g., adiponectin, resistin, tumor necrosis factor alpha (TNF-α), interleukin-6 (IL-6), C-reactive protein (CRP), fibrinogen, plasminogen activator inhibitor-1 (PAI-1), and/or C-terminal binding protein (CtBP). Exemplary adipocyte-related diseases include, but are not limited to, metabolic syndrome, excess body fat (e.g., being overweight, obesity), dyslipidemia, hypercholesterolemia, hypertriglyceridemia, diabetes (e.g., type 2 diabetes), atherosclerosis, vascular disease, coronary artery disease, stroke, cerebrovascular disease, peripheral vascular disease, fatty liver, pancreatitis, inflammation or inflammatory disease, depression, and dementia. In certain embodiments, the adipocyte-related disease is selected from the group consisting of metabolic syndrome, diabetes (e.g., type 2 diabetes), liver disease, atherosclerosis, fatty liver disease, inflammation or inflammatory disease, depression, and dementia. In certain embodiments, treatment of an adipocyte-related disease can be accomplished by reduction of adipocytes that is microscopic rather than macroscopic, or diffuse rather than focal.

Methods for Treating Dyslipidemia

In another aspect, provided is a method for treating and/or preventing dyslipidemia a subject in need thereof, comprising administering one or more compounds of Formula (I) or (II) to the subject.

The method encompasses administering one or more compounds Formula (I) or (II) to a subject by any contemplated route in an amount sufficient to treat and/or prevent dyslipidemia in the subject. In certain embodiments, the compound is systemically administered to a subject transdermally. In certain embodiments, the compound is systemically administered to a subject orally. In certain embodiments, the compound is systemically administered to a subject parenterally.

In certain embodiments, wherein the concentration of a lipid or lipoprotein in the blood is abnormally elevated, e.g., elevated serum triglycerides or elevated LDL, the method reduces the concentration by greater than or equal to 50%, by greater than or equal to 40%, by greater than or equal to 30%, by greater than or equal to 25%, by greater than or equal to 20%, by greater than or equal to 15%, by greater than or equal to 10%, and/or by greater than or equal to 5%.

In certain embodiments, wherein the concentration of a lipid or lipoprotein in the blood is abnormally low, e.g., low HDL, the method increases the concentration by greater than or equal to 50%, by greater than or equal to 40%, by greater than or equal to 30%, by greater than or equal to 25%, by greater than or equal to 20%, by greater than or equal to 15%, by greater than or equal to 10%, and/or by greater than or equal to 5%.

In certain embodiments, treating dyslipidemia comprises one or more of: reducing serum triglycerides, reducing serum total cholesterol, reducing serum LDL, and/or increasing serum HDL. In certain embodiments, the subject suffers from or is likely to suffer from a disease, disorder, or condition associated with dyslipidemia. In certain embodiments, the subject suffers from or is likely to suffer from a disease, disorder or condition selected from the group consisting of dyslipidemia, hypercholesterolemia, hypertriglyceridemia, a heritable disorder characterized at least in part by one or more abnormal serum lipid levels (e.g., familial hypercholesterolemia, familial hypertriglyceridemia), excess body fat (e.g., overweight, obesity), metabolic syndrome, vascular disease, atherosclerosis, coronary artery disease, stroke, cerebrovascular disease, peripheral vascular disease, diabetes (e.g., type 2 diabetes), fatty liver disease, hepatic fibrosis, pancreatitis, inflammation or inflammatory disease, depression, and dementia.

In certain embodiments, the subject does not suffer from metabolic syndrome.

Methods for Treating a Diabetic Condition

In another aspect, provided is a method for treating and/or preventing a diabetic condition in a subject in need thereof, comprising administering one or more compounds of Formula (I) or (II) to the subject.

The method encompasses administering one or more compounds of Formula (I) or (II) to a subject by any contemplated systemic route in an amount sufficient to treat and/or prevent a diabetic condition in the subject. In certain embodiments, the compound is systemically administered to a subject transdermally. In certain embodiments, the compound is systemically administered to a subject orally. In certain embodiments, the compound is systemically administered to a subject parenterally.

In certain embodiments, treating a diabetic condition comprises one or more of: reducing serum glucose, reducing glycated hemoglobin levels, reducing serum insulin, increasing insulin sensitivity, improving glucose tolerance (e.g., reducing the glucose levels measured during a glucose tolerance test), reducing a subject's need for another medication (e.g., insulin) to maintain normal blood sugar levels, and/or treating or preventing a diabetic complication.

In certain embodiments, the method reduces a serum glucose concentration, a glycated hemoglobin concentration, a serum insulin concentration, a medication requirement (e.g., insulin requirement), and/or incidence or severity of a diabetic complication by greater than or equal to 50%, by greater than or equal to 40%, by greater than or equal to 30%, by greater than or equal to 25%, by greater than or equal to 20%, by greater than or equal to 15%, by greater than or equal to 10%, and/or by greater than or equal to 5%.

In certain embodiments, the subject suffers from or is likely to suffer from a disease, disorder or condition selected from the group consisting of type 2 diabetes mellitus, type 1 diabetes mellitus, prediabetes, hyperglycemia, insulin resistance, hyperinsulinemia, diabetic nephropathy, diabetic retinopathy, diabetic neuropathy, atherosclerosis, coronary artery disease, stroke, myocardial ischemia, myocardial infarction, diabetic myocardial small vessel disease, diabetic gastroparesis, diabetic hearing loss, a diabetic skin disease, a diabetes-related infection, diabetic oral disease (e.g., gingivitis), diabetic acidosis (e.g., diabetic ketoacidosis), nonketotic hypersosmolar state, coma, and diabetic foot ulcer.

In certain embodiments, the subject does not suffer from metabolic syndrome.

Other Uses of the Compositions and Compounds

Given the ability of the compounds disclosed herein to reduce fat, adipocytes, and lipid concentrations, and the association of these species with metabolic pathways and disease (e.g., as part of the metabolic syndrome), it is further envisioned that the compounds, compositions, and methods described herein may be used to lower one or more of the following clinical parameters in a body: serum glucose concentration, glycated hemoglobin concentration (i.e., hemoglobin A1C, "HbA1c"), circulating insulin concentration, serum urate concentration, concentration(s) of hepatic serum biomarkers, e.g. transaminases, and concentrations of pancreas-related serum biomarkers, e.g. amylase and lipase. As used herein, the term "serum glucose concentration" is intended to encompass any suitable measure of the concentration of glucose in the blood.

It is further envisioned that compounds, compositions, and methods described herein may be used to improve an individual's response to insulin (i.e., treat insulin resistance) or to leptin (i.e., treat leptin deficiency).

EXAMPLES

Throughout the description, where laboratory assays, e.g. for glucose or lipid concentrations, refer to a particular matrix, e.g. serum, it is to be understood that such assays may, depending on the analyte, be conducted on other matrices or sample types, e.g. plasma, or with other technologies, e.g., noninvasive methods, that yield comparable measurements.

Throughout the description, where compositions are described as having, including, or comprising specific components, or where processes are described as having, including, or comprising specific process steps, it is contemplated that compositions of the present invention may also consist essentially of, or consist of, the recited components, and that the processes of the present invention may also consist essentially of, or consist of, the recited processing steps. Further, it should be understood that the order of steps or order for performing certain actions are immaterial so long as the invention remains operable. Moreover, two or more steps or actions may be conducted simultaneously.

In light of the foregoing description, the specific non-limiting examples presented below are for illustrative purposes and not intended to limit the scope of the invention in any way.

Example 1

A randomized, controlled, repeat-dose, 4-week trial was conducted on (db−/db−) mice, which are defective for the leptin receptor (Jackson Laboratories). These mice are genetically obese, dyslipidemic, and diabetic.

Methods: Mice were obtained from Jackson Laboratories and acclimated to the facility. At about 5 weeks of age, mice were prospectively randomized into groups and assigned to the treatment conditions shown in FIG. 1. Topical treatments were applied in a thin film to the right flank skin without occlusive dressings; subcutaneous injections were also administered to the right flank. Mice were observed for condition and weighed daily. They were housed in the same room, in 11 cages according to group, and fed ad libitum. Skin tissue was sampled and serum lipids tested on day 28. Tissue was fixed in formalin and stained with hematoxylin and eosin.

Results: Animals fed and behaved normally throughout the study. Skin condition remained normal. Mean weight gain for days 0 to 28, by group, is shown in FIG. 2. Animals treated with vehicle only (Groups 1 and 2) showed an expected amount of weight gain for the strain (normative data, Jackson Laboratories). Transdermal bimatoprost isopropyl ester (BIE) and bimatoprost free acid (BFA) reduced weight gain significantly and in a dose-dependent manner, but topical bimatoprost did not. Subcutaneous BIE, subcutaneous BFA, and intraperitoneal BFA had no significant effect on weight gain.

FIG. 3 shows representative histologic sections of skin and subcutaneous fat from untreated (left) and treated (right) flanks of animals assigned to vehicle only (Group 1), topical bimatoprost 0.3% (Group 4), and topical BIE 0.3% (Group 11). All sections are shown at the same magnification (scale bar at top right=640 microns). The surface of the skin is oriented toward the top and left of each panel. Arrows in each section denote the panniculus carnosus, an anatomic layer that separates the first layer of subdermal fat from deeper, subpannicular fat (separation artifact is commonly seen deep to the panniculus and is not an in vivo process).

In vehicle-only treated animals (Group 1), the adipose layer between skin and panniculus was thick, with approximately 10 pseudo-layers of plump adipocytes.

In animals treated with topical bimatoprost 0.3%, smaller adipocytes and a thinner adipose layer were seen on the right (treated) flank but not on the left (untreated) flank. The untreated flank resembled that of a vehicle-treated animal, with a thick adipose layer and plump adipocytes. This observation is consistent with a local effect, but not a systemic effect, from topical bimatoprost at a concentration up to 0.3%.

In animals treated with topical BIE 0.3%, smaller adipocytes and thinner adipocyte layers were seen on both treated and untreated flanks. The effects were symmetric, indicative of a systemic effect. In contrast to animals treated with vehicle or bimatoprost 0.3%, animals treated with BIE 0.3% also showed profound shrinkage of adipocytes deep to the panniculus (toward bottom of each panel), closer to vasculature, and again indicative of a systemic effect.

Figure 5:
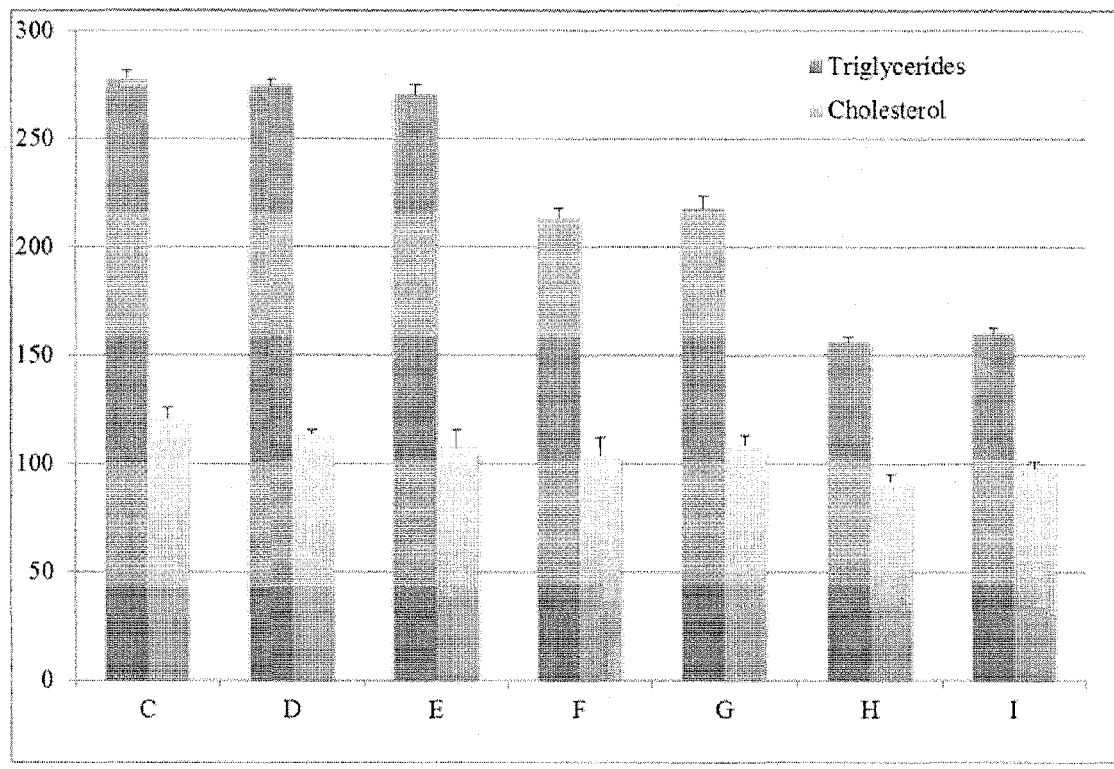
FIG. 5 charts the triglyceride and total cholesterol results (mg/dl) for the topical treatment conditions of FIG. 4 as follows: Group 1=C, 3=D, 4=E, 5=F, 6=G, 10=H, 11=I.

FIG. 4 shows mean, unfasted, serum lipid concentrations for each group (day 28), expressed as a percent reduction, relative to control (Group 1). FIG. 5 charts the triglyceride and total cholesterol results (mg/dl) for the topical treatment conditions as follows: Group 1=C, 3=D, 4=E, 5=F, 6=G, 10=H, 11=I.

Triglycerides were significantly reduced in animals treated with transdermal BFA (0.1% or 0.3%), and even more so in those treated with transdermal BIE (0.1% or 0.3%). Total cholesterol was significantly lower in animals treated with transdermal BIE 0.1%. Topical bimatoprost had no significant effect on serum lipids. Subcutaneous BIE, subcutaneous BFA, and intraperitoneal BFA had no significant effect on serum lipids.

Thus, in a mouse model of obesity and dyslipidemia, the foregoing results show reduced weight gain and serum lipids following transdermal administration of BIE and BFA, but not bimatoprost. Histology pointed to a systemic effect of BIE at concentrations tested, which was not seen with bimatoprost at the same concentrations. Thus, although adipose tissue was reduced by locally active treatment (e.g. by topical bimatoprost 0.3%), significant reductions in serum lipids and overall body weight appeared to occur only with systemically active treatment (e.g. topical BIE 0.3%).

For each of the above effects, transdermal BIE was more potent that transdermal BFA. Neither subcutaneous nor intraperitoneal administration of any compound had any significant effect due to the compound being quickly metabolized and extruded from the system. Transdermal administration appears to allow for a more slow exposure of the compound over a more lengthy period of time, e.g., over the dosing interval. Time-release formulations for subcutaneous and intraperitoneal administration of these compounds are contemplated as conferring a systemic effect similar to transdermal administration.

Example 2

A controlled, repeat-dose, 4-week, dose-ranging study of latanoprost transdermal cream was conducted in Zucker Diabetic Fatty (ZDF) rats (ZDF-Lepr$^{fa}$/Crl), which are defective for the leptin receptor, obese, hyperlipidemic, and diabetic.

Methods: Male ZDF rats, approximately 8 weeks old, were obtained from Jackson Laboratories and acclimated to the facility. They were prospectively assigned to treatment conditions shown in FIG. 6. There were 3 animals per treatment arm. Test articles were applied in a thin film to the right flank without occlusive dressings, at 0.3 ml daily for 28 days. Rats were fed ad libitum and housed in the same room in 4 cages according to group. They were observed for condition and weighed daily. Food consumption was measured by residual weight of chow. Animals were fasted overnight prior to day 29, and Oral Glucose Tolerance Tests were conducted on day 29 (1 g glucose per kg body weight). Skin tissue and serum chemistries were collected at day 29.

Results: Daily observations and skin condition were unremarkable. There were no differences in food consumption between treatment conditions. FIG. 7 shows mean weight gain, by group, for days 0 to 29. Compared to vehicle, topical latanoprost 0.5%, 0.05%, 0.005% caused a dose-dependent reductions in weight gain, which were statistically significant for the 0.5% and 0.05% concentrations.

Figure 8:
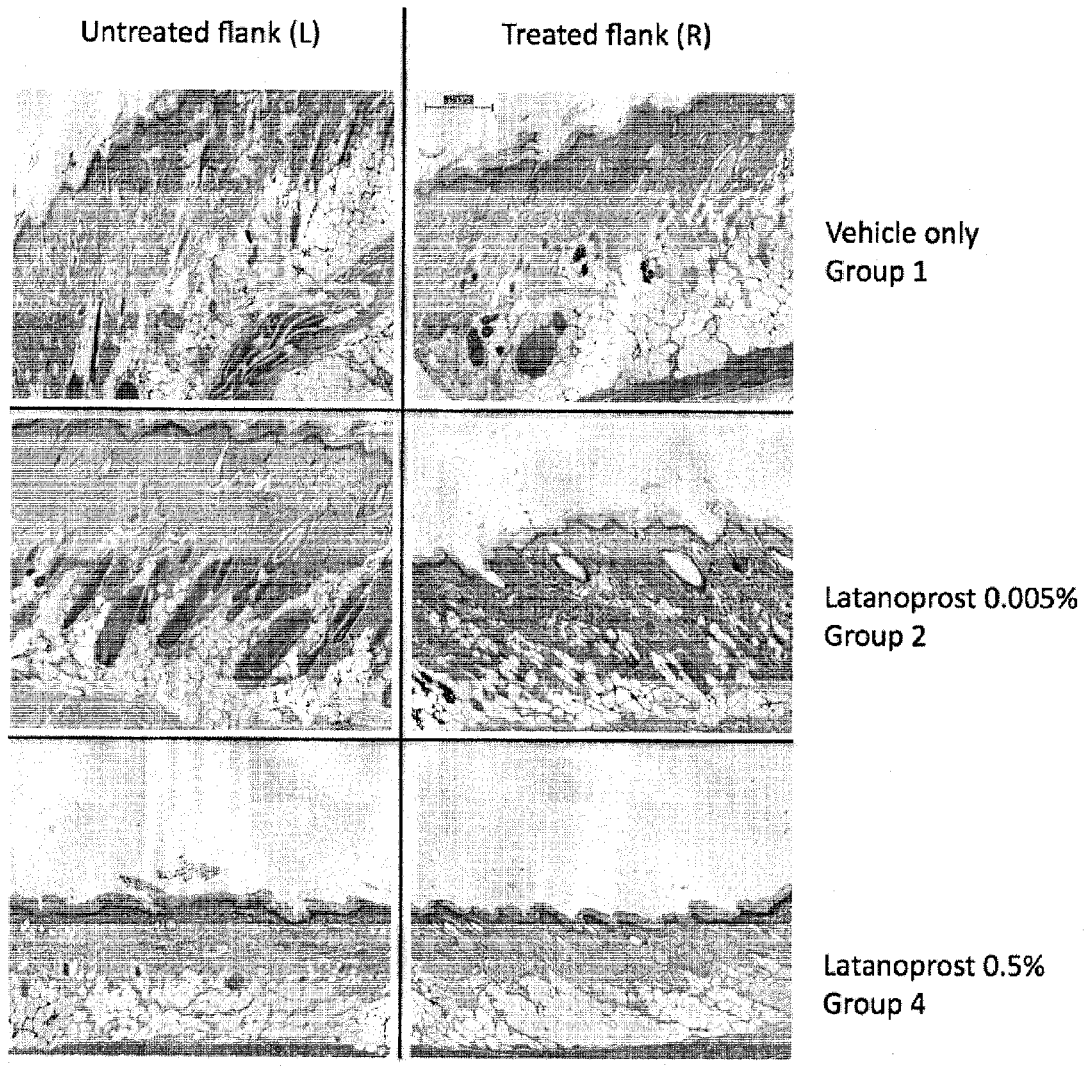
FIG. 8 shows representative histologic sections of skin and subcutaneous fat from untreated (left) and treated (right) flanks of animals assigned to vehicle only (Group 1), latanoprost 0.005% (Group 2), and latanoprost 0.5% (Group 4). All sections are shown at the same magnification (scale bar at top right=500 microns). The surface of the skin is oriented toward the top of each panel.

FIG. 8 shows representative histologic sections of skin and subcutaneous fat from untreated (left) and treated (right) flanks of animals assigned to vehicle only (Group 1), latanoprost 0.005% (Group 2), and latanoprost 0.5% (Group 4). All sections are shown at the same magnification (scale bar at top right=500 microns). The surface of the skin is oriented toward the top of each panel.

In vehicle-only treated animals (Group 1), subcutaneous adipose tissue consisted of several pseudolayers of plump adipocytes, which extended into the reticular dermis and were occasionally seen interspersed with panniculus muscle. The dermis was thick.

In animals treated with latanoprost 0.005%, the right (treated) flank fewer and smaller adipocytes, and a thinner adipose layer. Adipocytes were not interspersed with dermis, and the dermis was thinner than in vehicle-only animals. The untreated (left) flank resembled that of a vehicle-treated animal, with a thick adipose layer and full adipocytes. This observation is consistent with a local effect, but not a systemic effect, from topical latanoprost at a concentration of 0.005%.

In animals treated with topical latanoprost 0.5%, fewer and smaller adipocytes, and thinner adipose layer and dermis were seen on both treated and untreated flanks. The effects were symmetric, indicative of a systemic effect.

Figures 9, 10:
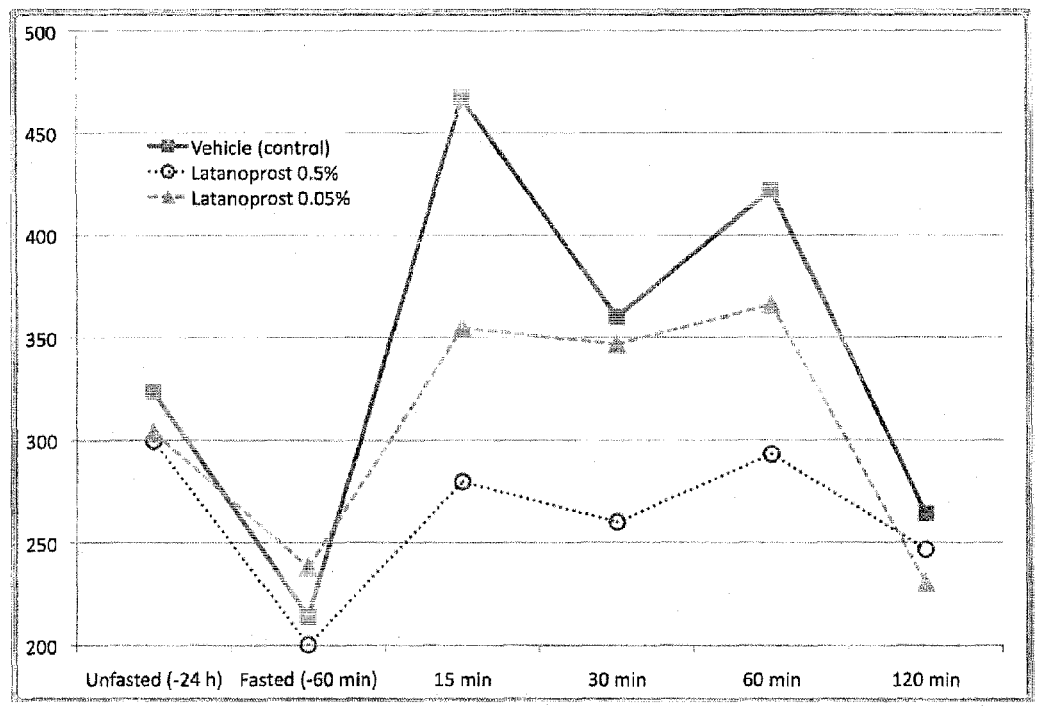
FIG. 9 summarizes serum lipid levels by group, as measured on day 29. Compared to vehicle-treated control animals, latanoprost was associated with dose-dependent reductions in triglycerides and LDL, and dose-dependent increases in HDL and HDL:LDL ratio. These benefits were seen at the 0.5% and 0.05% concentrations, and were absent at the 0.005% concentration. Because of the small sample size, these differences did not reach statistical significance, except for the HDL:LDL ratio of Latanoprost 0.5% vs. vehicle (one-sided p<0.05).
FIG. 10 shows the results of oral glucose tolerance testing on day 29. Latanoprost caused dose-dependent improvements in oral glucose tolerance, seen at the 0.5% and 0.05% concentration.

FIG. 9 summarizes serum lipid levels by group, as measured on day 29. Compared to vehicle-treated control animals, latanoprost was associated with dose-dependent reductions in triglycerides and LDL, and dose-dependent increases in HDL and HDL:LDL ratio. These benefits were seen at the 0.5% and 0.05% concentrations, and were absent at the 0.005% concentration. Because of the small sample size, these differences did not reach statistical significance, except for the HDL:LDL ratio of Latanoprost 0.5% vs. vehicle (one-sided p<0.05).

FIG. 10 shows the results of oral glucose tolerance testing on day 29. Latanoprost caused dose-dependent improvements in oral glucose tolerance, seen at the 0.5% and 0.05% concentrations (results for the 0.005% concentration [not shown] were similar to control). As summarized in FIG. 11, the serum glucose Area Under the Curve from 15 to 120 minutes post-glucose load ($AUC_{15-120}$) was 12% and 26% lower in animals treated with latanoprost 0.05% and 0.5%, respectively, compared to vehicle-treated animals. There was no effect on oral glucose tolerance with latanoprost 0.005%.

Thus, in a rat model of obesity, dyslipidemia, and diabetes, the foregoing results show reduced weight gain, improved serum lipids, and improved glucose tolerance following transdermal administration of latanoprost at concentrations of 0.5% and 0.05%, but not 0.005%. These effects were dose-dependent, and the minimum effective dose for these effects was deemed to be the 0.05% concentration.

Histology pointed to a systemic effect of latanoprost 0.5%, which was not seen with latanoprost 0.005%. Thus, although adipose tissue was reduced by locally active treatment (e.g. by topical latanoprost 0.005%), significant reductions in serum lipids and overall body weight appeared to occur only in response systemically active treatment (e.g. topical latanoprost 0.05% or 0.5%).

Example 3

FIG. 12 compares various topical doses of latanoprost in mouse, rat, and human, with respect to projected systemic dose. All calculations assume once-daily dosing and 100% serum bioavailability. The derivation of each dose is set forth based on the animal body weight, drug concentration, and drug volume. Finally, doses are scaled allometrically for body surface area ($mg/m^2/d$), as is appropriate for most low-molecular-weight molecules.

In the rat, the minimum effective dose of topical latanoprost for lipid, diabetes, and obesity reduction, which was 0.05%, equivalent to 0.5 mg/ml (Example 2), corresponds to a systemic dose of 3.6 $mg/m^2/d$. This is corroborated in the mouse (Example 1), where serum lipids and obesity responded to BIE, a close analog of latanoprost, at systemic doses of 10 $mg/m^2/d$; a minimum effective dose of BIE was not determined in the mouse.

In humans, administration of a latanoprost eye drop (Xalatan®), which is sufficient to reduce adipose tissue locally around the human eye, nonetheless involves a very low systemic dose of 0.008 $mg/m^2/d$, or 0.016 $mg/m^2/d$ if both eyes are treated. Thus, the recommended human ophthalmic dose, if both eyes are treated, is 450-fold lower than the minimum effective dose for lipid and obesity reduction in the rat.

Without any wish to be bound by theory, by comparison to the minimum effective dose of latanoprost in the rat, it is therefore predicted that a human transdermal dose of about 7 mg latanoprost per day would be sufficient to achieve a systemic benefit for serum lipids, a diabetic condition, and/or obesity. This could be delivered, for example, as a daily dose of 1 ml transdermal gel with a concentration 0.7% (w/v) or 7 mg/ml latanoprost.

Example 4

The following description exemplifies preparation of a pharmaceutical composition of latanoprost gel for transdermal administration to a human.

700 mg of pure latanoprost powder, made under Good Manufacturing Practice, is fully dissolved in 20 ml of an organic phase consisting of lecithin (about 10 ml), and isopropyl palmitate (about 10 ml). Into the organic phase is slowly mixed 80 ml of an aqueous phase, previously cooled to 4 degrees centigrade, consisting of poloxamer 407 (about 16-24 ml) and water (q.s.). Suitable preservatives (e.g., sorbic acid, potassium sorbate) are included in the formulation. The mixture is mixed well at room temperature until a gel forms, and the mixture is then processed through an ointment mill. About 100 ml of latanoprost transdermal gel is obtained, at a 7 mg/ml or 0.7% concentration.

Example 5

The following description exemplifies preparation of a pharmaceutical composition of latanoprost cream for transdermal administration to a human.

500 mg of pure latanoprost powder, made under Good Manufacturing Practice, is mixed in a mortar with 5 ml of ethoxy diglycol to form a paste. 100 ml of Lipoderm Base® (PCCA, Houston, Tex.) is added geometrically to the mortar. A suitable preservative such as potassium sorbate is added. The mixture is transferred to an electric mortar and pestle and mixed at 2 rpm for 2 minutes. Optionally, the mixture is then run through an ointment mill on setting #2, then setting #1. About 100 ml of latanoprost transdermal cream is obtained, at a 5 mg/ml or 0.5% concentration.

Example 6

The following description exemplifies preparation of a pharmaceutical composition of latanoprost anhydrous liquid for transdermal administration to a human.

630 mg of pure latanoprost powder, made under Good Manufacturing Practice, is mixed with 8.4 ml of benzyl alcohol, 33.6 ml of acetone, and isopropyl alcohol q.s. to 84 ml. The liquid is thoroughly mixed. About 84 ml of latanoprost transdermal liquid is obtained, at a 7.5 mg/ml or 0.75% concentration.

Example 7

The following description exemplifies a clinical application of the invention to treat obesity, dyslipidemia, and type 2 diabetes mellitus in a man with metabolic syndrome.

A 52-year-old man is suffers from obesity, dyslipidemia, and type 2 diabetes. Medical evaluation reveals that his height is 5 feet 8 inches and a weight of 240 pounds, corresponding to a body mass index (BMI) of 36.5 (clinically obese). His waist circumference is 42 inches. His noninvasive blood pressure is 184/98. His fasting serum glucose is 137 g/dL and his glycated hemoglobin (hemoglobin A1C) is 8.1. Fasting serum lipids are as follows: triglycerides, 220 mg/dL; total cholesterol, 310 mg/dL, LDL 240 mg/dL, HDL, 35 mg/dL. His physical exam is notable for prominent central (abdominal) obesity. In addition to medical therapy, the man's physician recommends a regimen of diet and exercise. After six months the man's weight, hemoglobin A1C, serum glucose, and serum lipids are unimproved. The physician prescribes systemic therapy with latanoprost, for example, a transdermal 0.7% gel in a metered-dose dispenser, with instructions to apply 2 ml metered dose once daily to the skin of the shoulders. After a period of time, for example from 1 to 6 months, the man's weight is reduced. Serum glucose, hemoglobin A1C, fasting serum LDL, and fasting serum triglycerides also diminish. Fasting serum HDL rises.

Example 8

The following description exemplifies a clinical application of the invention to reduce lipid concentrations in a patient with dyslipidemia and a history of coronary artery disease and myocardial infarction.

A 67-year-old woman with a history of obesity, hyperlipidemia, coronary artery disease, and myocardial infarction is found to have elevated serum triglycerides, total cholesterol, and low density lipoprotein, despite use of a statin. The woman's physician prescribes an oral, extended-release formulation of tafluprost, for example, an extended-release tablet comprising 5 mg tafluprost, with instructions to take one capsule by mouth daily. After a period of time, for example from 1 to 6 months, the woman's serum triglycerides, total cholesterol, and low density lipoprotein concentrations are reduced. Body weight is also seen to improve.

Other Embodiments

All patents, patent applications, and literature references cited herein are incorporated herein by reference.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of treating a diabetic condition selected from the group consisting of type 2 diabetes mellitus and a complication of type 2 diabetes mellitus in a subject, comprising administering systemically and transdermally to the subject a therapeutically effective amount of a compound selected from the group consisting of:

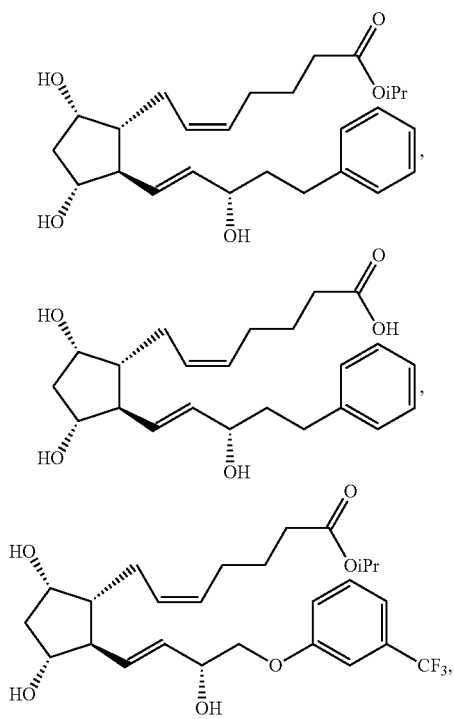

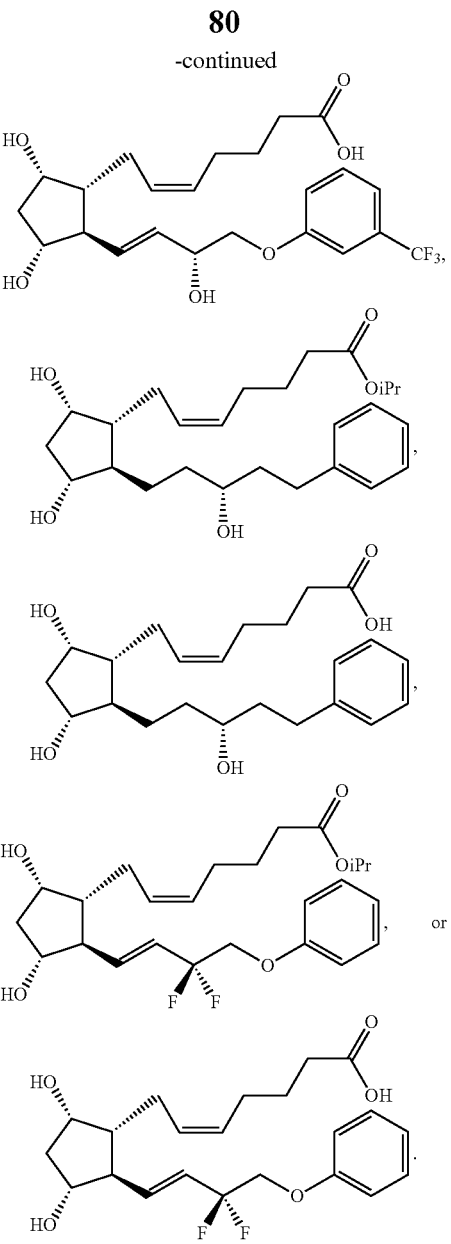

2. The method of claim 1, wherein the diabetic condition is type 2 diabetes mellitus.

3. The method of claim 1, wherein the method improves glucose tolerance.

4. The method of claim 1, wherein the method reduces serum glucose.

5. The method of claim 1, wherein the method reduces glycated hemoglobin.

6. The method of claim 1, wherein the method reduces the subject's need for insulin.

7. The method of claim 1, wherein the method treats a complication of type 2 diabetes mellitus in the subject.

8. The method of claim 7, wherein the complication of type 2 diabetes mellitus is selected from the group consisting of nephropathy, peripheral neuropathy, retinopathy, atherosclerosis, stroke, myocardial ischemia, infection, foot ulcers, acidosis, and coma.

9. The method of claim 1, wherein the compound is administered to the skin at a dose of between about 3 mg in a 24-hour period to about 50 mg in a 24-hour period, inclusive.

10. The method of claim 1, wherein the peak serum concentration of the compound or active metabolite thereof is between about 50 pg/ml and 1000 pg/ml.

* * * * *